US011259742B2

(12) United States Patent
Etleb et al.

(10) Patent No.: US 11,259,742 B2
(45) Date of Patent: Mar. 1, 2022

(54) SYSTEM, METHOD, AND COMPUTER READABLE MEDIUM FOR DYNAMIC PRESSURE DAMAGE RISK ASSESSMENT AND RESPONSE

(71) Applicant: CURIATO INC., Kitchener (CA)

(72) Inventors: Zied Etleb, Cambridge (CA); Abdelniser Ahmed Mooman, Waterloo (CA); Moazam Masood Khan, Waterloo (CA); Matthew Rubio-Sefati, Waterloo (CA); Abdul-Hakim Etleb, Cambridge (CA); Mahamad Eld Qusaybatie, Waterloo (CA); Faisal Hanif, San Jose, CA (US)

(73) Assignee: CURIATO INC., Kitchener (CA)

( * ) Notice: Subject to any disclaimer, the term of this patent is extended or adjusted under 35 U.S.C. 154(b) by 320 days.

(21) Appl. No.: 16/326,584

(22) PCT Filed: Aug. 21, 2017

(86) PCT No.: PCT/CA2017/000194
§ 371 (c)(1),
(2) Date: Feb. 19, 2019

(87) PCT Pub. No.: WO2018/032089
PCT Pub. Date: Feb. 22, 2018

(65) Prior Publication Data
US 2019/0175100 A1    Jun. 13, 2019

Related U.S. Application Data

(60) Provisional application No. 62/377,529, filed on Aug. 19, 2016.

(51) Int. Cl.
*A61B 5/00* (2006.01)
*G06N 20/20* (2019.01)
(Continued)

(52) U.S. Cl.
CPC ........... *A61B 5/447* (2013.01); *A61B 5/0022* (2013.01); *A61B 5/015* (2013.01); *A61B 5/1036* (2013.01);
(Continued)

(58) Field of Classification Search
CPC ....... A61B 5/447; A61B 5/6892; A61B 5/015; A61B 5/1036; A61B 5/4806;
(Continued)

(56) References Cited

U.S. PATENT DOCUMENTS

2013/0090571 A1* 4/2013 Nourani ................. G16H 20/30
600/587
2015/0371522 A1* 12/2015 Mravyan ............ A61G 7/05776
340/573.1

OTHER PUBLICATIONS

CNIPA, Office Action for Chinese Patent Application No. 201780063957.2 dated Mar. 12, 2021.
(Continued)

*Primary Examiner* — Michael J Brown
(74) *Attorney, Agent, or Firm* — Norton Rose Fulbright Canada LLP

(57) ABSTRACT

The present disclosure generally relates to the field of temporal and spatial risk mapping and risk response. More particularly, the present disclosure relates to spatial and temporal mapping of outcomes, risk analysis, and responsive and preventative actions derived through artificial intelligence driven workflow augmentation using spatial and temporal data mapping of data from a plurality of historical and streaming data sources.

26 Claims, 34 Drawing Sheets

(51) Int. Cl.
  *A61G 7/057* (2006.01)
  *G01L 1/20* (2006.01)
  *A61B 5/01* (2006.01)
  *A61B 5/103* (2006.01)
  *G05B 13/02* (2006.01)
  *G06N 5/04* (2006.01)
  *A61B 5/1495* (2006.01)

(52) U.S. Cl.
  CPC .......... *A61B 5/4806* (2013.01); *A61B 5/6892* (2013.01); *A61B 5/7264* (2013.01); *A61B 5/7275* (2013.01); *A61G 7/05776* (2013.01); *G01L 1/205* (2013.01); *G05B 13/0265* (2013.01); *G06N 5/047* (2013.01); *G06N 20/20* (2019.01); *A61B 5/00* (2013.01); *A61B 5/1495* (2013.01); *A61B 5/742* (2013.01); *A61B 2560/0223* (2013.01); *A61B 2562/029* (2013.01); *A61B 2562/0247* (2013.01); *A61B 2562/046* (2013.01); *A61G 2203/20* (2013.01); *A61G 2203/30* (2013.01); *A61G 2203/34* (2013.01); *A61G 2203/46* (2013.01)

(58) Field of Classification Search
  CPC ... A61B 5/0022; A61B 5/7275; A61B 5/7264; A61B 5/00; A61B 5/742; A61B 5/1495; A61B 2562/046; A61B 2560/0223; A61B 2562/0247; A61B 2562/029; G06N 20/20; G06N 5/047; G05B 13/0265; A61G 7/05776; A61G 2203/30; A61G 2203/20; A61G 2203/34; A61G 2203/46; G01L 1/205; G16H 20/30; G16H 50/30; G16H 50/20; G16H 40/63
  USPC ........................................................ 700/282
  See application file for complete search history.

(56) References Cited

OTHER PUBLICATIONS

Canadian Intellectual Property Office (CIPO), International Search Report and Written Opinion dated Dec. 13, 2017 for PCT Application No. PCT/CA2017/000194.

Yousefi et al., "A Smart Bed Platform for Monitoring and Ulcer Prevention", 4th International Conference on Biomedical Engineering and Informatics (BMEI), Oct. 15-17, 2011, pp. 1362-1366.

Wang et al., "The Development of an Intelligent Monitoring and Caution System for Pressure Ulcer Prevention", Proceeding of the 2011 International Conference on Machine Learning and Cybernetics, Jul. 10-13, 2011, pp. 566-571.

EPO, European Extended Search Report for EP Application No. 17840654.2 dated Feb. 24, 2020.

CNIPA, Office Action for CN Application No. 201780063957.2 dated Sep. 28, 2021.

* cited by examiner

FIG. 2

Multiplier Bottom Disc

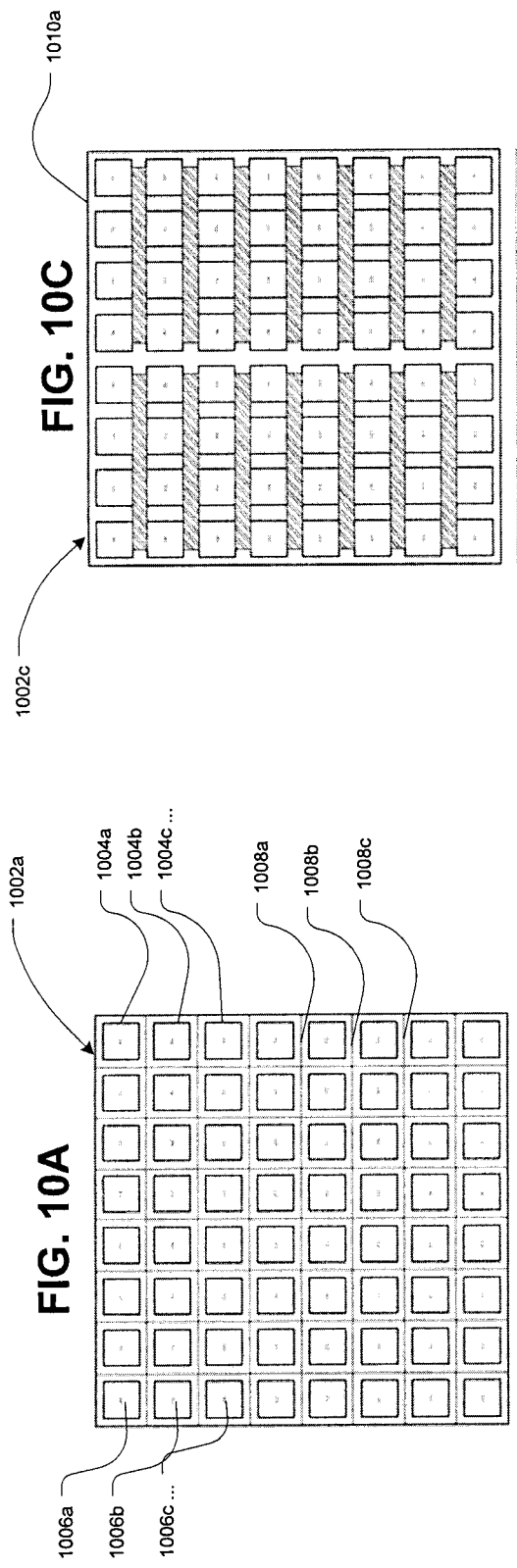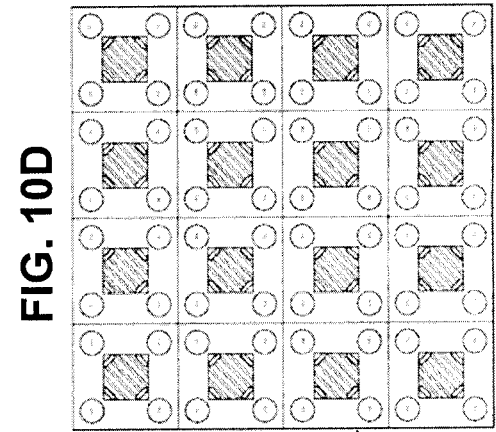

Figure 1: Patient Manager view. Provides high-level view of current users on Ceylon systems basic information, risk, status and next action.

FIG. 14

Figure 3: Risk Assessment Questionnaire.

SYSTEM, METHOD, AND COMPUTER READABLE MEDIUM FOR DYNAMIC PRESSURE DAMAGE RISK ASSESSMENT AND RESPONSE

CROSS REFERENCE

This application claims the benefit of U.S. provisional application 62/377,529 of the same title, filed Aug. 19, 2016, which application is incorporated herein in its entirety by this reference.

FIELD

The present disclosure generally relates to the field of temporal and spatial risk mapping and risk response. More particularly, the present disclosure relates to spatial and temporal mapping of outcomes, risk analysis, and responsive and preventative actions derived through artificial intelligence driven workflow augmentation using spatial and temporal data mapping of data from a plurality of historical and streaming data sources.

INTRODUCTION

Prolonged or inappropriate pressure may damage individuals or objects if un-noticed.

For example, preventing pressure injuries (referred to colloquially as bedsores and skin ulcers) has become a major goal for health-care organizations, health improvement groups, and accrediting organizations. Pressure injuries impose tremendous financial burden and are serious adverse events, thus, their prevention is an important challenge to health care providers.

Pressure injuries are associated with ill health and poor mobility, and have detrimental effects on patients' quality of life (Gorecki et al. 2009, 2012). According to the National Pressure Ulcer Advisory Panel (NPUAP), a pressure ulcer or pressure injury is a defined, localized injury to the skin and/or underlying tissue, which is usually over a bony prominence as a result of pressure, or pressure in combination with shear and/or friction. Pressure injuries are classified numerically according to the severity of the pressure injury and the tissue layers involved (The National Pressure Ulcer Advisory Panel, 2014).

SUMMARY

In accordance with an aspect there are provided systems, apparatus, and methods for pressure injury management and prevention which include automated control and wireless notifications, and which may integrate cloud services, big data analytics, Internet of Things inter-networking (IoT) and mobile computing in a cohesive offering. Some embodiments may provide both pressure injury treatment and prevention methods which are superior in effectiveness to current solutions.

Heat, pressure and moisture may be directly correlated in the formation of pressure injuries. Some embodiments may measure all three of these factors and may dynamically or automatically adjust the pressure in response in order to regulate, maintain, or alter the air pressure in a mattress. This may enable regulation of specific contact points between the patient and mattress while collecting, storing, and processing data produced by sensors (e.g., pressure sensors, climate sensors, etc.) in order to present a comprehensive assessment of insights, facts, historical data, and statistically supported and industry-validated research data.

In accordance with one aspect, there is provided a system for monitoring sensor data an entity undergoing prolonged contact with a surface, the system comprising: one or more sensors of a first type for detecting a first type of properties from the entity, the one or more sensors of the first type proximate to a contact between the entity and the surface; one or more sensors of a second type for detecting a second type of properties from the entity, the one or more sensors of the second type proximate to the contact between the entity and the surface; a processor operably linked to the one or more sensors of the first type and the one or more sensors of the second type, the processor configured to: receive sensor data from the one or more sensors of the first type; receive sensor data from the one or more sensors of the second type; combine received sensor data to produce a combined sensor data; generate a risk grid corresponding to one or more dimensions of the surface, the risk grid based on a historical risk data set stored in a memory; designate a portion of the risk grid as a null area if a null sensor reading is received from the sensor data pertaining to a portion the surface represented by the portion of the risk grid; detect at least one risk feature by processing the combined sensor data according to an AI model and the risk grid; determine a pressure risk score based on the at least one risk feature; generate a pressure redistribution plan based on one or more of the pressure risk score and the at least one risk feature; and transmit one or more of the pressure redistribution plan, the at least one risk feature, and the combined sensor data to a computer.

In accordance with another aspect, there is provided a system, comprising: at least one pressure redistributor for redistributing pressure exerted against the surface. the pressure relief system configured to receive instructions from the processor. the processor configured to: transmit the pressure redistribution plan to the pressure relief system as an pressure relief instruction set.

In accordance with another aspect, there is provided, a system wherein upon receipt of the pressure instruction set from the processor, the pressure relief system automatically executes the pressure redistribution plan to redistribute pressure exerted against the surface.

Example applications of the embodiments described herein included, for example: pressure injuries—collection of data related to indicators of pressure injuries, (said data being difficult to measure and identify on skin) localize risk models and then map those models to the actual body location to give a more refined and insightful view for decision makers; ship hull damage—a mesh of sensors can monitor a hull for damage. Using localized predictive analysis operators can produce visual outcomes and appropriate location for actions; rehabilitation monitoring—understanding fatigue and health of muscles and tendons is a difficult task for many rehabilitation experts. Utilizing the present disclosure a sensor mesh can be deployed to monitor variables such as oxygenation, blood flow, heat, and force distribution throughout the body to achieve a desirable outcome through predictive analysis and map appropriate actions. For example, compensation happening on the left leg could indicate fatigue occurring, where a notification is sent to warn of possible fatiguing of the left leg and recommendation for an alternative course of action based on the inputted workflow; mapping of actions spatially through augmented reality—if a user would like to view where actions need to occur on an entity. These actions can range from precision interventions to identifying where actions need to occur over a large area. For example, through the application of embodiments disclosed herein a surgeon can be presented with a view of the location of a susceptible hemorrhage occurring during a surgery.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 2 is block diagram depicting a top view of an air cell layer, according to some embodiments;

FIG. 10A is a plan view of the top layer configuration of an air cell mat, according to some embodiments;

FIG. 10B is a plan view of the bottom layer configuration of an air cell mat, according to some embodiments;

FIG. 10C is a plan view of a flexible printed circuit board (FPCB) configuration for a climate sensor layer, according to some embodiments;

FIG. 10D is a plan view of a FPCB configuration for pressure air cells underneath a pressure sensing layer, according to some embodiments;

FIG. 14 depicts an example risk assessment questionnaire user interface, according to some embodiments;

DETAILED DESCRIPTION

Figure 1:
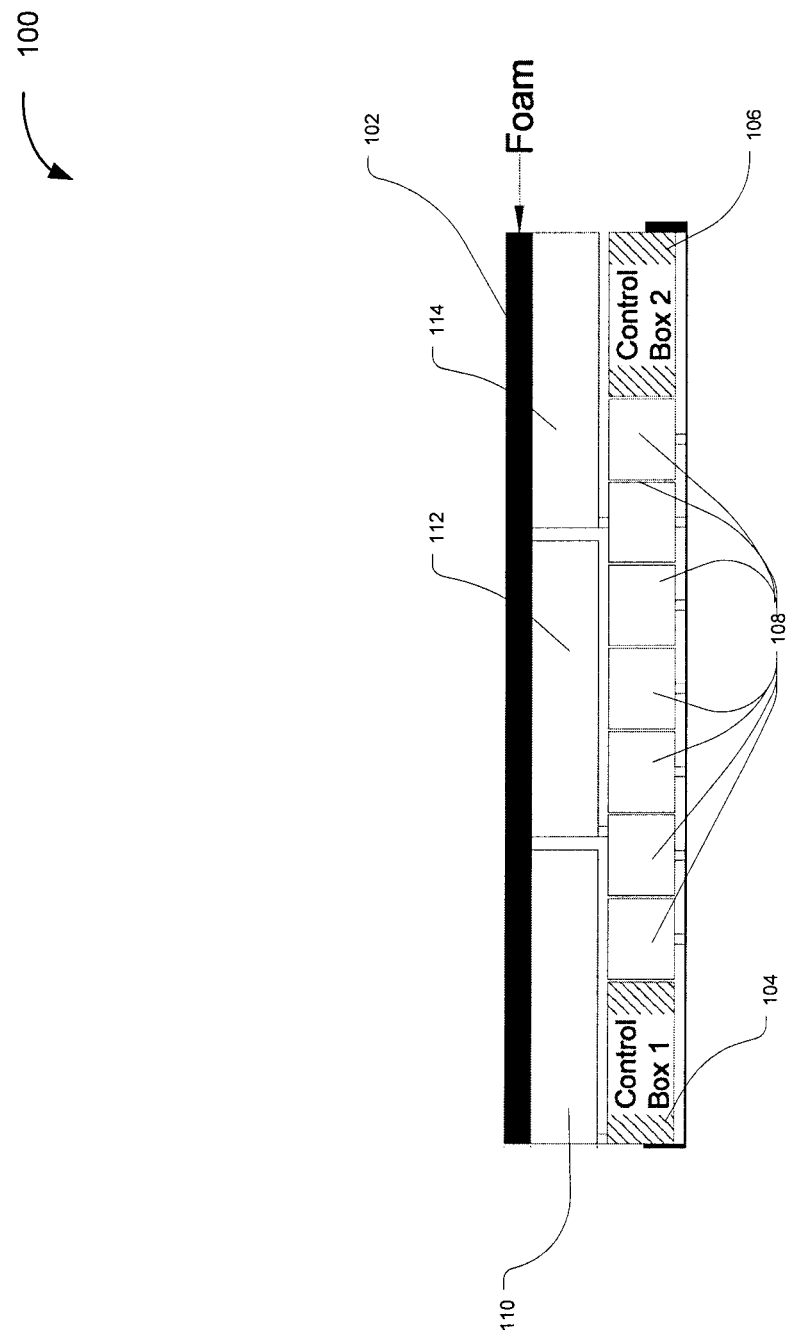
FIG. 1 is a block diagram depicting a pressure mitigation layer and two air cell layers, according to some embodiments.

The discussion included herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Preventing pressure injuries has become a major goal for health-care organizations, health improvement groups, and accrediting organizations. Pressure injuries impose tremendous financial burden and are serious adverse events, thus, their prevention is an important challenge to health care providers.

Pressure injuries are associated with ill health and poor mobility, and have detrimental effects on patients' quality of life (Gorecki et al. 2009, 2012). According to the National Pressure Ulcer Advisory Panel (NPUAP), a pressure ulcer or pressure injury is a defined, localized injury to the skin and/or underlying tissue, which is usually over a bony prominence as a result of pressure, or pressure in combination with shear and/or friction. Pressure injuries are classified numerically according to the severity of the pressure injury and the tissue layers involved (The National Pressure Ulcer Advisory Panel, 2014).

Those who are seriously ill and/or neurologically compromised (e.g. individuals with spinal cord injuries) are more likely to suffer pressure injuries (Elliott T R et al, 1999). Often, pressure injuries develop in areas of bony prominence; like the sacrum, buttocks, heels, hips, back, elbows, and head. Most patients who suffer such injuries cannot feel pain from lying in the same position for extended periods of time, or are unable to move themselves to relieve the pressure. This resulting sustained compression and tissue load causes impaired tissue blood flow and localized ischemia, which can ultimately result in the formation of pressure injuries (C. Bouten et al., 2001).

Groups known to be at high risk of developing pressure injuries include bed-bound and wheelchair-bound individuals, frail elderly persons with no or limited mobility, as well as individuals with diabetes, poor nutrition, and chronic blood flow diseases (U.S. Department of Health and Human Services, 1992).

Currently, the most common practice and effective care to prevent pressure injuries for immobilized patients, is for caregivers (nurses in particular) to manually turn patients over from side to side, approximately every two hours (D. Smith, 1995). This management of external loads allows the contact forces between the patient and the bed to be applied elsewhere, allowing for weight to be distributed appropriately to prevent pressure peaks in some critical load-bearing areas. Similarly, it is also desirable to monitor the skin condition, as early skin detection of compromised skin area by colour and warmth indicate potential skin breakdown. This approach relies on health care workers, primarily nurses. Diagnosis is made through a combination of actions. At the time of hospital admission, a physical examination is conducted and a medical history is taken, with a focus on physical and mental problems.

Skin integrity inspection and repositioning of the patient is often the first and most important step to preventing pressure injuries (N. Callum et al., 2000). Clinicians observe the patient's skin on a regular basis to identify any discolorations or warmth indicating potential skin breakdown. However, underlying tissue can become compromised by the time skin actually opens. Manually repositioning patients at risk and visually inspecting the integrity of the patient's' skin is not practical or scalable due to higher patient acuity and increasing nursing demands.

According to the U.S. department of Health, the projected supply and demand of nurses reflected a shortage of nurses in 2015 of 20%, and if not addressed, this shortage will grow to 29% by 2020. This increasing demand and shortage of nursing staff makes it increasingly difficult to provide the same level of service to all patients. This, coupled with a study finding that turning patients is also shown to be a significant cause of lower back pain in health workers would indicate that there is a necessity for an alternative to constant repositioning of patients by nurses. Said study indicated that in fact, 12% of nurses leaving the profession each year indicated back injuries as a cause of departure, and 52% of nurses currently suffer from chronic back pain (J. Martino., 2012). This coupling effect of both shortage and stress adds to the findings from in another study showing that only about 66% of patients at risk of developing pressure injuries receive both visual and manual distribution treatment on a regular basis, illustrating the difficulty for health care personnel to check their patients' several times throughout the day (S. Rich et al., 2011).

To add to the problem, there are also limitations involved with manual distribution of mechanical loads on soft tissue body parts, due to the turning process inadvertently causing distortion and shear stress to the skin, which results in damage making it increasingly difficult for health care personnel to prevent pressure injuries (S. Rithalia et al., 2000). Higher patient acuity and increasing demands on nurses (A. Hofman, R. Geelkerken, J. Wille, J. Hamming, J. Hermans, P. Breslau, "Pressure sores and pressure-decreasing mattresses: controlled clinical trial," Lancet, vol. 343, pp. 568-571, 1994.), it is difficult, if not impossible, for health care personnel to check their patients' skin and manually redistribute patients several times throughout the day. It will is therefore important to find ways to better leverage nursing staff, while providing the same quality or even better standards of care.

Technology has been found to show the potential to amplify and complement the abilities of the caregiver to increase the caregiver's ability to efficiently and successfully monitor and care for patients with regard to pressure injuries (K. Drayton, 2012). There are several hospital beds which perform various functions to assist in the care and prevention of pressure ulcers. Currently available technologies reveals a large number of anti-pressure injury devices that are deployed on the market, or are in the process of development, that perform various functions to assist the care and prevention of pressure injuries (G. Bardsley, 1999). Such pressure injury prevention devices are targeted towards preventative measures and focus on managing repetitive or sustained external loads on soft body tissues.

Currently available pressure injury prevention devices mainly take the form of bedding systems. These bedding systems range between passive and active based pressure relief support devices, and have been used for the past 40 years. Pressure relief devices have remained relatively unchanged over this 40 year period. Five studies reported no statistical difference in the effectiveness of these pressure relief devices, the relative benefits of these devices is unclear (T. Conine et al., 1990) (D. Daechsel et al., 1985) (S. Sideranko et al., 1992) (K E. Anderson, 1982) (P. Price et al., 1999).

Treatment of pressure injuries in clinical practice of risk assessment and skin assessment is viewed as two separate processes. This creates a limitation in that nurses, in their clinical assessment, may disregard the presence of an existing pressure injury as a contributory factor, which can lead nurses to fail to initiate appropriate interventions of secondary prevention and treatment (L. Pinkney et al., 2014) There is an apparent need to streamline the assessment process to incorporate a screening stage that would allow those who are 'not at risk' to be quickly identified, preventing the need for a more detailed full assessment. In addition to the ongoing research into the inefficiencies of current standard practice, ongoing research is revealing that shear, friction and microclimate also have important roles, and that there are significant and complex relationships between all of the extrinsic factors in pressure injury formation (according to a recent consensus document posted in the International guidelines of pressure ulcer prevention (International Guidelines on Pressure Ulcer Prevention, 2009)). This has been gaining significant attention due to recent advancements in sensing technology that could be used to measure key physical body parameters, in a non-obtrusive way (e.g., interface pressure measurement). Additional measurements, such as heart rate and movement patterns of a sleeping person in a bed have also been tested.

Currently, there are several devices that have been proposed by researchers as possible components of solutions to measure body parameters involved in the extrinsic factors in pressure injury formation. Such devices include piezoelectric sensor films, pressure sensing mats, and strain gauge based force sensors. Researches have also proposed various potential diagnostic sensor configurations, such as configurations capable of measuring skin color and blood perfusion, as well as blood oxygen content (A. Lima et al., 2008) (D. B. Murray et al., 2008)

This has led to the development of intelligent monitoring systems to record postures by detecting various limbs using pressure mats, for example in (C. Hsia et al., 2008). This enables healthcare clinicians to assess the potential risk of pressure injury formation on each limb, as different postures expose limbs to differing amounts of pressure load, which alter when a patient moves. This allows for targeted and insight-based pressure redistribution when manually repositioning patients at set time intervals. Nonetheless, clinicians still rely on both the conventional visual inspection of skin and manual redistribution by turning the patient at set intervals.

Recent developments include intelligent monitoring systems becoming integrated into the hospital beds in order to provide automatic redistribution of the patient. Automatic redistribution in such instances may be performed in response to real time biological data of the patient, including measurement of key parameters involved in pressure injury formation. Since interaction with the hospital bed and patient, due to interface pressure (bedding), is a key cause of pressure injuries, a smart bed may provide a first line of defense in preventing pressure injuries. With this goal in mind, the hospital bed can be viewed as a source of bio-signal data collection that can be leveraged in a sensor-based engineering approach, to redistribute pressure loads and other extrinsic factors.

This new perspective has spawned the development of several types of smart bed mattresses focused on pressure injury prevention. (S. Nageswaran et al., 2012). For example, the IANSiS (Intelligent adaptive surface) bed, developed at the University of Wisconsin, uses 5724 plastic programmable pins that enable the discretization of the bedding area into smaller sub-areas, and manipulating the position of the pins in order to cause interface pressure shifts based on real time interface pressure data in hopes of overall reduction of the maximum/average pressure loads (G. Fiedler et al., 2009). However, with this approach, since the pins are close together they can increase shear forces on the skin, thus leaving the possibility for progression of more serious pressure injury stages.

Authors K. S Jaichandar and E. Garcia developed the "intelli-Sense" smart bed system, which (K. S. Jaichandar, 2011) uses a different approach of focusing on the parameter of skin temperature, using an array of temperature sensors connected to air flow control modules, that provide air flow underneath the patient, causing the change in local microclimates (temperature and wetness). The drawback with this approach is that pressure, an important body parameter involved in the formation of pressure injuries is not taken into consideration, leaving the system susceptible to early onset pressure injury formation. These devices are necessary but not sufficient. Off-the shelf sensor arrays can be used to capture the pressure map, but the level and accuracy provided by patents have too high of an error margin to be used in an intelligent monitoring system, due to the level of the processing required for the smart bed application, is not commercially available.

Specifically, a time-stamped distribution image of all the environmental factors involved in pressure injury formation that can be constructed to facilitate detection/classification (body movement analysis), local risk identification, and potentially visualization of relevant data that can be used to drive a closed loop system to automate and simplify the entire process of pressure injury management.

Current solutions do not provide preventative measures, but focus rather on the analytics once the pressure injury has formed. Furthermore, research dictates that pressure is not the only metric used to determine pressure injuries. Humidity and temperature are equally important in the formation of pressure injuries. The market for pressure injury treatment products is also witnessing the introduction of innovative mattresses and beds for treatment. Shift in trends towards home based care is also driving the demand for such products.

Some embodiments may produce forward looking projections using suitable sets of assumptions and methodologies. Such projections may pertain to wound presentation, individual user (e.g., patient) risk factors, and the features and categories of available response actions. An artificial intelligence may collect these data, projection, risk factors, and feature and categories of available response action in order to produce recommended response action which may be presented (e.g., to the clinician).

In some embodiments, once a recommended response action has been produced, it may be executed as well (e.g., the bed automatically redistributes pressure). Further, an end user (e.g., clinician) may be notified (e.g., via a push notification message or email message).

In some embodiments, the requirement to evaluate recommended response actions and executed response actions on an ongoing basis in order to support ongoing treatment and/or justify a change may be a continual process. As a result, said process may become more effective with time as more data is collected (e.g., data pertaining to a single patient).

Embodiments described herein may disclose a smart pressure injury prevention system which may monitor patients' skin in order to collect data pertaining to pressure, temperature, and wetness. This data may be collected by multiple sensors with a high degree of precision (e.g., 1 by 1 inch, 1 by 1 cm, etc.). Collected data may then be processed through an artificial intelligence engine (AI Engine) to determine the vulnerability of a patient's skin and to redistribute pressure if needed using a plurality of pressure adjustable air cells (in some cases this may be 144 cells). It will be understood that the number of adjustable air cells included in implementations of the present disclosure may increase or decrease based on suitability.

In some embodiments, a pressure mitigation layer may be included between the sensor mat layer and air cell layer in order to increase patient comfort. This may reduce the movement felt by a patient while still allowing pressure adjustment in order to adjust the firmness of the pressure mitigation layer.

In some embodiments, a plurality of sensors may detect pressure, temperature, and wetness, and the output of the plurality of sensors may be used to create three mapping systems. Academic research has demonstrated that properly implemented pressure mapping allows accurate prediction of body areas that may be at risk for suffering pressure injuries (e.g., nurses may be notified of the areas of potential bedsores). By indicating areas detected by the sensors as undergoing higher pressure, the systems, methods, and apparatuses described herein may convey when (and what type of) pressure redistribution is necessary. Thermal mapping may employ a plurality of thermal sensors to detect inflammatory responses exhibited by skin. Wetness mapping may employ a plurality of wetness sensors (which may include, but are not necessarily limited to, sensors able to detect humidity) to provide information regarding the relationship between detected wetness with the presence of potential bodily fluids and pressure injuries.

In some embodiments, a software platform may analyze data from pressure sensors, wetness sensors, and thermal sensors, and may provide notifications to health care professionals (HCPs) as well as provide dynamic schedule (e.g., for patient redistribution), thereby keeping HCPs responsible for wound management well informed and enhancing their effectiveness. Currently, the absence of notifications and dynamic scheduling functionality may induce stress for nurses and caregivers, because they are unaware of the state of patients at any given time.

Referring to FIG. 1 a block diagram are provided, each depicting portions of a pressure mitigation layer and air cells, according to some embodiments. A depiction of control modules 104, 106 and foam mitigation 102 layer and an example double air cell layer 110-114 is provided. The purpose of the double layer air cells 110-114 may be to ensure efficient redistribution of pressure (according to a redistribution plan) exerted upon a surface by anatomical areas of a user's (e.g., a hospital patient's) body which are at high risk of pressure injuries. The control modules 104, 106 may regulate the information and data gathered from the sensors forming part of various sensory layers which may measure properties exhibited by air cells 110-114 as a user lies atop of foam mitigation layer 102. The foam mitigation layer 102 may ensure comfort for the user and may be constructed of a material designed to provide comfort to the user while protecting components of the system 100 from excessive moisture.

In some embodiments, the use of a two layer perpendicular air cell 110-114 design may allow for targeted control of pressure exerted against specific areas of the body of a user by controlling air pressure in the air layers 110-114. As a non-limiting example, they system may allow for low pressure at a specific area of a user's body by deflating one or more air cells 110-114 beneath the specific area of the user's body.

Figure 2:
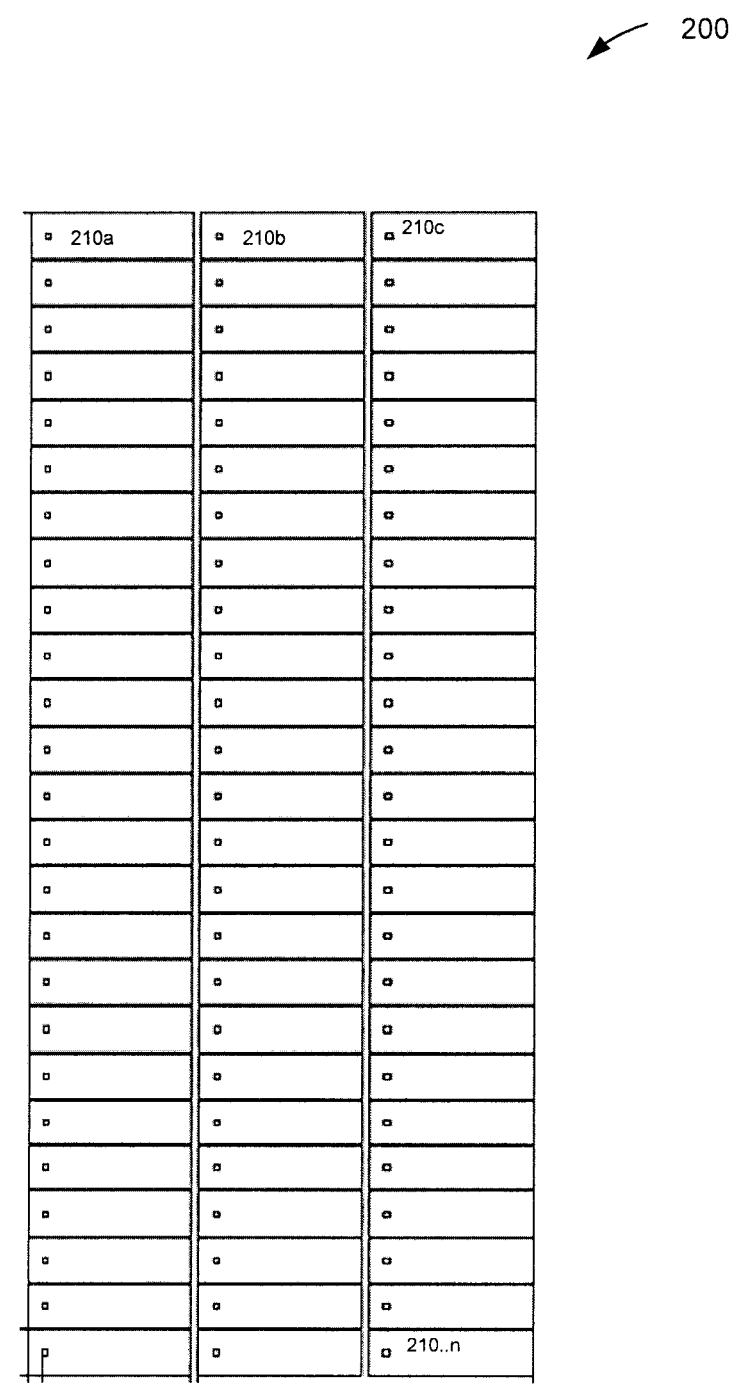

FIG. 2 may depict a top view depicting an array of air cells 210a-210 . . . n in a pressure mitigation layer. The block diagram included may depict the top layer of the air cells 210a-210 . . . n which may be controlled by a valve multiplier. The surface of the air cells may be equipped with one or more climate sensors, while one or more pressure sensors may be contained within each of the air cells 210a-210 . . . n.

In some embodiments, one or more valve multipliers may be utilized to enable individual control of air pressure exerted by each of the air cells 210a-210 . . . n in system 100 or a subset thereof (e.g., selective control of only those air cells 210a-210 . . . n underneath the body of a user). Beneath the depicted top layer of air cells 210a-210 . . . n there may be an additional layer of air cells which may the arranged in a perpendicular arrangement in regard to the depicted array of air cells 210a-210 . . . n. Air cells 210a-210 . . . n in each layer may be independently controllable as described above, and. In some embodiments, one or more valve multipliers may be coupled to each air cell 210a-210 . . . n, and air Cells 210a-210 . . . n may be connected to said valve multipliers by collapsible tubing or fabric.

Figure 3A:
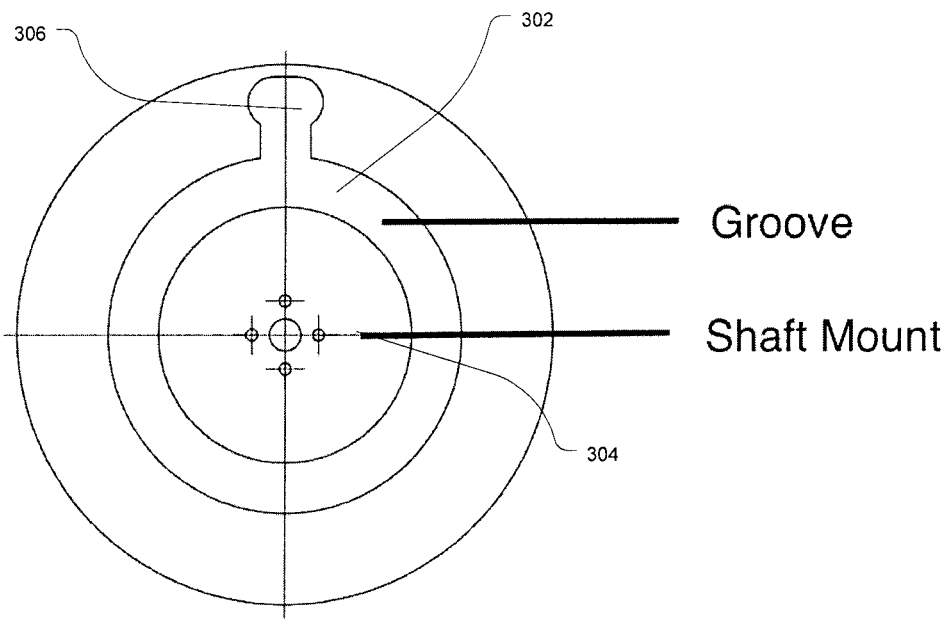
FIG. 3A is a schematic diagram depicting a top view of a top portion of a valve multiplier, according to some embodiments.
Figure 3B:
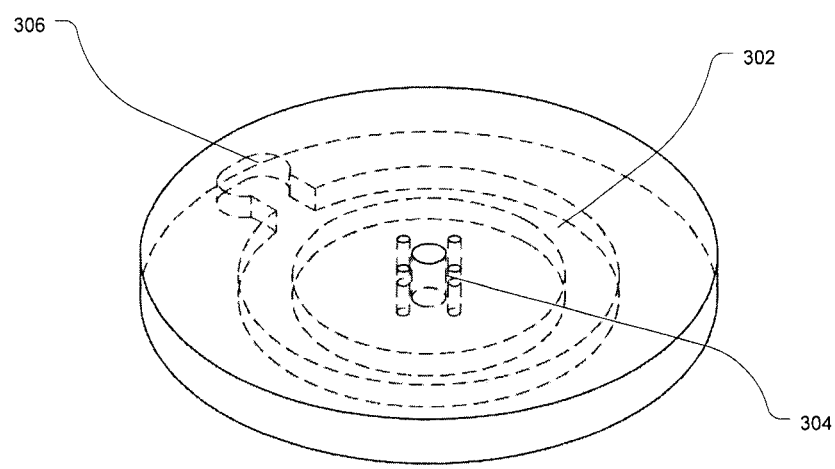
FIG. 3B is a schematic diagram depicting an isometric view of a top portion of a valve multiplier, according to some embodiments.

Referring to FIGS. 3A and 3B, schematic diagrams are provided each respectively depicting a top and an isometric view of a top portion of a valve multiplier, according to some embodiments. Groove 304 may be a circular channel in a portion of the valve multiplier. The circular channel created by groove 304 may function to air from the pressure pump to flow through the top portion of valve multiplier and reach aperture 306.

Figure 4A:
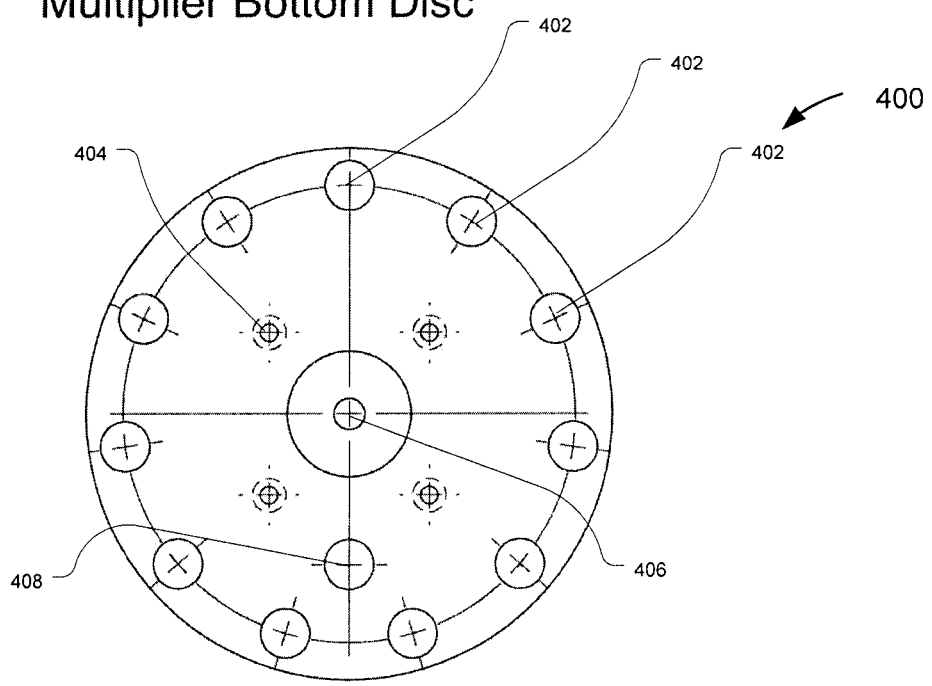
FIG. 4A is a schematic diagram depicting a top view of a bottom portion of a valve multiplier, according to some embodiments.
Figure 4B:
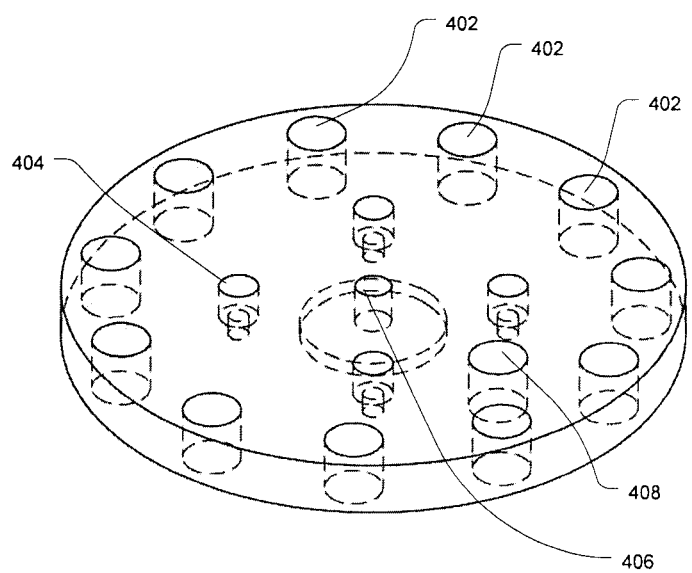
FIG. 4B is a schematic diagram depicting an isometric view of a bottom portion of a valve multiplier, according to some embodiments.

Referring to FIGS. 4A and 4B, there are provided schematic diagrams respectively depicting a top view and an isometric view of a bottom portion of a valve multiplier, according to some embodiments. Bottom portion of valve multiplier may include one or more motor mounting points 404, a plurality of outlets 402, at least one shaft insert 406, and at least one inlet 408. Motor mounting points 404 may function to enable a motor to be attached and/or coupled to the bottom portion of valve multiplier. The plurality of outlets may be circular channels in the body of the bottom portion of valve multiplier. The plurality of outlets may comprise the exit point of channels in the bottom portion of valve multiplier, the inlets of said channel may be inlet 408. Shaft insert 406 may function to enable a drive shaft of a motor to be rotatably coupled to the bottom portion of valve multiplier. Operation of said motor may, in turn, cause the bottom portion of drive shaft to rotate around an axis (e.g., drive shaft coupled to shaft insert 406). Rotation of bottom portion of valve multiplier in relation to top portion of valve multiplier may cause outlets 402 to align with aperture 306 of top portion of valve multiplier. As a result, rotation of bottom portion to specific degrees may cause air expelled from a pressure pump to be expelled from specific outlets 402 in bottom portion of valve multiplier.

Figure 5:
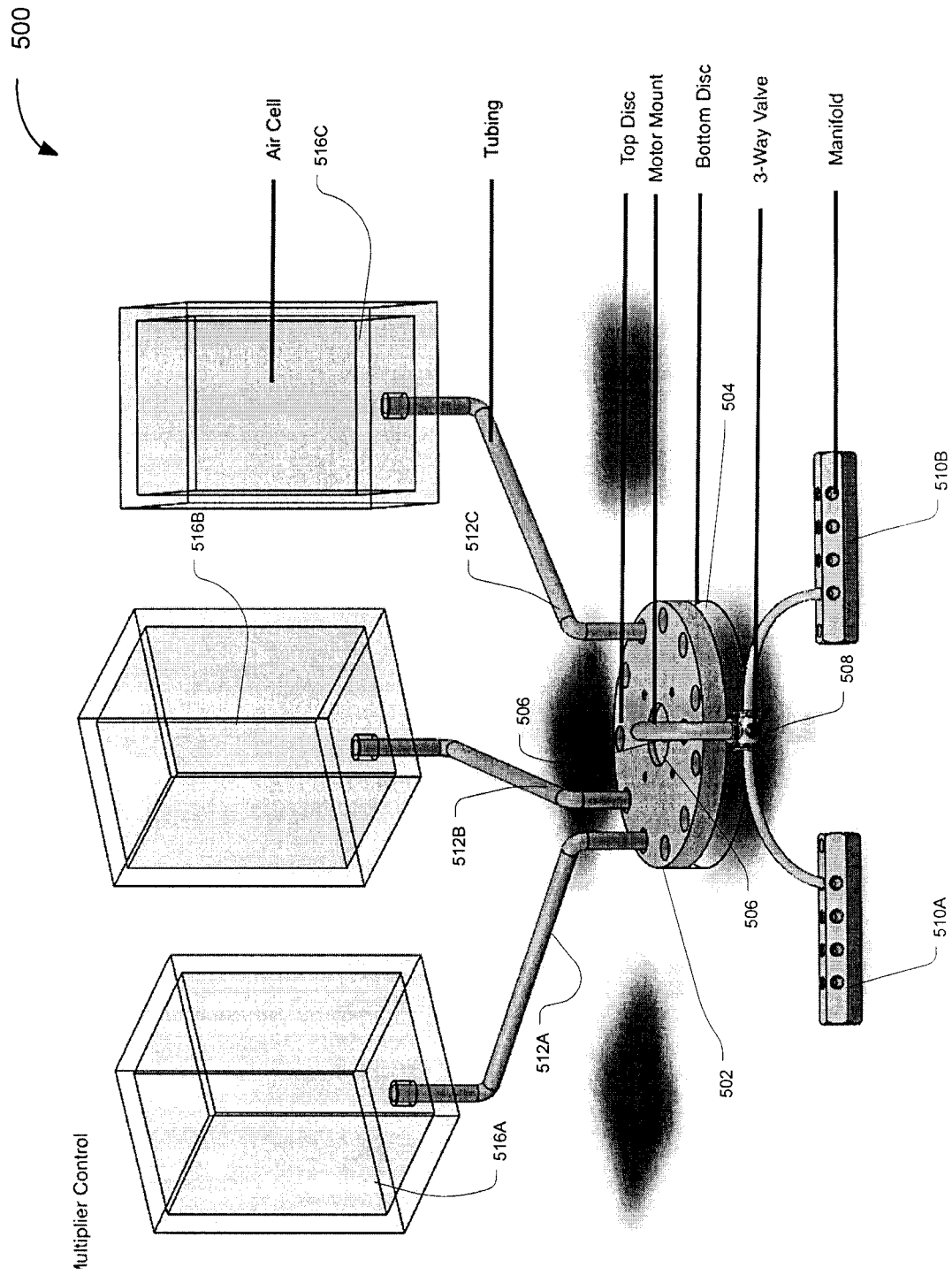
FIG. 5 is an isometric view of components of a valve multiplier system, according to some embodiments.
Figure 6:
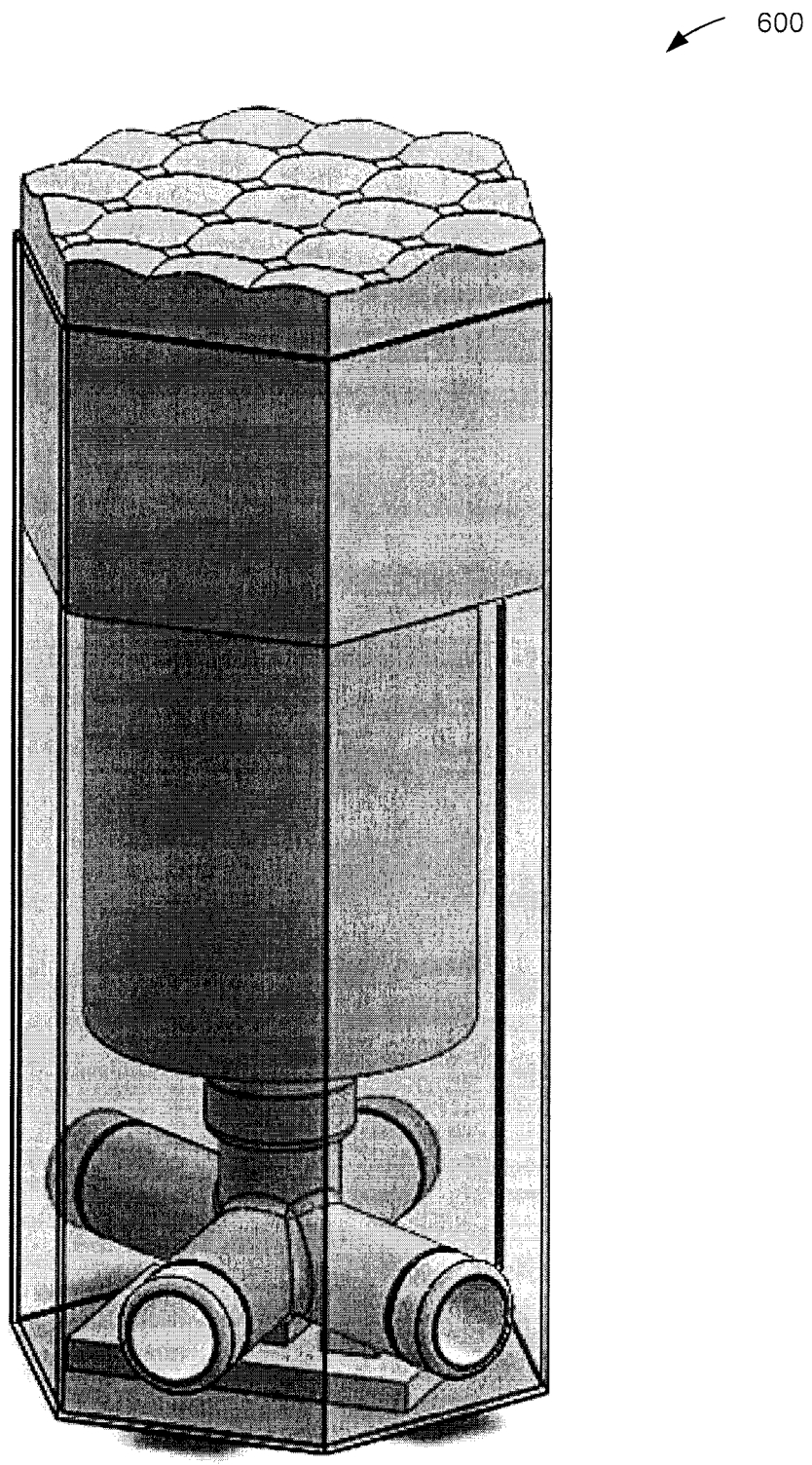
FIG. 6 is a rendering of an isometric view of a valve multiplier, according to some embodiments.

Referring to FIGS. 5 and 6, there is provided an isometric view of components of a valve multiplier system according to some embodiments. In some embodiments valve multiplier may be an active component that may function to distribute airflow from at least one inlet (e.g., inlet 408) to multiple outlets (e.g., outlets 204) according to specific rotational movements controlled by a single motor rotatably coupled to valve multiplier via a motor mount 506.

In some embodiments, motor may align the two discs 504, 502 (e.g., the bottom portion and top portion) of the multiplier to open a direct line between at least one air cell 516 and a pressure pump. A control system may issue electronic instructions which may cause motor to rotate a motor arm to a specific degree—said motor arm coupled to motor aperture 506 may cause multiplier to enter a specific alignment which may enable air from pressure pump to flow through certain of valve multiplier's inlets and outlets in order to fill specific air cells 516A-C. This may include messaging at least one specific degree turn to the motor coupled to the multiplier. This design may allow for a low profile design, and reduce component costs of the system by enabling the control of multiple air cells 516A-C from a single motor.

In some embodiments, top disc 502 may comprise a single inlet and multiple outlets around the perimeter of the disc shaped body. A centrally located hole (508) may be used to pass a motor shaft to the bottom disc 504.

In some embodiments, motor mount may enable connection of at least one motor (e.g., a stepper motor) to the valve multiplier. Attachment of a motor shaft to bottom disc 504 may enable rotational control of the multiplier.

In some embodiments, bottom disc 504 may contain at least one circular groove with at least one single protruding groove. This circular groove may be along a path that does not intersect with path top disc 502 outlets (e.g. 402). The top disc 402 may possess at least one inlet that may be positioned above the circular groove in order to maintain constant airflow to the groove. When motor is activated the protruding grove (e.g., 306) may be rotated to align with the desired outlet (e.g. 402).

In some embodiments, at least one 3-way valve 508 may be included, which may have a solenoid to control flow between 3 lines. The 3-way valve may be used to control which manifold 510A-B is supplying air to the multiplier.

In some embodiments, a number of manifolds 510A-B may be included in order to multiplex lines openly from pressure pump. Check valves may be used within the manifold or in the tube connecting the manifold to the multiplier in order to limit flow of air to a single direction. Manifolds 510A-B may be connected to a flow source such as a pressure pump and/or vacuum.

In some embodiments, this design may lead to slowed transmission of air pressure to individual air cells 516A-C. Optimization may be critical for the valve multiplier to work effectively and seamlessly. Leveraging last mile optimization algorithms in conjunction with sensor and user feedback, the most optimal pressure regulation pattern may be determined. This optimal pressure regulation pattern may be interpreted into commands for the stepper motor to execute the appropriate turns at the right times. Reinforcement learning modeling may allow for custom, optimized configurations of pressure relief valves by optimizing multipliers based on user specific performance feedback to models.

Figure 7:
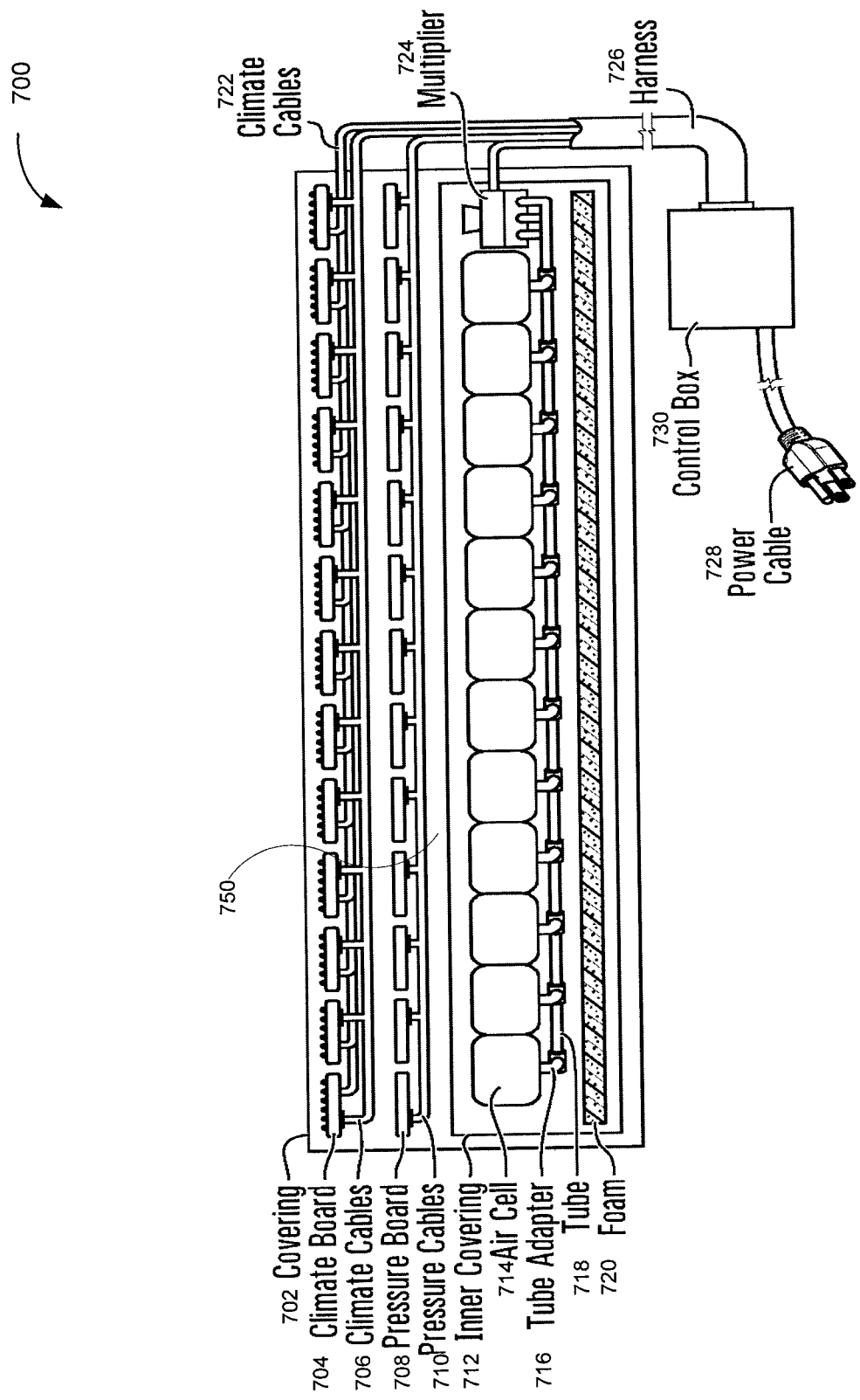
FIG. 7 is a block diagram depicting cross-sectional side view of components of a pressure injury management system, according to some embodiments.

Referring to FIG. 7, there is provided a block diagram depicting a cross-sectional side view of components of a pressure injury management system, according to some embodiments. A covering 702 may be included. In some embodiments it may be critical to the proper function of the system 100 that a suitable covering 702 is used which interfaces between the system 100 and external environment. It may be necessary that covering 702 be permeable to water vapour and that covering 702 is low profile in order to prevent distortion of pressure and temperature readings recorded by the components of the pressure sensing layer (e.g., 708-710) and climate sensing layer (e.g., 702-704, 722, or see 2724 in FIGS. 27A, 27B and 27C). Another major constraint to choice of construction materials for the covering 702 may be that such materials may need to be waterproof in order to prevent fluids from entering system 100. In a non-limiting example, Polytetrafluoroethylene fabric membranes may be used to meet these requirements, and may allow for proper measurement of environmental signals from the climate sensing layer (e.g., 702-704, 722, or see 2724 in FIGS. 27A, 27B and 27C) and pressure signals from the pressure sensing layer (e.g., 708-710, or see 2726 in FIGS. 27A, 27B and 27C) while protecting the system 100 from damage due to contact between fluid and electronic components.

In some embodiments, climate board 704 and climate cables 722 may be beneath covering 702. Climate board 704 may comprise a plurality of climate sensors (e.g., see FIGS. 27A, 27B and 27C, 2724). These components may facilitate the measurement and monitoring of various characteristics of the body of a user. These characteristics may include the temperature and the humidity of the user's body. In order to accomplish this climate sensors in climate board 704 may be connected to a microcontroller via climate cables 706, 722 (e.g., a climate microcontroller (climate MCU) FIGS. 27A, 27B and 27CC, 2756), and may transmit and receive data from such microcontroller using a digital data transfer protocol.

In some embodiments, pressure board 708 and pressure cables 710 may be positioned beneath climate board 704 and climate cables 706, 722. Pressure board 708 and pressure cables 710 may be components of a pressure sensing layer (see FIGS. 27A, 27B and 27C, 2726) and may contain a plurality of sensors which may produce data used by system 100 to measure and monitor user's position, evaluate data to indicate patient comfort level, identify various points on user's body at risk of suffering pressure injuries(e.g., risk areas), identify if pressure is being, or has been, exerted upon risk areas, measure user's position for various wellness purposes among other applications (e.g., sleep monitoring, injury monitoring).

In some embodiments, pressure sensing layer 2726 may be suitable for use for product development in health & wellness industries for bedding or seating applications. Non-limiting examples may include: measuring and monitoring user position; evaluating patient comfort; identifying pressure on risk areas; measuring user's position for wellness purposes (e.g., sleep monitoring); and other applications.

In some embodiments, a pressure mitigation layer 750 may be positioned beneath pressure cables 710 and may mitigation the movement of air cells 714 in relation to the movement of a user. This may allow for distribution of pressure exerted on certain body areas of the user with minimal movement of the user and/or the components of system 100.

In some embodiments, one or more air cells 714 may be included. Each air cell may contain one or more pressure sensors used to detect the air pressure within the air cell 714. In some embodiments, a plurality of air cells 714 may be provided. Air cells 714 may form part of a pressure relief system (e.g., see FIGS. 27A, 27B and 27C, 2702) to redistribute pressure according to the generated pressure redistribution plan, and may, in an non-limiting example, take the form of a plurality of cubed Polyvinyl chloride (PVC) unit with a tube adaptor 716 connected to the air cell 714 via at least one tubing 718 which may supply airflow (e.g., through one or more air pumps and one or more multipliers 724). Air cell 704 may be a is a basic unit of the construction of sensor mat present disclosure, and may function to redistribute pressure exerted between the various parts of user's body and covering 702 in response to various sensor data (e.g., pressure, temperature, wetness, etc.) captured and processed by system 100. In some embodiments, multiplier 724 may function to distribute airflow from a single inlet (e.g., an air-intake connected to an air pump via a tube) to multiple outlets which may be connected to air cells 714 (said inlet and outlets forming part of multiplier 724).

Figure 8:
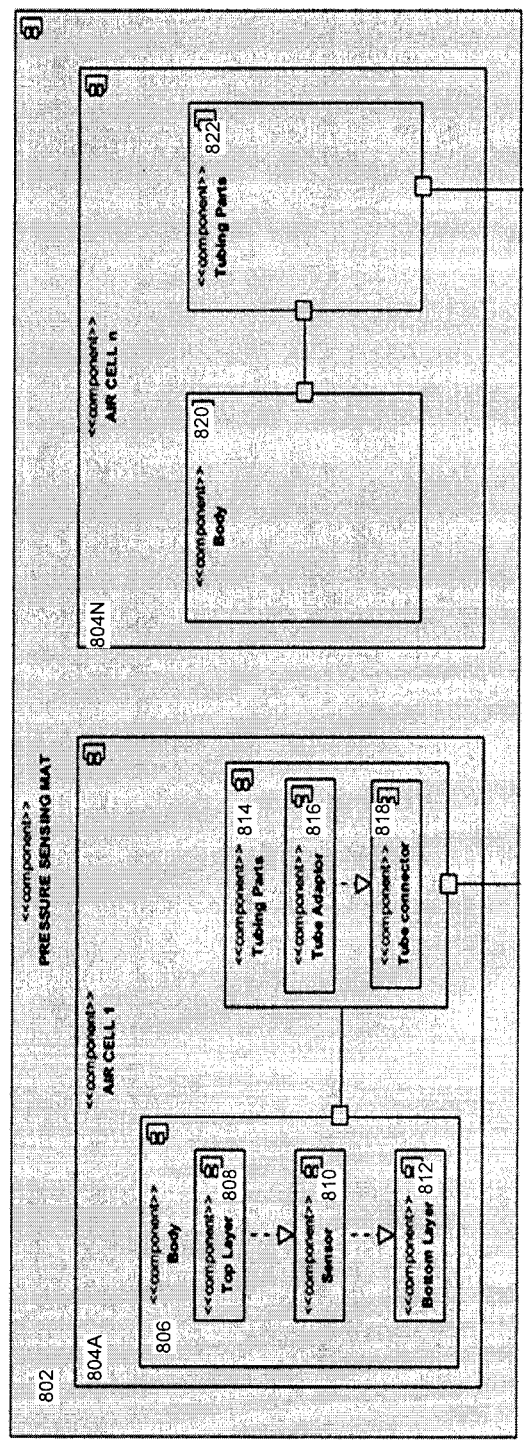
FIG. 8 is a block diagram showing components of a pressure sensing layer, according to some embodiments.

Referring to FIG. 8, there is provided a block diagram showing components of a pressure sensing layer, according to some embodiments. A top layer 808 may be included. In some embodiments it may be critical to the proper function of the system that a suitable covering is used for top layer 808 which interfaces between the system and external environment. It may be necessary that top layer 808 be permeable to water vapour and that top layer 808 is low profile in order to prevent distortion of pressure and temperature readings recorded by the components of the pressure sensing mat 802 (e.g., air cell 804A, sensor 810) and climate sensing layer (e.g., see 2724 in FIGS. 27A, 27B and 27C). Another major constraint to choice of construction materials for the top layer 808 may be that such materials may need to be waterproof in order to prevent fluids from entering the system. In a non-limiting example, Polytetrafluoroethylene fabric membranes may be used to meet these requirements, and may allow for proper measurement of environmental signals from the climate sensing layer (e.g., see 2724 in FIGS. 27A, 27B and 27C) and pressure signals from the pressure sensing layer (e.g., 708-710, or see 2726 in FIGS. 27A, 27B and 27C) while protecting the system from damage due to contact between fluid and electronic components.

Figure 9:
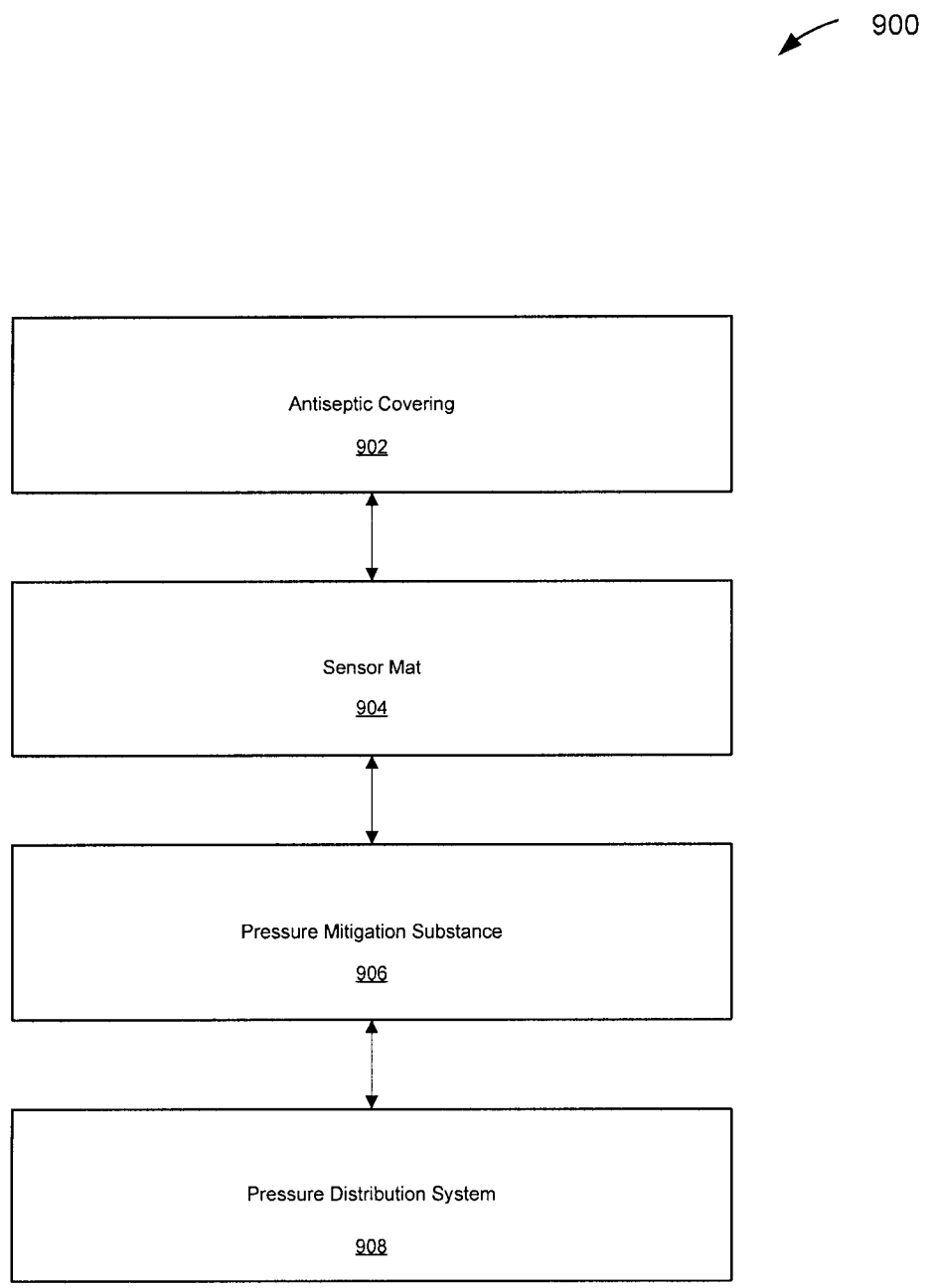
FIG. 9 is a block diagram showing components of a mattress implementation of a pressure injury management system, according to some embodiments.
Figure 11:
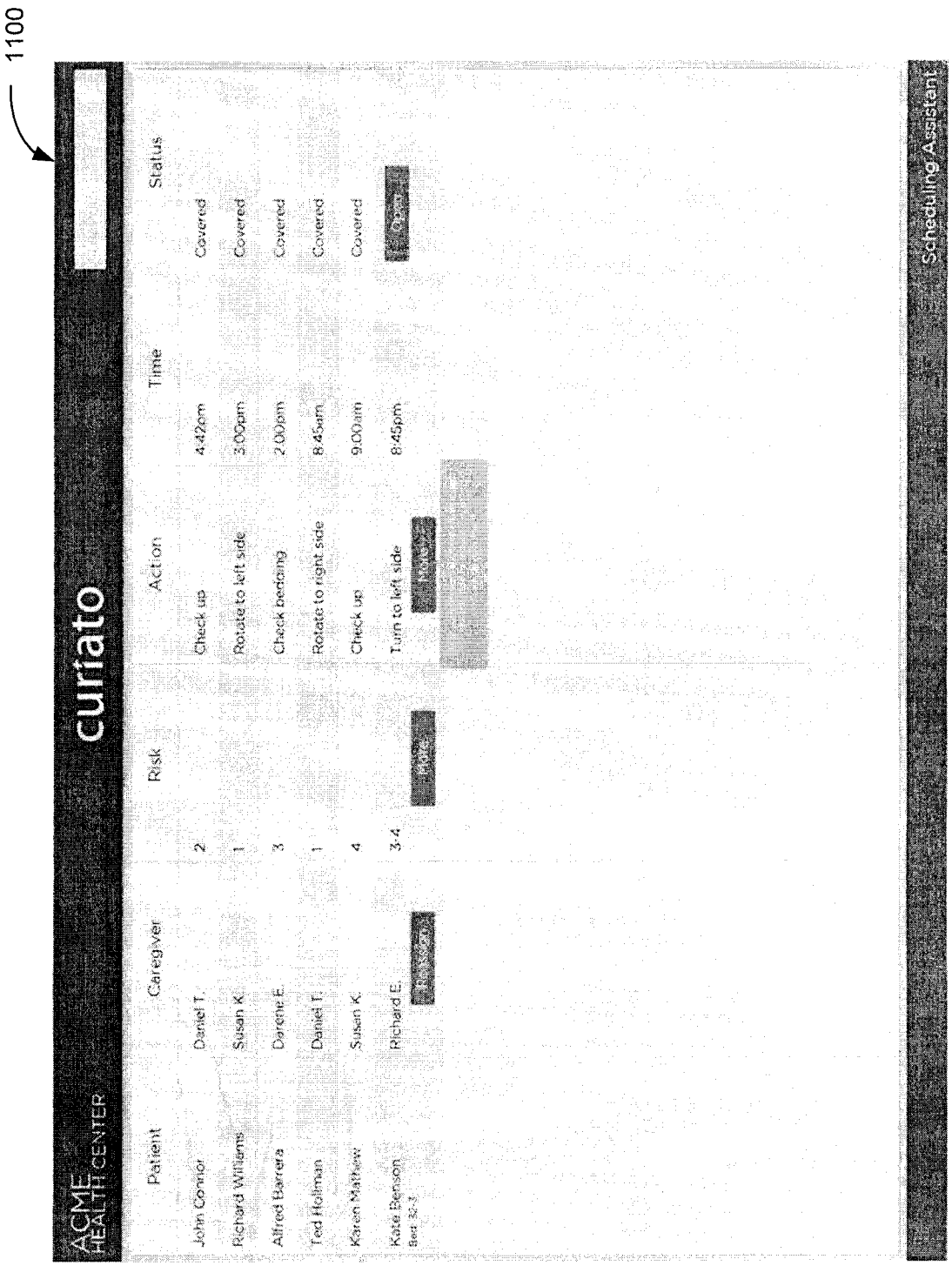
FIG. 11 depicts an example scheduling user interface, according to some embodiments.

Referring to FIG. 9, there is provided a block diagram showing a broad overview of elements of a mattress implementation of a pressure injury management system, according to some embodiments. This example implementation includes a top surface with an antiseptic covering 902, which a user may lie atop. This antiseptic covering may help ensure that foreign substances (e.g., bodily fluids) to not enter the depicted implementation 900 of the present disclosure. A sensor mat 904 containing various sensors (e.g., pressure sensors and climate sensors) may be placed beneath the antiseptic covering 902. Sensor mat 904 may detect various properties of user (e.g., pressure exerted by various parts of user's body upon antiseptic covering 902 and then upon various sensors in sensor mat 904, humidity, temperature, etc.), and may cause data representing said detected properties to be transmitted to one or more computing means for processing. Components within sensor mat 904 may also receive instructions from computing means, which instructions may alter the function of the sensors within sensor mat 904. A pressure mitigation substance 906 may be placed beneath sensor mat 904 and above pressure distribution system 908. Pressure mitigation substance may function to dampen forces produced by pressure distribution system upon the body of the user, and vice versa. A pressure distribution system 908 may be included beneath pressure mitigation substance 906. Pressure distribution system 908 may employ various pressure creation or reduction means to increase or reduce pressure exerted upon various body parts of the user atop of antiseptic covering 902.

Referring to FIG. 10A, a plan view of the top layer configuration of an air cell mat is provided, according to some embodiments. The non-limiting example embodiment depicts the top layer of an air cell mat 1002a comprising sixty-four air cells (1004a, 1004b, 1004c, etc.). The black squares depicted within each of the air cells (1004a, 1004b, 1004c, etc.) demonstrates the concave top portion of each air cell (1004a, 1004b, 1004c, etc.) according to an embodiment. The concave portion may be produced through thermoforming. The vertical and horizontal gridlines may represent radio frequency welding (RF welding) lines (1008a, 1008b, 1008c, etc.) between air cells (1004a, 1004b, 1004c). RF welding (also known as High Frequency (HF) welding or Dielectric welding) may be a method of joining thin sheets of polar thermoplastic materials.

Referring now to FIG. 10B, a non-limiting example plan view of an bottom layer FPCB configuration 1002b of an air cell mat may be provided, according to some embodiments. Each circular portion depicted may represent the location of tube connector (1010a, 1010b, 1010c, etc.). The oval shaped portions may represent the location of the sensor dip pins (1012a, 1012b, 1012c, etc.), which may connect to one or more FPCBs.

Referring now to FIG. 10C, a non-limiting example plan view of an FPCB configuration 1002c for a climate sensor layer may be provided, according to some embodiments. The example may depict the configuration of an FPCB for a climate sensor layer situated in between pressure sensor air cells (e.g., 1004a, 1004b, 1004c, etc.) in order to allow for mappable configuration of both layers (e.g., the climate sensor layer and the pressure sensor layer.

Referring now to FIG. 10D, a non-limiting example a plan view of an FPCB configuration 1002d for pressure air cells situated underneath a pressure sensing layer may be provided. As depicted, each FPCB may underlay four pressure dip pins in order to provide a secure, flexible connection between the air cell sensor and communication system.

Figures 3, 14:
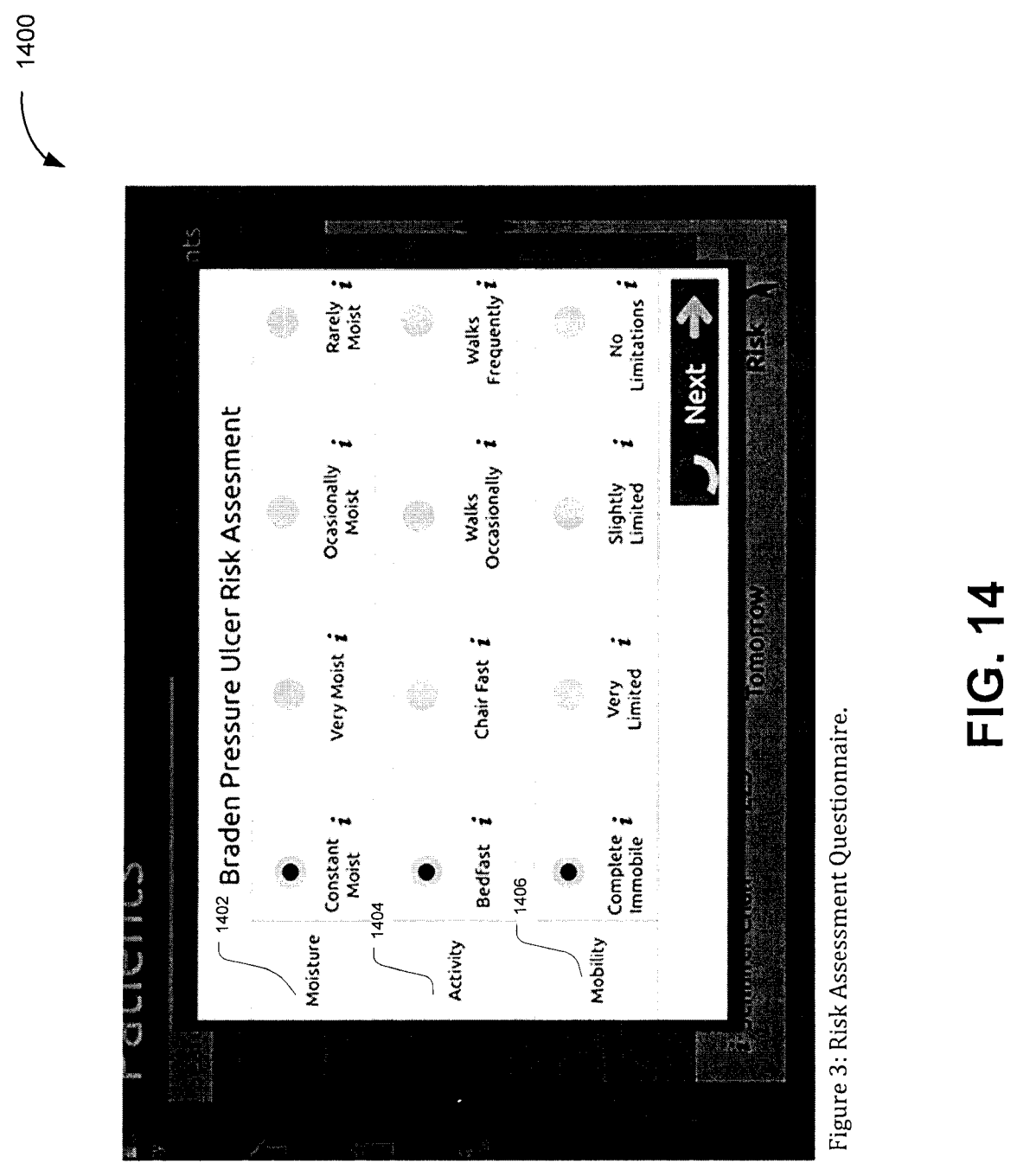

Referring to FIG. 14, there is provided an illustration of an example scheduling user interface, according to some embodiments.

Figure 15:
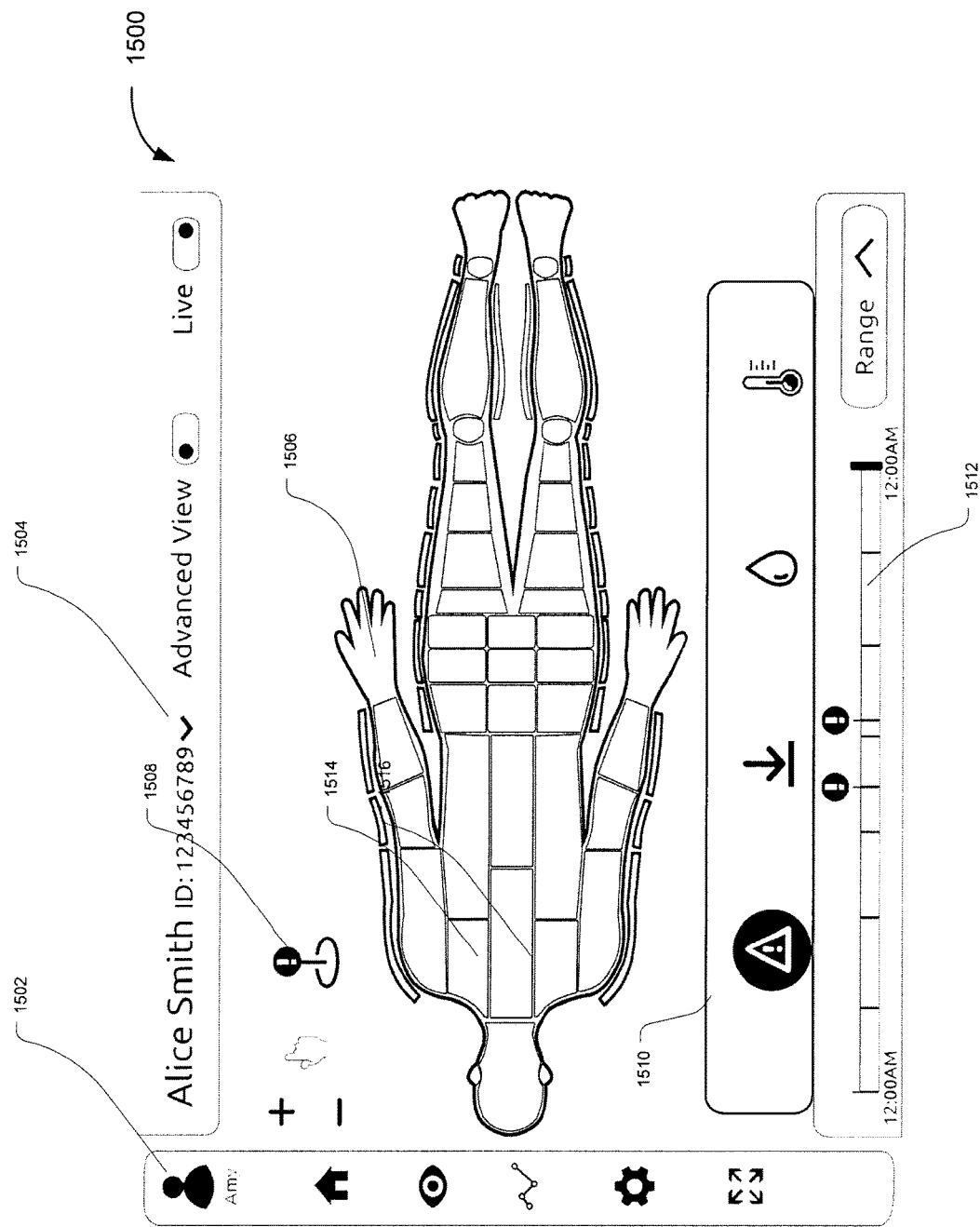
FIG. 15 depicts an example risk notification user interface, according to some embodiments.
Figure 16:
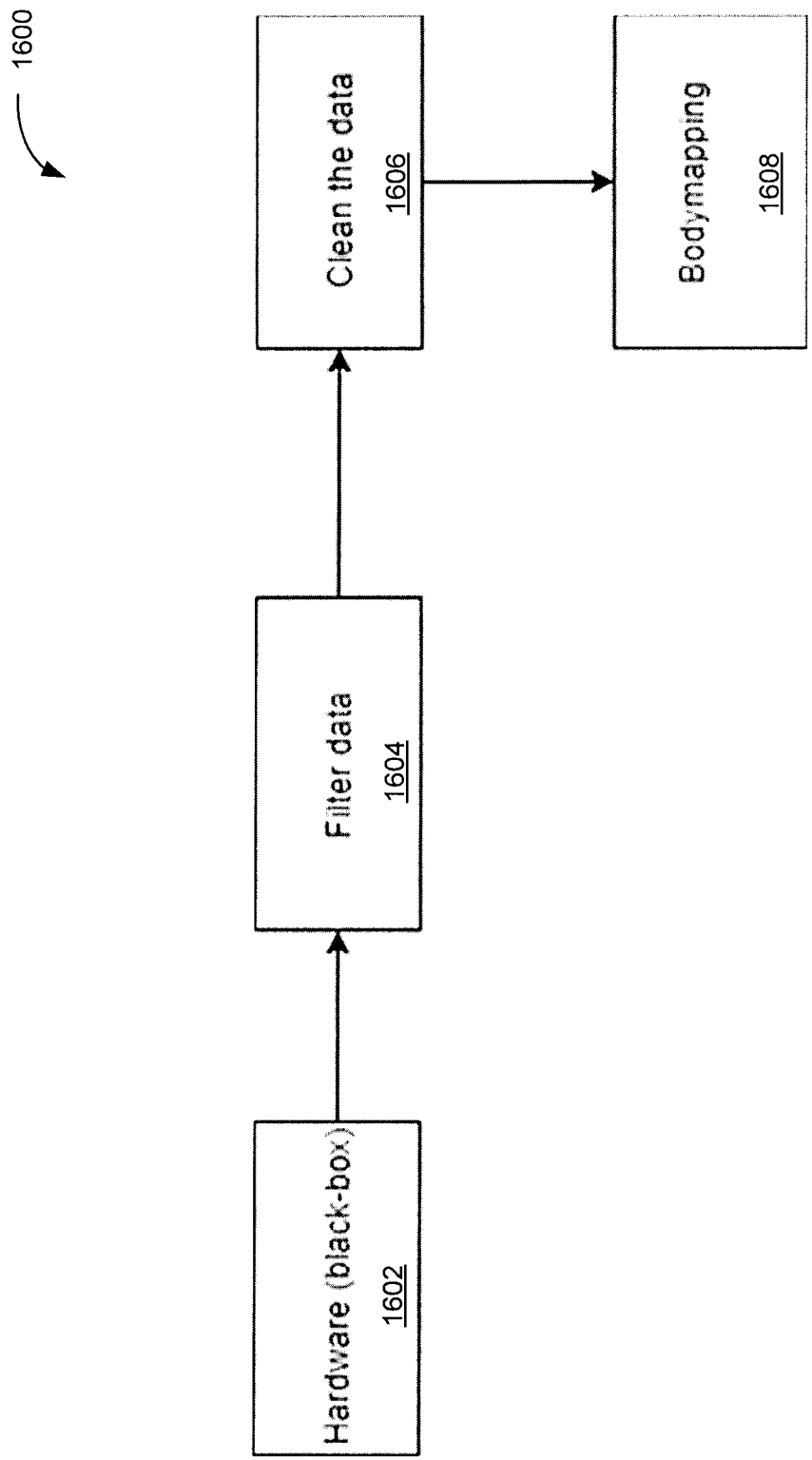
FIG. 16 is a block diagram depicting an overview of a data collection and processing method from sensor data collection to risk map creation, according to some embodiments.

Referring to FIG. 15, there is provided an illustration of an example patient information user interface, according to some embodiments Referring to FIG. 16, there is provided a block diagram depicting example method a data collection and processing sensor data collection to risk map creation, according to some embodiments. According to some embodiments, various software and hardware elements described herein may work in tandem provide a solution which may to help prevent pressure injuries. The example embodiment depicted in FIG. 16 comprises four main components to its software element: 1. scheduling; 2. visualization; 3. data analytics; and 4 risk mapping and/or pressure redistribution.

In an example embodiment, once the hardware components of the system 100 (e.g., hardware 1602) of the present disclosure have collected various sensor data and transmitted it to computing means, the received data may be filtered. "Clean" data 1606 may be free from unrequired or inappropriate values and may be crucial to achieve beneficial data analytics and subsequent actions. The first step in cleaning received data may be to filter it 1604.

In some embodiments, handshaking between the hardware 1604 and software may first be necessary in order to accomplish filtering 1604 of data. Handshaking is a term used to describe two-way communication between a computer (e.g., an onboard computer) and various components of the hardware 1602. Two-way communication may be necessary to: a) allow a computer to receive the data for data analytics purposes; b) request any necessary data (e.g., direct sensors forming part of hardware 1602 to record values); and c) to control various elements of the hardware 1602 (e.g., to inflate/deflate specific air cells in order to provide targeted pressure relief at specific areas of the body of a user).

In some embodiments, filtering 1604 may commence by first transferring data from the one or more sensors (e.g., pressure sensors in a pressure sensing layer) forming part of hardware 1602 (e.g., mattress incorporating the present disclosure) to a computer and aggregating all received data points in a memory of said computer. Next, computer may process the data points and may identify the one or more data points where there is no pressure exhibited (e.g., where a "zero" value was received from a sensor). As the data may be received sequentially, and in the same order, every time, the computer may be able to create a risk grid model and associate each sensor with a coordinate thereupon. It may be important to identify where there is no received pressure data as such values may reflect that there is no limb present at a certain area (e.g., upon a certain area of a mattress). This, then, may help to identify which other sensor values (e.g., humidity and temperature sensor values) need to be read (e.g., other sensor values corresponding sensors at risk grid coordinates where no data was received from pressure sensors may not be processed). This may also optimize the operation of software elements of the present disclosure.

In some embodiments, after reading the pressure sensors, the onboard computer may proceed to request humidity and temperature sensor values at coordinates where pressure data not equaling zero or null was present. This may be a second handshaking step. By receiving other sensor values (e.g., humidity and temperature values) according to data received by pressure sensors, the system may maintains alignment between the sensor metrics (in terms of locations), which may be necessary to complete proper data processing and limb recognition steps. After the data for all sensor metrics has been aggregated, cleaning the data 1606 and increasing the resolution thereof may occur.

In some embodiments, due to the current state of sensor and/or computer technology, certain optimizations and/or re-prioritizations may be necessary to provide more economical embodiments of the present disclosure. An example re-prioritization may affect the software processes described herein: relying solely on sensor data and locations may take visualization resolution only so far. As a non-limiting example, if one were to create a square grid based on the locations and sensor data received, alone, then the resolution may, depending on the number of sensors, be quite poor. In order to improve resolution, embodiments of the present disclosure may employ k-nearest neighbors (KNN) clustering non-parametric classification and regression techniques in order to infer the values in the spaces of the sensor array to provide a high resolution and accurate visualization. KNN clustering works by taking into account the known neighbouring values at a particular point and averaging those values to infer what the value at that point will be.

In some embodiments, in addition to increasing the resolution of visualization, KNN clustering may also be used to infer values for sensors that may have malfunctioned and returned NaN (not a number) or out-of-range values. When a sensor malfunctions, it may typically produce either a NaN value or a value that is wildly out of range (e.g., either an extreme positive or negative number). In either case, these values cannot be sent to the data analysis and processing stage as they may negatively impact the accuracy of predictive machine learning models. Therefore, KNN clustering may be used to infer probable values and send clean data to the data analytics engine.

In some embodiments, after data has been cleaned, the next step may be bodymapping 1608. Bodymapping 1608 may begin by segmenting sensor data according to body areas (e.g., limbs), which may aid in the production of better outputs and, thus, better and more accurate care. For example, the body may be segmented into a number of sections (e.g., 8 sections comprising: head, abdomen, left and right arms, left and right legs, and the two heels). The array of sensors (e.g., see FIG. 2) may be defined by which region or regions of the array of sensors is most likely to receive data from a section of the body. As a non-limiting example, the top 4 in.×10 in. in the middle section. An example process of achieving bodymapping 1608 may include the following steps (depicted in detail in FIG. 28):

Having the patient lie down on the mattress for 30 seconds to calibrate the sensors;

Creating an initial visualization based on the sensor locations, and displaying initial limb mapping (the limb mapping may be done by processing both the sensor locations and by historical data);

Obtaining historical data by a data clustering and Convolution Neural Network process, wherein past data is referenced to identify the probability of these being the correct limbs and actually being limbs (instead of another object being placed on the mattress);

Prompting a nurse or other operator to accept or reject the limb segmentation—this may be done for two reasons: first, to maintain accuracy when the segmented data is sent to the analytics engine; second, to train the system by outlining values in existing data corresponding to correct limb segmentation;

If the nurse says yes, then the proceeding to send data to the cloud for processing;

If the nurse says no, then the nurse can identify on the heat map (e.g., via a user interface—see FIGS. 12, 15) where the limbs are, and this identification is sent along with the data to train the models on recognizing limbs correctly.

When the data is sent to the database, data for each limb may be included in separate tables. This may be crucial to allow the data clustering to provide better analytics and recommended actions regarding specific limb areas. This improvement in the function of data analytics may be a result of aggregating historical data on specific limbs and then running analyses specific to each limb.

In some embodiments, after bodymapping 1608 is complete, the next step may be for machine learning and artificial intelligence models to process and analyze the data in order to produce an instruction set which may include instructions inflate and/or deflate certain air cells associated with certain limbs or body areas.

Figure 17:
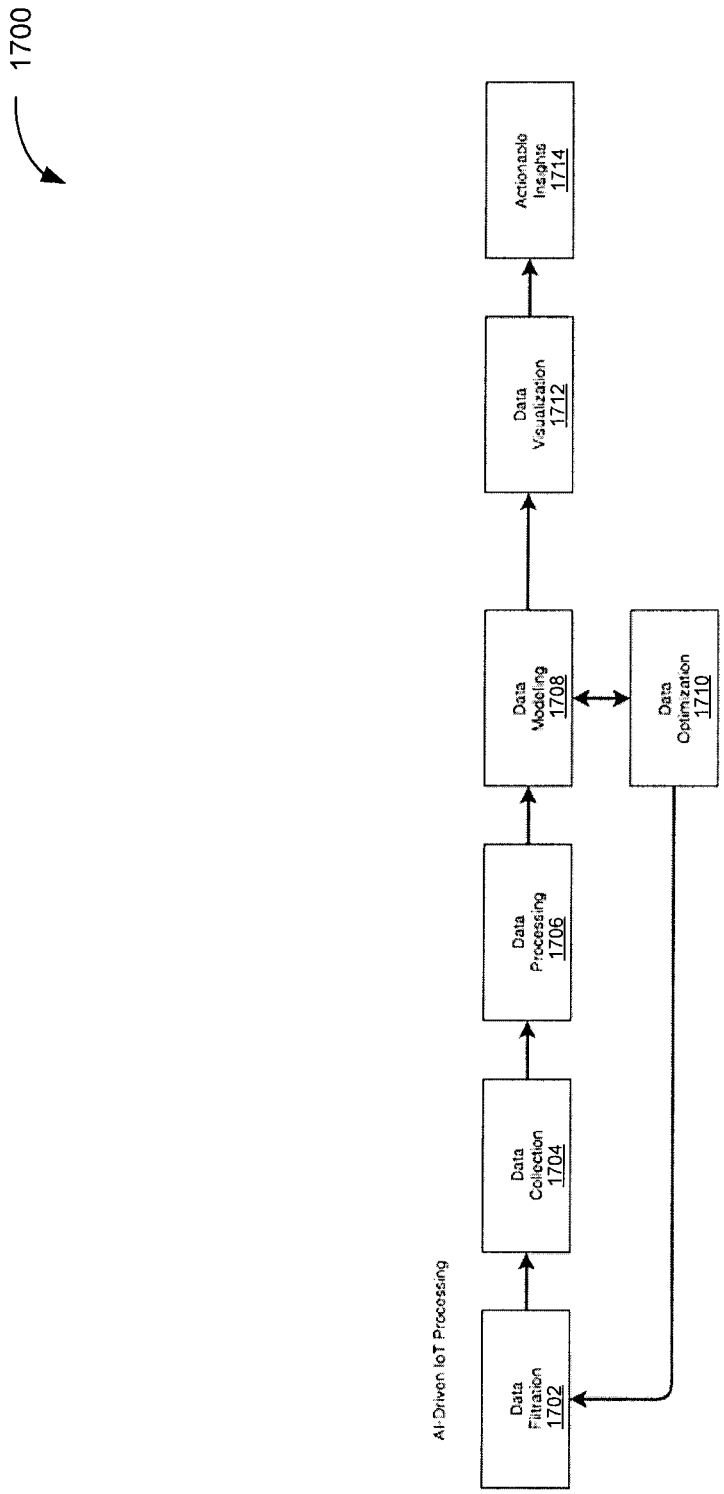
FIG. 17 is a block diagram depicting an artificial intelligence driven processing method, according to some embodiments.

Referring to FIG. 17, there is provided a block diagram depicting an artificial intelligence driven processing method (AI model), according to some embodiments. The example process may serve to provide outcome based notifications and monitoring using spatial and temporal dependent mapping of sensor data through Artificial Intelligence.

In some embodiments, a data filtration 1702 process which may filter AI model insignificant data (e.g., data that is not required for the function of the AI model) by determination of interdependent data and one or more spatial relationships between interdependent factors. One or more filtration algorithms may be derived (e.g., through reinforcement learning processes) and extracted to the beginning of a data processing pipeline.

In some embodiments, at 1704 a data collection process may connect or adopt one or more types of data stream (e.g., sensor, video, audio, user-inputted, historical, etc.) through an API or via a sensor multiplexing node (i.e. a decoder embedded architecture that allows for unlimited scaling of connected sensors without significant loss of performance or reliability) and may recording said data in a memory with references to a system, subject or object.

In some embodiments, at 1706 data processing may occur. Data processing 1706 may include multiple steps in sequence (e.g. filtration→storing raw data→processing data for cleaning→spatially orienting data→streaming data). One or more of the steps in data modeling may cause certain processed data to be returned to data filtration 1702. For example, spatially and temporally oriented data may be returned to data filtration in order to produce a more optimized data set for processing.

In some embodiments, data wrangling (e.g., transforming and mapping data from one "raw" data form into another format with the intent of making it more appropriate and valuable for a variety of downstream purposes such as analytics) may include high tolerance (in some cases this may be full tolerance) in cases of malfunction of hardware. In such cases, AI model may subsidize data imputation. As a non-limiting example, imputation may include, in the event some data is missing, applying KNN clustering, enhance resolution and measuring average and neighborhood values where K is equal to the number of neighbours.

In some embodiments, the present disclosure may be implemented by a sensor mat that may be flexible enough to be adjusted to fit a multitude of spaces—the software elements of the present disclosure may function to produce its own coordinate grid and limb mapping in response to received data (intelligent coordination).

In some embodiments, intelligent coordination may provide mapping of regions of a sensor mat incorporating the present disclosure by the following process:

Step 1: Cluster (K mean) the entity according to general characteristics (segment the body). Clustering sensor mat according to general body segments in order to cause sensor collecting data related to one or more limbs to be recognized as representing location of said limb.

Step 2: Capture sensor to relevant segment sensor and apply AI (KNN) to map. KNN confirms that read sensor data is at the location, Step 3: Confirmation of the limb location by processing a cluster of body location values and pressure values of pressure sensors. Get a double confirmation.

In some embodiments, sensor location may be mapped to body segment or limb location by the following process:

Apply Machine learning by phases: cluster mattress into segments, each segment represents general body location; applying AI (KNN) to map every sensor to body segment or limb without overlapping or interfering with other clusters. This may increase resolution.

Use pressure as an indicator to accurately map body segments to sensors.

End data: sensor ID, xyz coordinate data, time data, and readings may be written to a memory.

In some embodiments, data modeling 1708 may run a multi-agent, multi-model process combining current most accurate model and new data stream (MAMM) combinations, leveraging transfer knowledge. This may include ranking or weighing outputs to determine the most reliable model in a given application. Next the model may be applied in order to spatially map values 1712 recorded during time period.

In some embodiments, data models may be built based on two types of data: historical data (user profile, EMR), and real-time (e.g., data collected by from sensors rather than read from a historical database) data. Historical models may compare to data received from sensors recording values produced by a user as a baseline to reinforce the model. However, important features (e.g., features that most often return reliable values) of the model may always be kept as the most reliable influencer of the model. As new models are created, certain values therein may be averaged and the highest weighted model by accuracy may be kept. Learning models may be kept based on the accuracy of predictions produced therefrom.

In some embodiments, before a new model is built (e.g., as 1710 returns to 1702), features that will yield high accuracy are retained, by keeping these features the model will not likely lose accuracy. Adequate data to perform a feature detection and selection step may be required. If there is not adequate data to detect features, the model may not adopt a new model.

In some embodiments, one or more data visualizations 1712 of layered outputs and inputs of the model may be oriented spatially and temporally, associated with the user (e.g., patient) and may be displayed. Visualizations can be displayed through a variety of interfaces including but not limited to mobile devices, web-based user interfaces, wearables, mobile device alerts, etc.

In some embodiments, though the AI model may predict and recommend certain actions regarding optimal redistribution (e.g., a redistribution plan) of a patient, operators (e.g., nurses) may be required/allowed make the final decision. To this end, real-time visual representations of limb location sensors may be provided.

Figure 12:
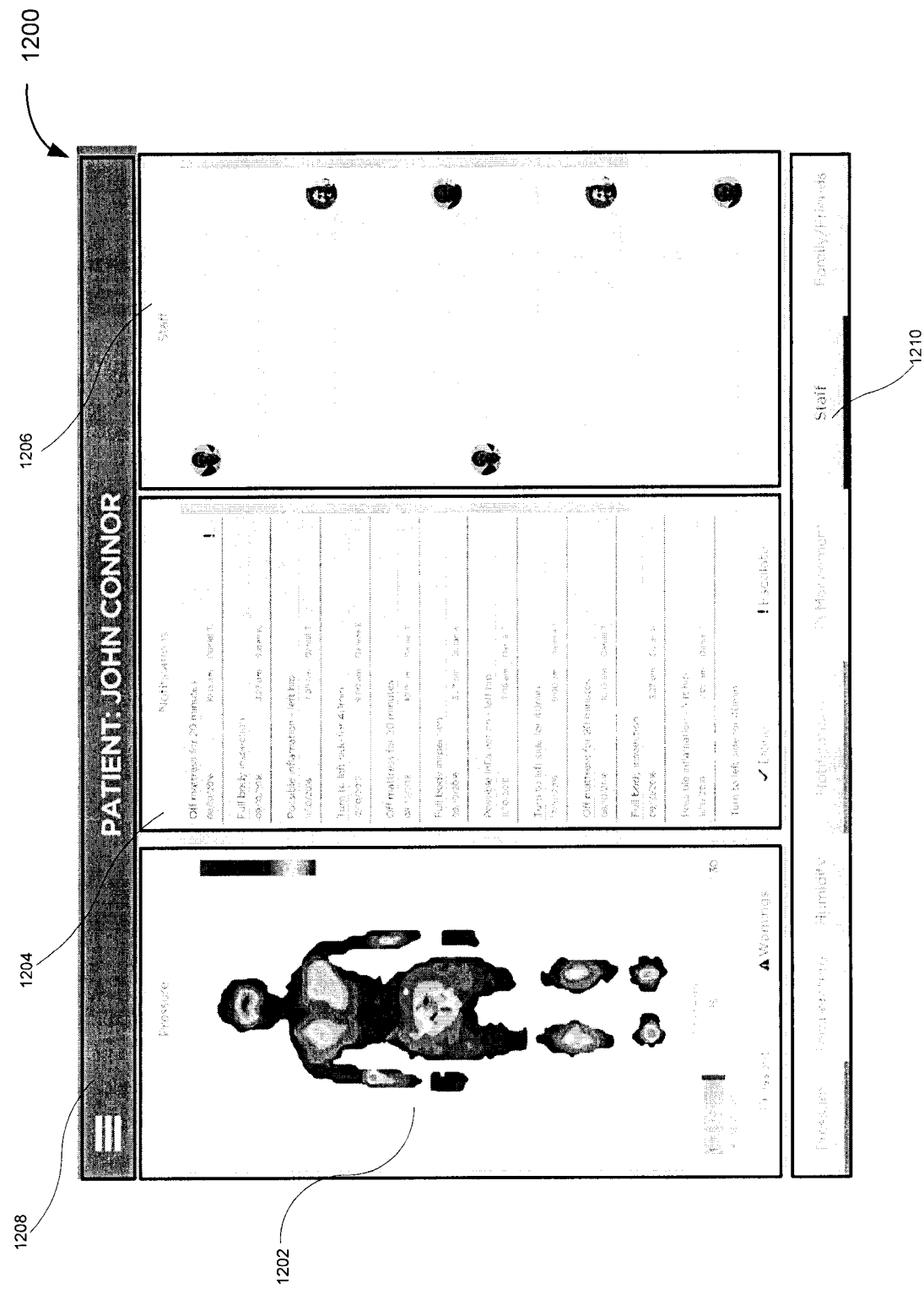
FIG. 12 depicts an example patient information user interface, according to some embodiments.
Figure 13:
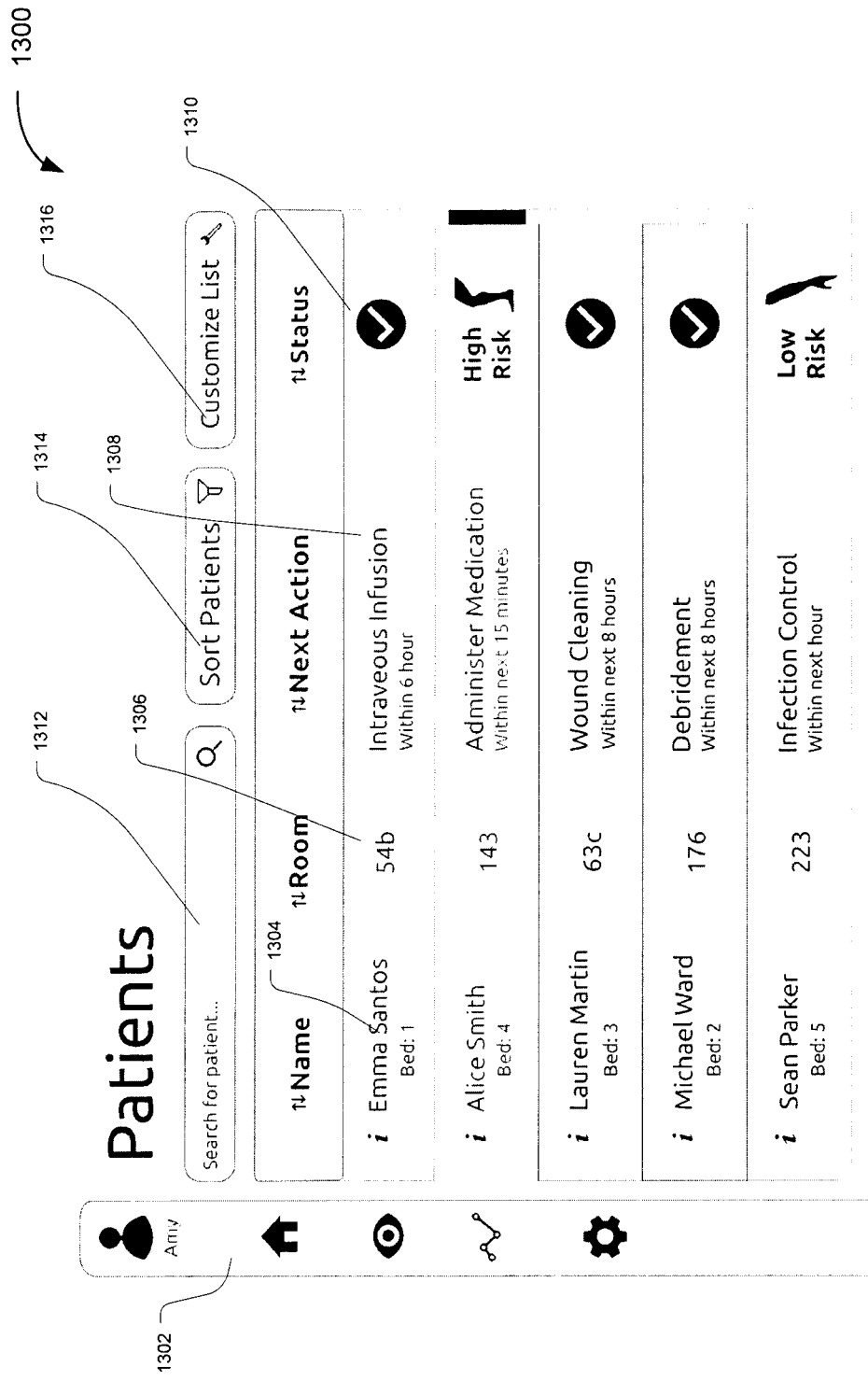
FIG. 13 depicts an example patient manager user interface, according to some embodiments.

In some embodiments, at 1714, actionable insights may be provided, and may take the form of time-based notifications that are spatially overlaid atop an outcome risk-map (see e.g., FIGS. 12, 15. This may allow for operator (e.g., doctor) validation of redistribution recommendations in the redistribution plan produced by the present disclosure. Time-based notifications may allow for actionable insights by user leveraging business process modeling engines to allow operators to easily customize when notifications are to be sent/received.

Customization can take the form of, but is not limited to, intelligent thresholds, if-statements, signals, etc., and customization may allow for incorporation of actions into the workflow of a specific user. Eventually AI model may allow for autonomous use (e.g., when recommendations produced therefrom passes a certain performance metric).

Figure 18:
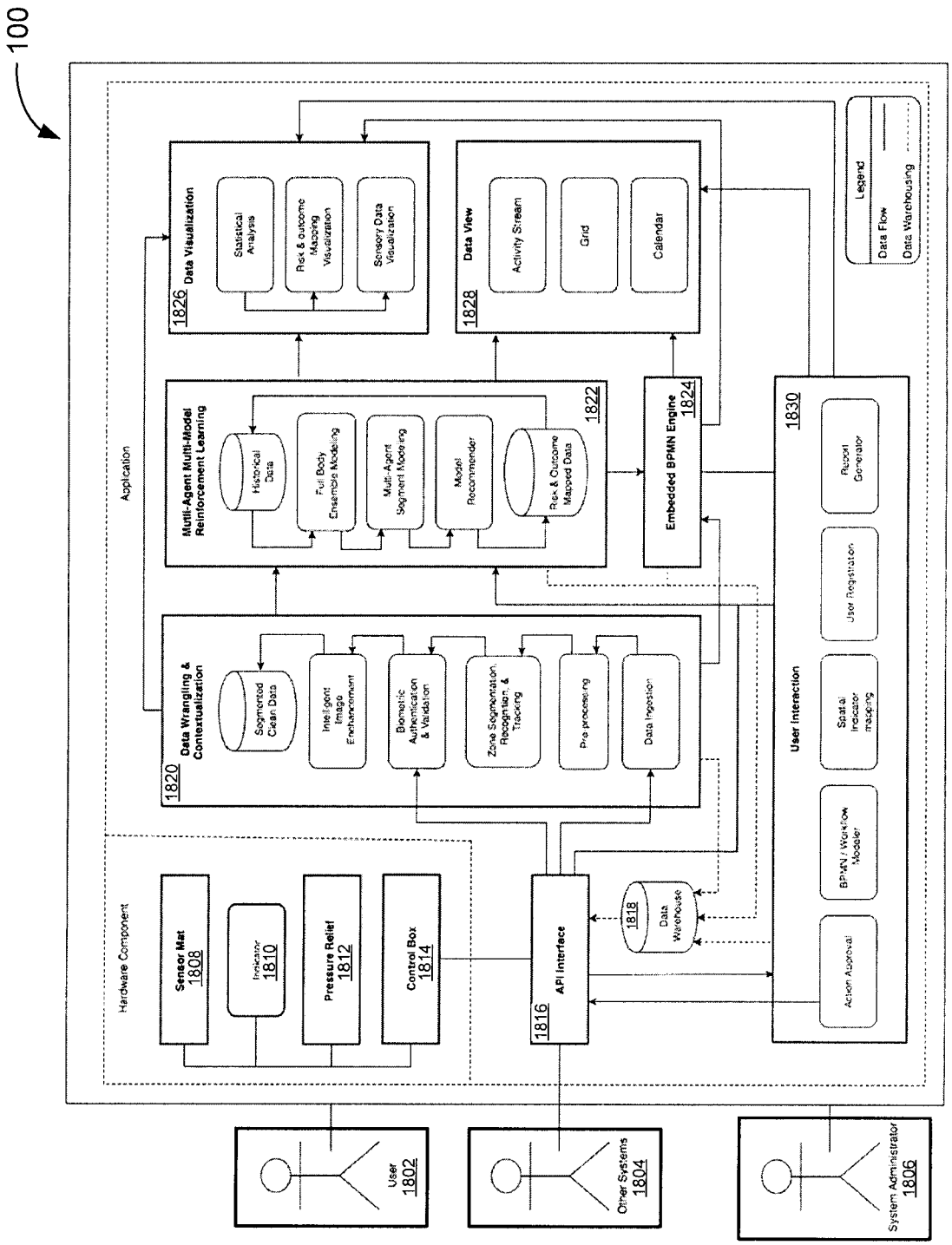
FIG. 18 is a flow-chart of a method of facilitating communication between hardware and software components of a pressure injury management system, according to some embodiments.
Figure 19:
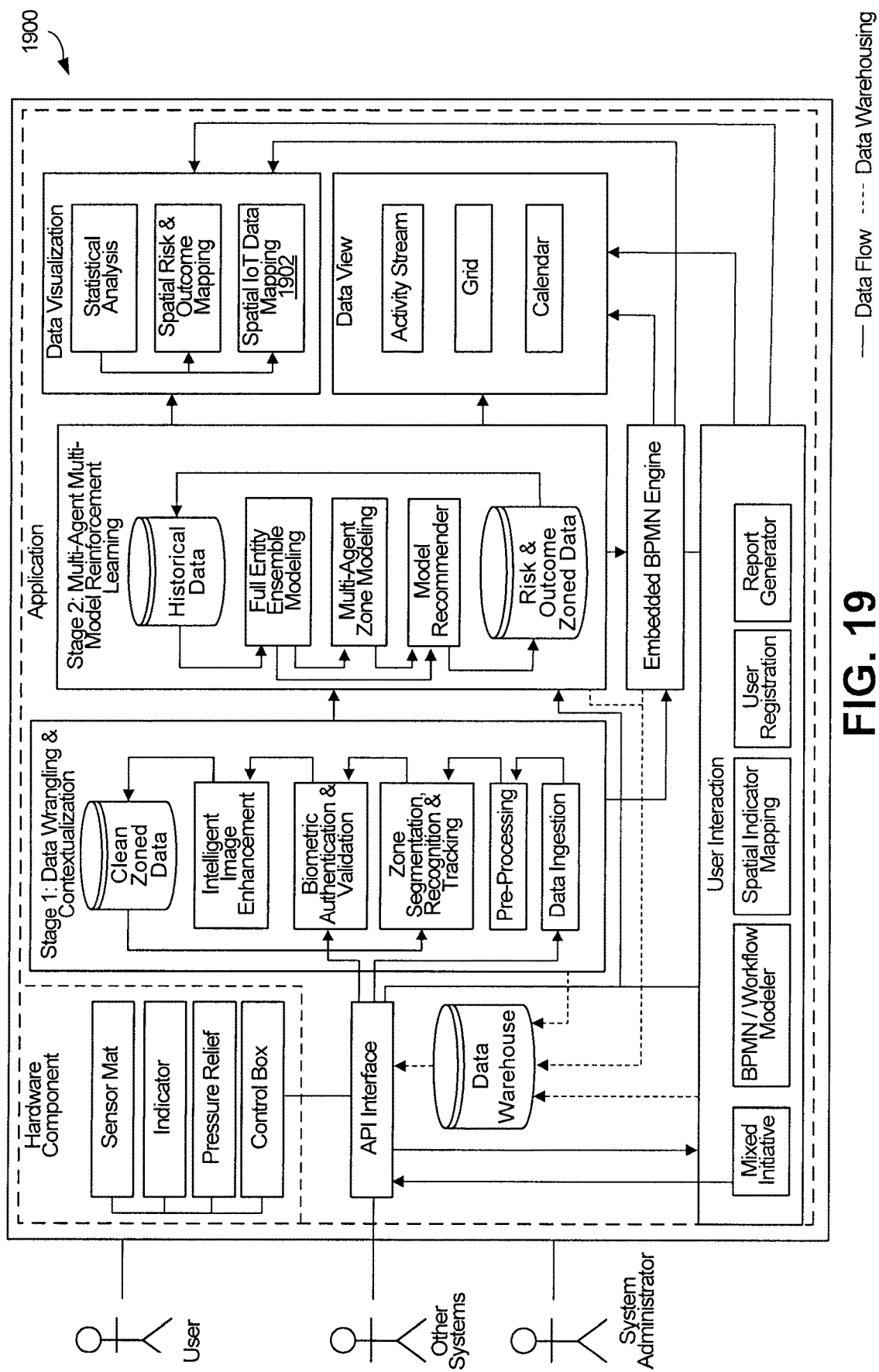
FIG. 19 is a flow-chart of another method of facilitating communication between hardware and software components of a pressure injury management system, according to some embodiments.
Figure 20:
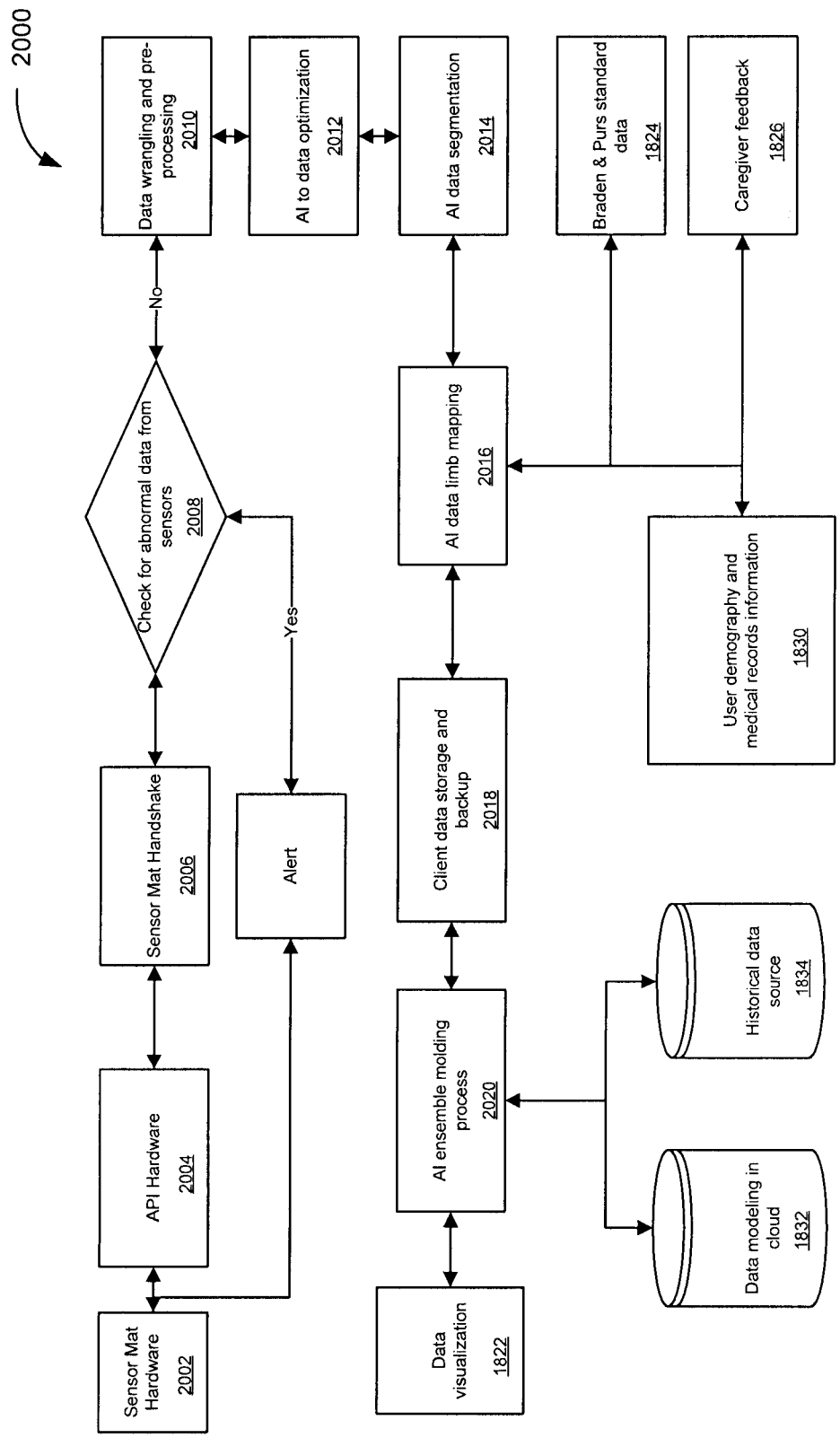
FIG. 20 is a flow-chart of an overview of an example software implementation, according to some embodiments
Figure 21A:
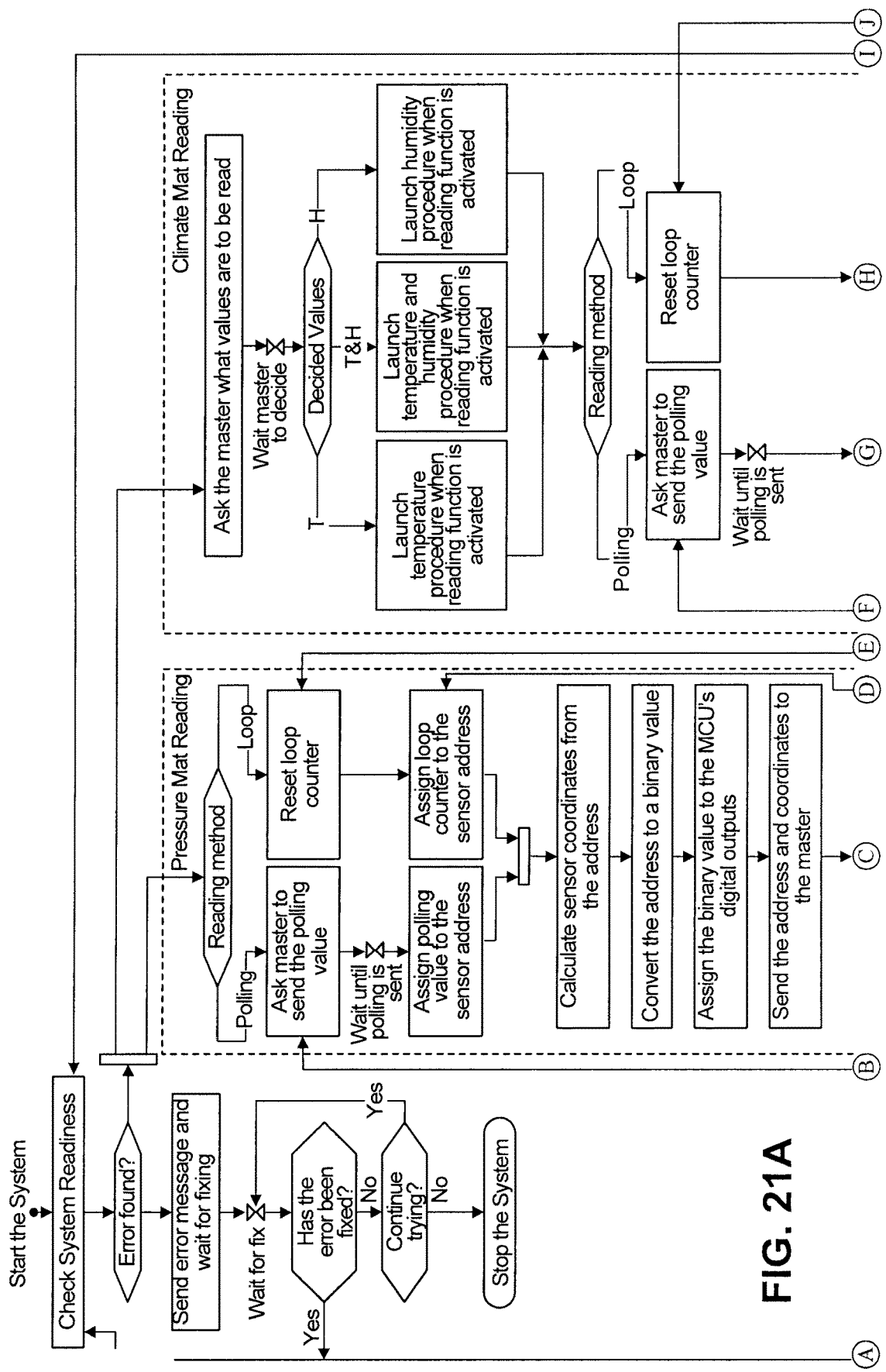
FIGS. 21A, 21B and 21C are a flow-chart of an example master controller software logic process, according to some embodiments.
Figure 21B:
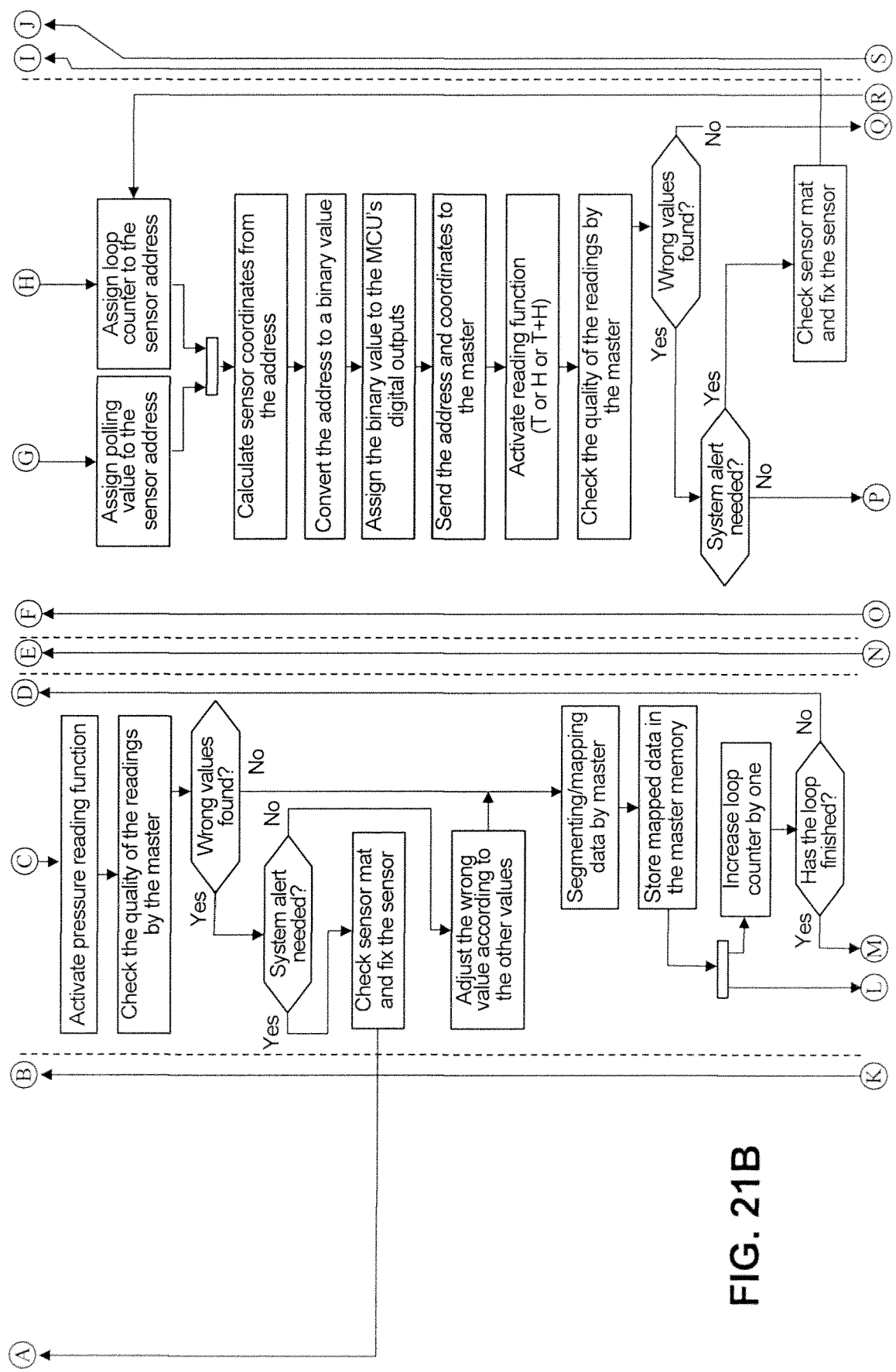
Figure 21C:
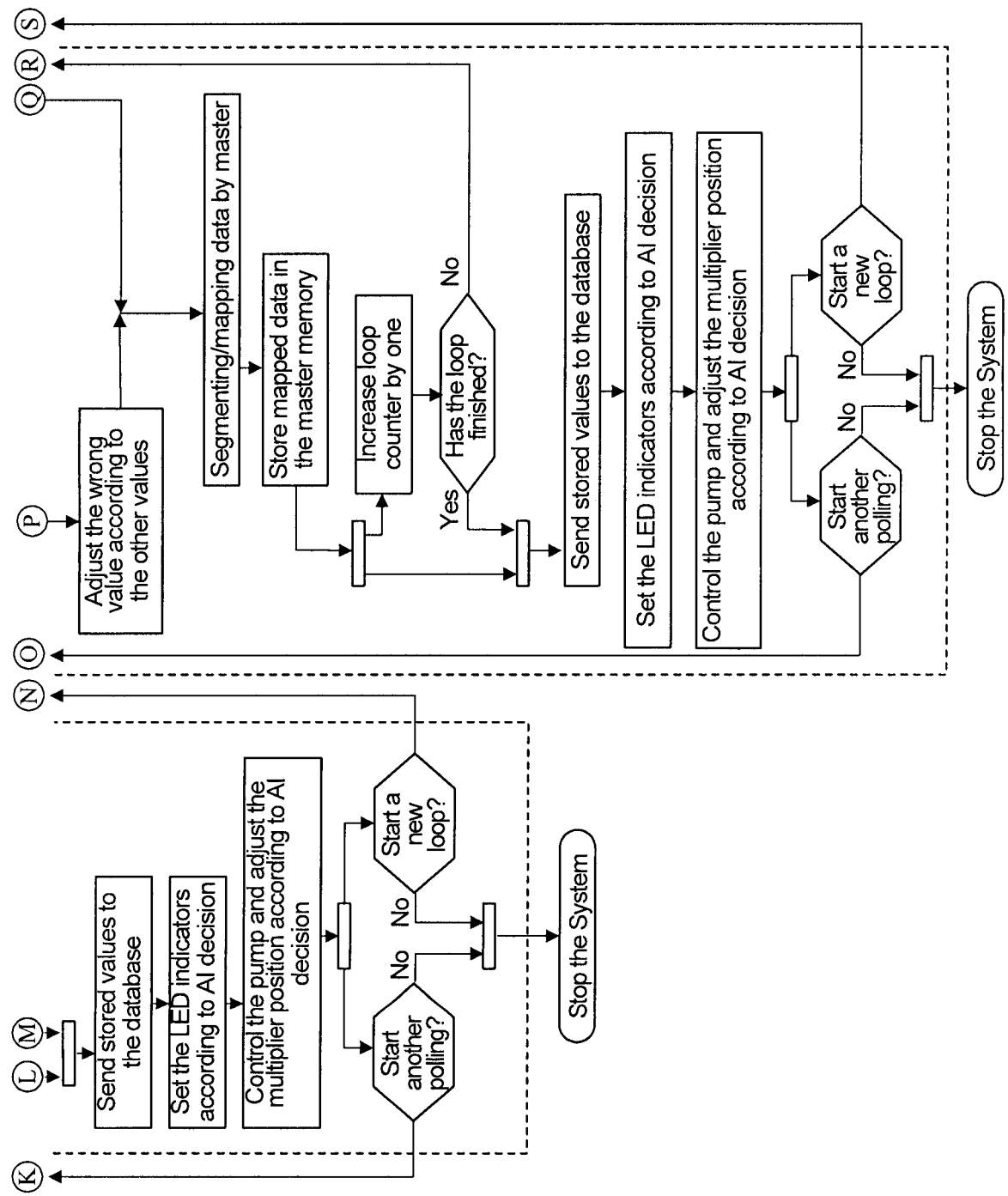

Referring to FIGS. 18 and 19, there are provided flowcharts of example methods of facilitating communication between hardware and software components of a pressure injury management system, according to some embodiments.

According to some embodiments, hardware component (1808-1814) may refer to physical IoT enabled components of the system. These hardware components 1808-1814 may be able to collect sensory data from various sensors included therein and may be able to react to commands provided by a computing device.

According to some embodiments, sensory mat 1808 may be an arrangement a plurality of sensors distributed in a defined pattern or known route allowing for sensory mapping.

According to some embodiments, indicator may allow for interfacing of system 1800 and user 1802 in a physical way (e.g., a user interface device). Indicators may be activated when the system 100 requires a user 1802 to take an action. As a non-limiting example, this may be accomplished by indicators that include LED lights, haptic feedback or audible alerts.

According to some embodiments, control box 1814 may be an IoT enabled control unit allowing the interfacing of the hardware components 1808-1814 and software components the system 100. Control box 1814 may contain one or more computing devices capable of localized processing. This may allow for system 100 to work independently and collaboratively with external hardware and applications. This may allow for leveraging of fog computing methods (also known as fog networking or fogging) to control and limit the flow of data among data sources. System 100 may localize data based on privacy concerns (e.g., store in data stores specifically located in order to comply with laws and regulations relating to health data) while leveraging external servers for processing power.

According to some embodiments, a block chain application level may be included to allow for a secure decentralized ledger in order to safeguard privacy and security of the system. Inclusion of a block chain ledger may also allow for control and accountability through a decentralized ledger reducing data embellishment.

According to some embodiments, API interface 1816 may comprise firmware or software that may allow for interfacing (handshaking) between system 100 and other systems, including databases, applications and hardware.

According to some embodiments, data warehouse 1818 may refer to one or more databases wherein all collected and processed data is standardized and stored (this can be local and/or off-site). Private user data including personally identifiable information (PII) may be masked in order to obfuscate identities and may be excluded during external, off-site, backups.

According to some embodiments, data wrangling and contextualization 1820 may be a process by which collected raw data (e.g., from hardware components such as sensors in sensor mat 1808) is run through a set of optimized agents and processes to be cleaned and prepared for various uses such as analysis, modeling, and visualization. Various steps may be involved in the wrangling and contextualization process (e.g., see FIG. 16 and FIG. 17).

In some embodiments, data wrangling & contextualization 1820 may have full tolerance in cases of malfunction of hardware; AI systems may subsidize data imputation (e.g., if missing some data, KNN may be applied to enhance resolution and measure average and neighborhood values. K=number of neighbours.).

According to some embodiments, data ingestion may include capturing data from various APIs. The system 100 may import, transfer and/or load multiple data types for the pre-processing stage. Control of data entering into the processing stage may be a critical element of optimizing the system 100 for near real-time processing of outcomes. This may be accomplished through the identification of primary and dependent data types via an AI recommender agent in order to control the flow of data into the processing based on the type of data available to the system 100 to identify high quality datasets from entirety of data sources.

According to some embodiments, pre-processing may include making data suitable to meet quantitative and qualitative standards through volume, variety, and velocity for analysis, modeling and visualization. Various data may need to be augmented and aggregated, may need to have important features of said data identified (feature selection), data type may need identification, appropriate sizing may be required, and data cleaning such as imputation, normalization, balancing, unbiasing, indexing, and metadata assignment may be necessary.

According to some embodiments, Zone Segmentation, Recognition, & Tracking may be executed when data pre-processing is complete. Data may be augmented based on predefined zoning of sensor location in relation to the various previously identified entity/body zones (e.g., head, limbs, torso, appendages). As an example, the center of a mattress may be associated with a body zone/body segment containing the user's hip. It will be understood that users includes entities, which can be a human, organism, object, or environment that can be spatially monitored for modeling through the present disclosure.

According to some embodiments, clustering algorithms such as K-mean may then be applied to the primary entity tracking variable to segment for high incidence zones in relation to each other. For example, for body tracking pressure may be used as k-mean centroid for each pre-defined zone. This may be done through clustering of centroids. If all centroids are clustering correctly relative to the pre-defined zone the zone recognition process may be initiated. If pre-defined zone centroid is missing, association rules can be applied to predict location and characteristics of missing zone centroid.

According to some embodiments, tracking variable may refer to the variable used primarily to spatially map the desired entity. For example, for bodies it can be pressure whereas for a heat source it can be temperature.

According to some embodiments, zone recognition may be carried out through modeling of k-mean and pre-defined zoning to predict zone locations and associations (relations between zones or dependent zones). Validation of zone recognition (in addition to association rules) may be done through comparison to historical data zoning data in order to identify the presence of missing zones, data anomalies or foreign objects not related to the targeted entity for filtering and augmentation. For example, if an anomaly is detected on/at a zone, the data may be re-processed without anomaly data and zone segmentation process may be carried out again. Tracking of unknown zones may be predicated on the combination of association rules and historical data. Once zone recognition has been validated. The k-mean tracking variable may be associated to its appropriate zone location in the appropriate zone data table. For example, for body tracking, pressure can be the tracking variable, pressure readings can be mapped to the zone their sensor is associated with. This may allow for a timeline view of all data that interfaced with the tracked zone over a span of time.

Variables spatially associated with the tracking variable are then mapped to the zone in relation to its location to the tracking variable in order to give relative spatial mapping of the tracking and associated variables to the zone.

According to some embodiments, data visualization 1826 may include mapping of an entity interacting with system 100. For example, as a first step, using cluster (K mean) the sensor mat 1808 may be divided into sensor clusters known to be likely to correspond to various parts of the user 1802 interacting with the system 100. Next, they system 100 may capture sensor data to relevant segment sensors and apply AI models (ex. KNN) to map. KNN may be used to confirm that read is at the location, According to some embodiments, confirmation of limb/entity part location may include use of two baseline values: cluster of body location; and pressure values of the sensor on the mattress. This may allow for two independent confirmations of zone segments. For precise mapping, AI (e.g., KNN) may be applied to map every sensor without overlapping or interfering with other clusters. This may increase resolution.

Some embodiments may use pressure as an indicator to accurately map body to sensors by associating relationships between pressure and other sensors (ex. Temperature and humidity).

According to some embodiments, data wrangling and contextualization 1820 may include biometric authentication and validation. Each entity and system may have its own unique ID associated to its data within a database in order to validate the correct association of the recorded data and unique entity the system will validate. A similarity function and fuzzy logic may be used to compare the recorded data with the desired entities historical data in order to validate the similarity. For example, using a combination of pressure profiles, sleep patterns, and physical characteristics in addition to normal authentication protocols a recorded set of data on a system can be validated to a targeted user for similarities. Results can be processed to confirm similarity of data in order to continue associated data recording for the entity or halt data recording when similarity score falls below a set threshold.

According to some embodiments, data wrangling and contextualization 1820 may include authentication & validation which may be carried out whenever an entity enters the system 100. Validation may also be carried out regularly during operation to confirm the presence of the appropriate entity.

According to some embodiments, multi-agent multi-model reinforcement learning methods 1822 may be applied once data wrangling and contextualization 1820 is complete. The data may then be utilized to apply two types of modeling, full-entity ensemble modeling and zone-based modeling.

According to some embodiments, reinforcement learning may be utilized to optimize learned knowledge from previous system experiences to build a knowledge base. The system may utilize previous learned models to initiate new personalized models for new entities through association (e.g., by similarity) of new entity with previous learned model entities. For example, a new patient with similar intrinsic and extrinsic factors to a previous patient could use the previous patient's learned model as the basis for the new patient's initial learned model allowing for leveraging of previous knowledge base. The new learned model can be personalized through a reinforcement learning approach core reward and punishment process.

According to some embodiments, as a prediction is evaluated by the RL model (through either system or user feedback) the predicted instance can be evaluated either positively or negatively (e.g., by a point-based ranking system). The evaluated instance can be added to the knowledge base. Similar instances to the evaluated instance can be ranked up or down. This can allow for personalization of models by ranking instances based on the feedback from the system; ranking down the importance of instances which may result in inaccurate recommendations and improving ranking of accurate recommendation instances for importance.

In some embodiments, ranking can be done relatively or absolutely for reinforcement learning based often based on the number of attributes. Reinforcement learning algorithms task may be to positively reinforce accurate prediction and negatively reinforce inaccurate prediction. Every recommendation may become another instance in a given dataset to build the knowledge base. The model can be periodically updated based on the rating of the system's performance by an operator (e.g. a nurse) or a system administrator 1806.

According to some embodiments, full-entity ensemble modeling 1822 may apply supervised machine learning pipeline processes to build models based on an ensemble modeling approach. Selected algorithms may be voted to select the most accurate algorithm for the desired outcome. Ensemble is a set of machine learning algorithms (random forest, SVM, deep learning, xg boost) which select the algorithm that yields highest accuracy through voting among them.

According to some embodiments, multi-agent zone modeling 1822 may, due to multiple entity zones, cause the system 100 to apply a multi-agent system approach to assign a learning agent to model the desired outcome. In a Multi-agent system, each agent may, for example, model one segment of the body. Each body data segment may have a unique agent to apply that data set to the ensemble.

According to some embodiments, model recommender may compare the multi-agent output to the full-entity ensemble model for validation and accuracy determination. Recommender may select either the multi-agent model or full-entity ensemble model for each zone in order to select the most accurate model for the desired outcome. Recommender model outputs may be saved to their associated zone table in a database for the use in analysis and spatial visualization.

According to some embodiments, historical data 1822 may consist of attributed user data and outcomes; the system 100 may collect behaviour of each user in respect to model outputs. The modeling data may be augmented by user 1802 or system feedback. Each recommendation may be input as a new instance into the historical data set 1822.

According to some embodiments, embedded BPMN engine 1824 may integrate a business process modeling notation engine to augment the workflow for process optimization. This may allow for seamless integration of system 100 into workflow of an operator and may reduce the need for change from operators to adapt to functionality of the system 100. In some embodiments, the engine consumes workflows, rules and parameters provided to allow for modeling of both automated and human steps involved in the execution of a workflow.

According to some embodiments, user interaction 1830 may refer to a front-end of the application through which users input data back into the system 100 for processing (e.g., a user interface device). The data may be used by the system 100 to calibrate, learn and transform the data into a format desirable for consumption.

For example, in a mixed initiative system an automated agent may provide a user/operator with a recommendation, but the final decision may be made by a human. Essential actions can be carried out by a human while nonessential actions can be carried out by the system 100. The system's 100 level of control can be adjusted based on performance of models, risk, and action delegation by the user.

According to some embodiments, spatial indicator mapping 1830 may allow a user to spatially map the location of indicators or feedback regarding the modeled entity. By utilizing spatial indicator mapping the model can be better trained to predict outcomes across the entity and its zones. In some embodiments, this may be critical for constructing localized models across an entity.

According to some embodiments, through user registration 1830 a user can be registered into the system and provide key attributes required for accurate modeling and effective workflow modeling. This may include an operator completing one or more risk assessment questionnaires (see FIG. 14) which may require the operator to input certain information into the system 100.

According to some embodiments, report generator 1830 may perform digitization of data entered by users 1802 through the system 100. This may allow for effective information sharing and processing of data through augmentation with IoT gathered data and transformation through modeling for the creation of new insights. Reports may be generated through the system 100 to report important relevant pieces of information.

According to some embodiments, data visualization 1826 may include providing visualizations of the layered outputs and inputs of the model oriented spatially and temporally (e.g., see FIG. 12). Visualizations can be displayed through a variety of interfaces including but not limited to mobile, web-based, wearables, device alerts, and augmented reality.

According to some embodiments, statistical analysis 1826 can include statistical significance analyses for variables associated with the modeled outcome. This may include averaging, summing, variance, filtering, and abstraction.

According to some embodiments, spatial risk & outcome mapping 1826 includes mapping of model outcomes to the physical structure of the modeled entity. This may be accomplished through association of the model outcome to the modeled data to determine spatial relation of outcome result and modeled entity.

According to some embodiments, spatial IoT data mapping (see FIG. 19, 1902) can include mapping of data gathered by system 100. Mapping of tracking variable or spatial defined sensors through visualization tools to spatially represent mapped entity. Variables without defined spatial references can be spatial associated to known spatial variables for mapping on entity.

According to some embodiments, data view 1828 can include representation of data outputted by the system 100 for consumption by the user 1802.

According to some embodiments, through activity stream 1828 notifications may be generated by the systems 100 and transmitted to users 1802 associated with the modeled entity via a user interface. Notifications may populate the activity stream in order to centralize all notifications in a way that is easy to consume (e.g., see FIGS. 11-13, 15).

According to some embodiments, calendar 1828 may enable viewing of notifications and actions predicated by the system 100 that require user execution at specific times. This may allow for temporal association of actions and feedback of availability to respond to the system 100 to escalate information to appropriate user 1802.

According to some embodiments, risk grid 1828 may provide views of modeled entities on a "grid". The risk grid view may contain key attributes used for monitoring. Conditional formatting of grid can be deployed to associate certain user interface elements (e.g., change in color, blinking, etc.) with outputs from the system 100.

Figure 23A:
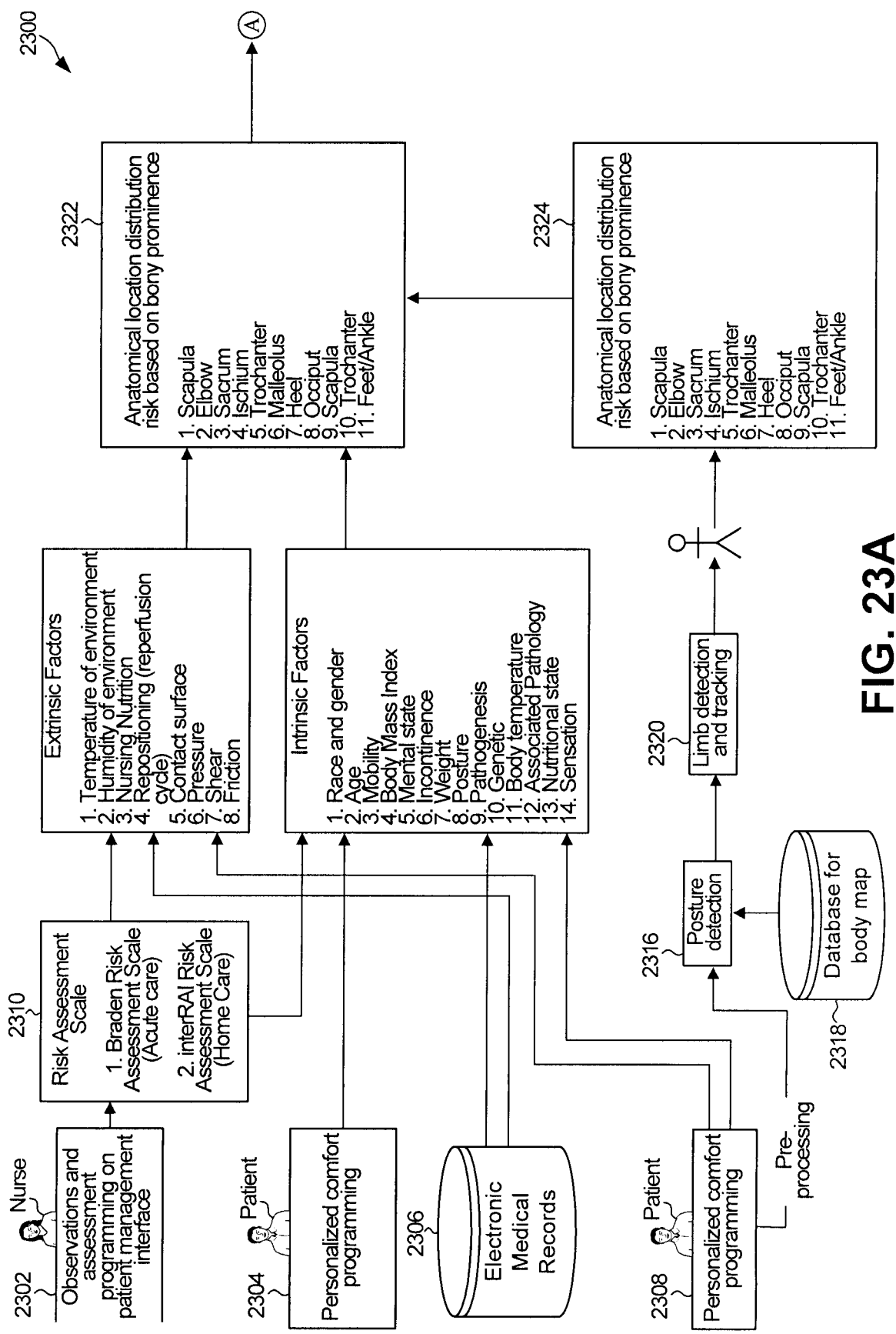
FIGS. 23A and 23B illustrate a flow-chart of a risk assessment process, according to some embodiments.
Figure 23B:
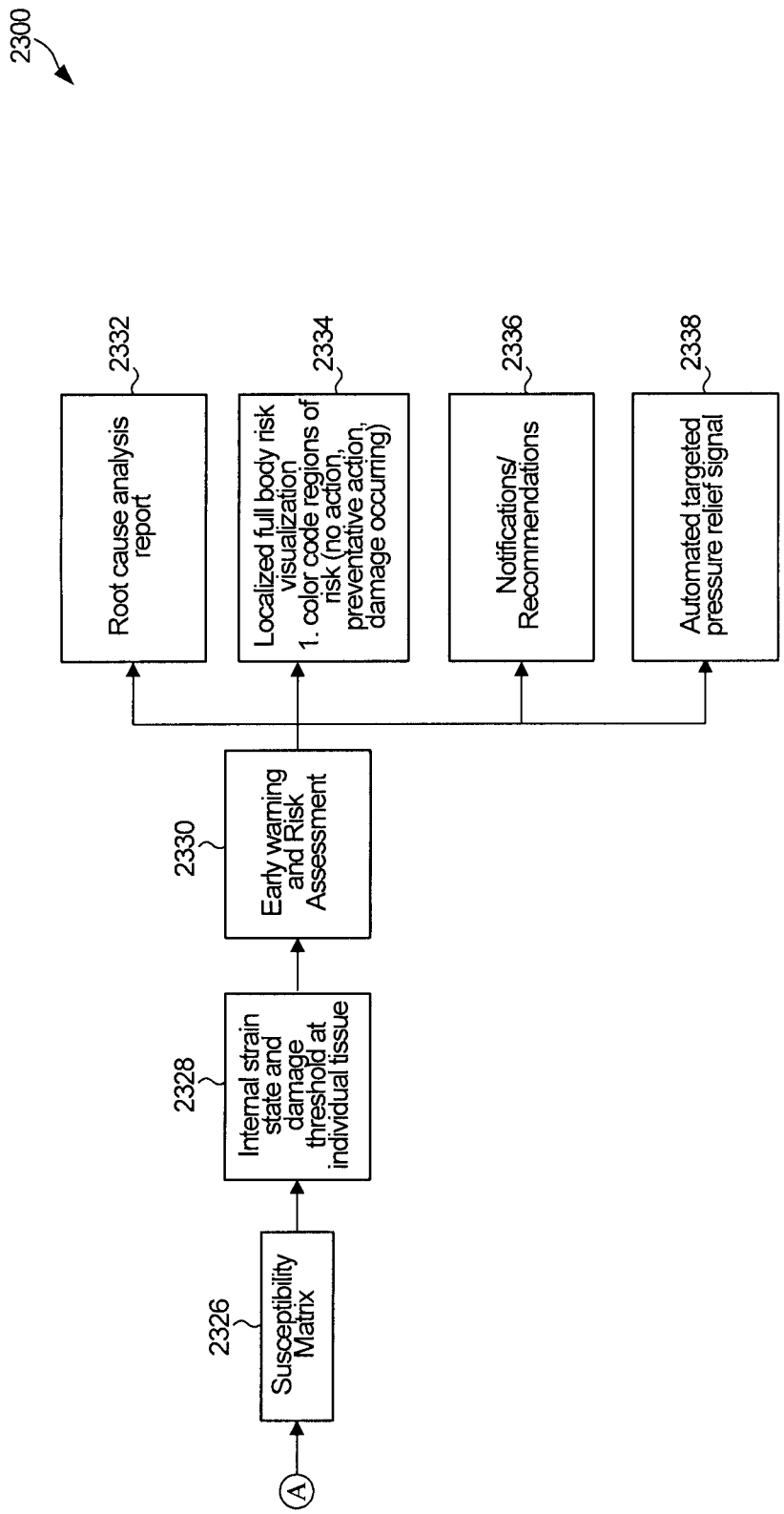

Referring to FIGS. 23A and 23B, there is provided a flow-chart of a risk assessment process, according to some embodiments. Pressure injury risk assessment scales have a problem of over prediction. This represents a major problem for the healthcare system, from a financial standpoint. Furthermore, these scales are not as comprehensive as they need to be. This is indicated by poor psychometric performance in healthcare wards in which a high percentage of patients carry additional morbidities. Pressure injury risk assessment scales are inherently a qualitative process, which is their downfall. We acknowledge 'state of the art' pressure injury risk assessment scales are intended to capture, empirically, the essential aspects of the same underlying constructs (the domain of mobility/activity, skin/pressure status, etc.). We also acknowledge, that each single question on the pressure injury risk assessment scale is unlikely to represent the broad scope of the complex interplay of factors involved in pressure injury formation. Further, they are indeed imprecise because they cannot discriminate to a fine degree, between the different levels of an attribute (prone to random error). The more predictive scales use multiple items to overcome limitations of single items, to enable better precision (such as InterRai over Braden).

A number of studies that validate based on reliability and validity (in terms of Streiner and Norman to provide standardization), provide results that can be used (the multiple questions from multiple pressure injury risk assessment scales) to develop a more reliable overall assessment of factors which are important in patient susceptibility. In other words, there is a need to address all the underlying constructs involved in the 'state of the art' assessment scales—validation of the core set of risk factors involved in pressure injury risk formation. If these once unobservable (latent) variables can be addressed and made quantifiable using a quantitative measuring tool, such as a biosensor, the underlying constructs can be addressed (main domains involved in pressure injury formation), but with precision and reliability.

Further, visual appraisal is not a sufficient means of assessment for pressure injury risk assessment domains. This is due to the nature of domains such as "moisture", and "mobility", which by definition require a more accurate method for true measurement. Recent biosensor and machine learning advances have shown promise in the field of pressure injury prevention. There is a need for a comprehensive automated pressure injury risk assessment system which replaces visual appraisal and pressure injury risk assessment questionnaires through the use of biosensors and uses machine learning algorithms.

The overall goal of this risk model may be to develop a modeling system that utilizes both historical data of the patient and real-time environmental data via a biosensor system on the basis of environmental parameters, to predict deep tissue injury at an early stage and send a subsequent signal to initiate an action (recommendation or target pressure redistribution). With this data to act on, monitoring systems can become integrated into the hospital bed to provide automatic redistribution of the patient according to the generated redistribution plan, based on real time biological data of the patient, for key parameters involved in pressure injury formation. Since interaction with the hospital bed and patient, due to interface pressure (bedding), is a key cause of pressure injuries, a smart bed that does risk modeling real-time can may provide a first line of defense in preventing them.

There are two primary components that contribute to risk of development of pressure injuries. These are, internal risk factors and external risk factors:

Internal Risk Factors:
Race and Gender
Age
Mobility
Body Mass Index
Mental State
Incontinence
Weight
Posture
Pathogenesis
Genetic Factors
Body Temperature
Associated Pathology
Nutritional State
Sensation
External Risk Factors
Temperature of Environment
Humidity of Environment
Nursing Nutrition
Repositioning
Contact surface
Pressure
Shear
Friction Currently, the documentation of both external and internal risk factors is done manually by healthcare professionals. Aspects of the present disclosure may be able to extract patient data pertaining to these risk factors through digitization of risk assessment scale paperwork, as well as from EMRs (electronic medical records) or EHRs (electronic health records). To supplement the extracted data, equipped biosensors may be able to recognize limbs of the patient, thus approximating the locations where pressure injuries are most likely to occur. These locations are known as the bony prominences of the body and include the scapula, elbow, sacrum, ischium, trochanter, malleolus, heel, occiput, and the feet/ankle.

Additionally, these biosensors provide real-time measurements of pressure, temperature, and humidity data, all three of which are included in the risk factors for pressure injuries. The analysis of this data may provide meaningful information with clinical implications, such as:

Magnitude of local mechanical load

Magnitude of skin temperature and local humidity

Time duration of mechanical load, temperature, and humidity

Type of loading (friction, shear, interface pressure)

Mechanical properties of the tissue

Geometry of the tissues and bones

A non-limiting example of how this risk model may be applied by the present disclosure is provided below and depicted in the flow diagram of FIGS. 23A and 23B. Temperature data is listed for some of the bony prominences of the body. Baseline data indicates that a temperature of 27.8° C. is present at the heel of a particular individual. As mentioned earlier, 0<V<Vmin represents a zone of low vulnerability. Therefore, up to a temperature of 28.3° C., the present disclosure may not recognize a threat to the heel tissue of this individual. However, from Vmin<V<Vmax, or 28.3° C.<V<30° C. the heel tissue is in a vulnerable state, which may prompt the release of an alert notification.

| Body Part | Baseline Temp(° C.) | D min | D max |
| --- | --- | --- | --- |
| 1. Heel/Feet | 27.8 | +0.5° C. | +2.2° C. |
| 2. Sacral region/trunk | 31.3 | +0.5° C. | +2.2° C. |
| 3. Head and neck | 32.9 | +0.5° C. | +2.2° C. |
| 4. Upper arm/back of shoulder | 24.6 | +0.5° C. | +2.2° C. |
| 5. Lower arm/elbow | 27.7 | +0.5° C. | +2.2° C. |
| 6. Lower legs/between knees | 25.8 | +0.5° C. | +2.2° C. |
| 7. Between ankles | 27.8 | +0.5° C. | +2.2° C. |

This same principle may be applied by the present disclosure for both pressure and humidity. This information along with the extracted patient data, may provide a "susceptibility matrix", through which damage may be assessed at the individual tissue level.

According to some embodiments, the present disclosure may use full body color coded risk visualization to provide enhanced risk assessment methods. Based on the real-time biosensor data and this full body visualization, a root cause analysis report may be generated providing information to caretakers as to the contributing factor behind the risk of pressure injury at each location of the body. If urgent action is required to prevent the development of a pressure injury, notifications may be provided to operators (e.g., nurses, caretakers, doctors, etc.) by the present disclosure, and targeted automated readjustment of pressure may be performed (e.g., by a pressure relief—see 2702 in FIGS. 27A, 27B and 27C).

1.3 Vulnerability Model

Research shows that some individuals are more susceptible to pressure injuries than others due to certain mechanical loadings not yielding the same amount of damage, internally, in each individual. This can be further broken down two principles:

The internal mechanical state of tissues depends on two things, the variations in mechanical and/or geometrical properties of tissues among patients Other factors play a role in this process, e.g. lack of tissue repair, bad tissue perfusion, and altered metabolism.

Figure 29:
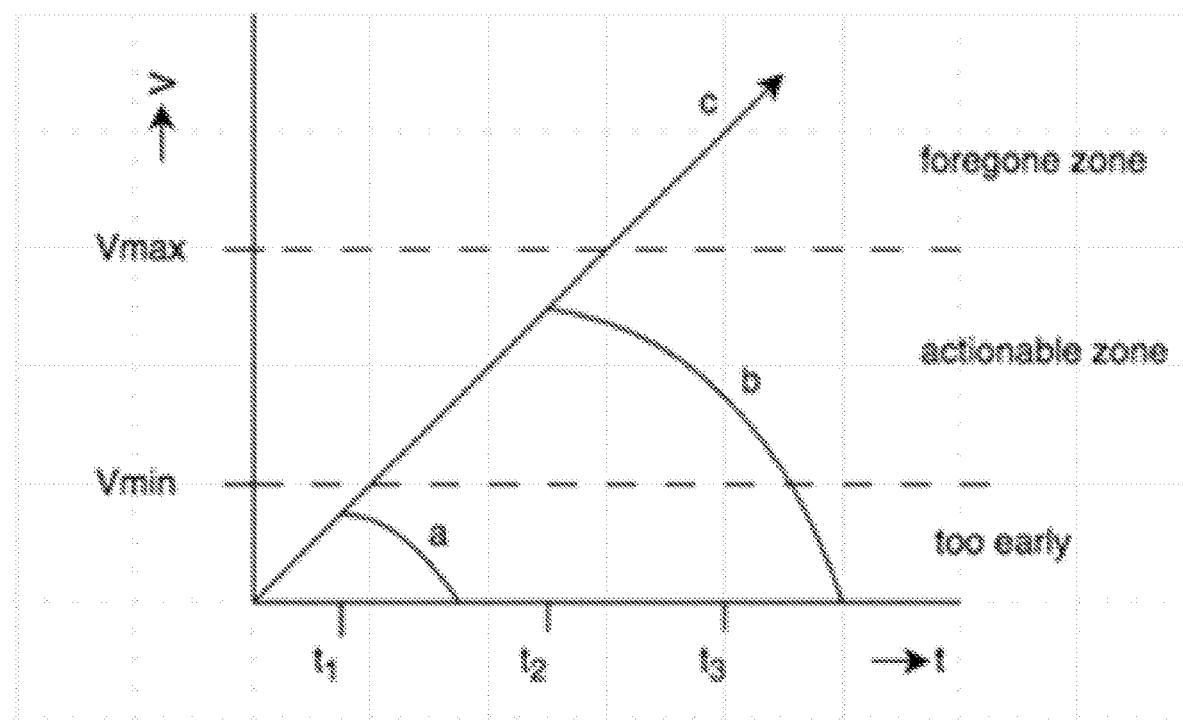
FIG. 29 is a graph depicting a relation between time and vulnerability.

FIG. 29 is a graph depicting a reation between time and vulnerability. In FIG. 29, 'V' measure the vulnerability of developing a pressure injury based off of data and information provided from the model. Let 't' represent the time in regards to the activation of the system. IN FIG. 29, 0<V<Vmin represents the zone where the system does not recognize an immediate threat towards formation of pressure injury, and indicates low vulnerability. The zone Vmin<V<Vmax, is representative of an actionable zone where the integrity of the integument is in a vulnerable state. Alert notification regarding the vulnerability will be generated. Beyond Vmax, the present data realizes a foregone zone, most likely to present the development of a pressure injury. Alert notifications will still be generated. Curves a and b represent the time of the system to record lower states of vulnerability, indicating preventative measures have resulted.

This enables the system to assess the potential risk of pressure injury formation on each limb, as different postures expose limbs to differing amounts of pressure load, which alter when a patient moves. What this allows for is targeted and insight-based pressure redistribution, when automatically repositioning patients within set time intervals and visually representing risk in the form of color-coded regions/sending a series of requests to other systems.

Figure 24:
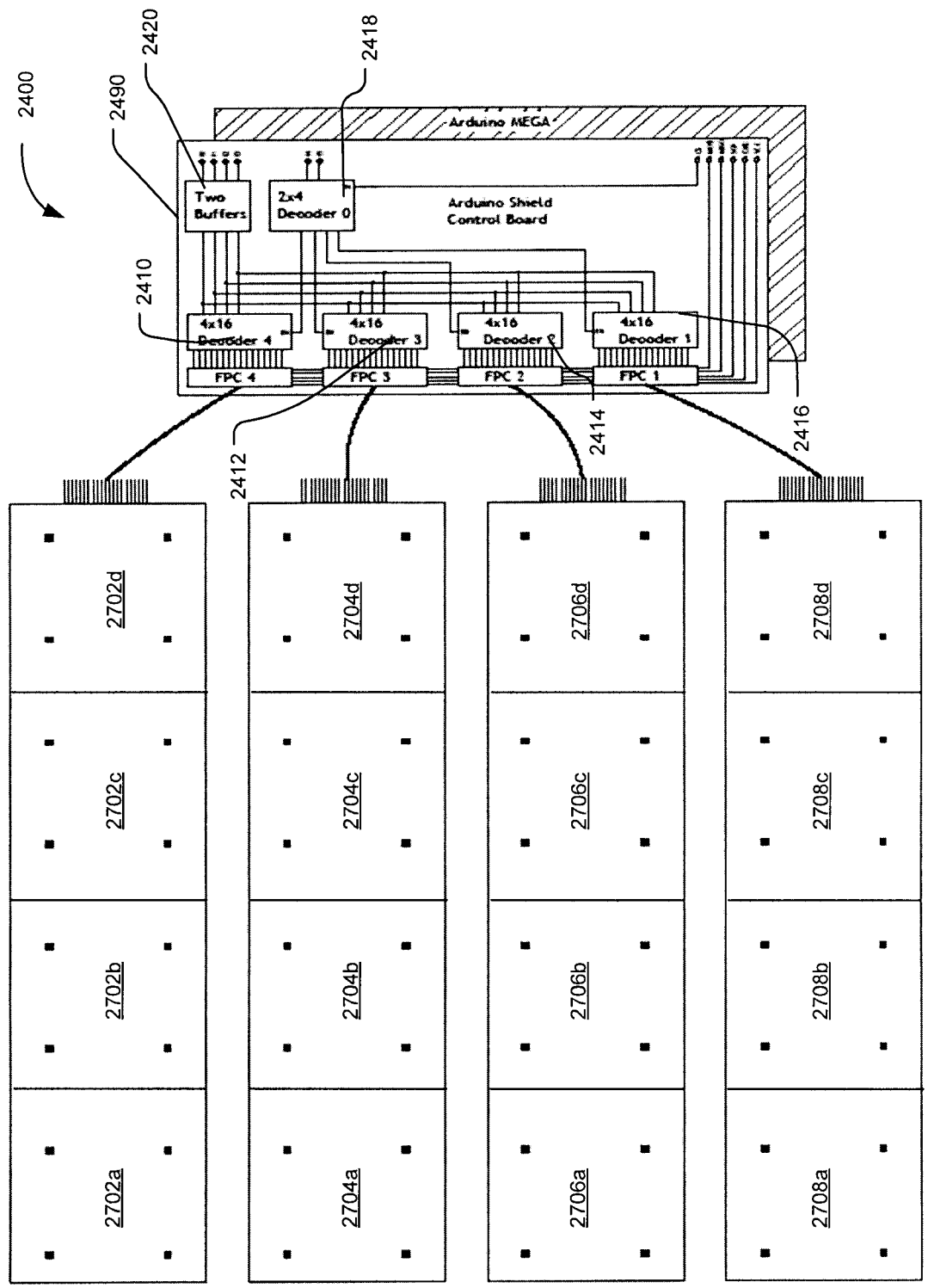
FIG. 24 is a plan view of an example sensor and pressure microcontroller layout, according to some embodiments.
Figure 25:
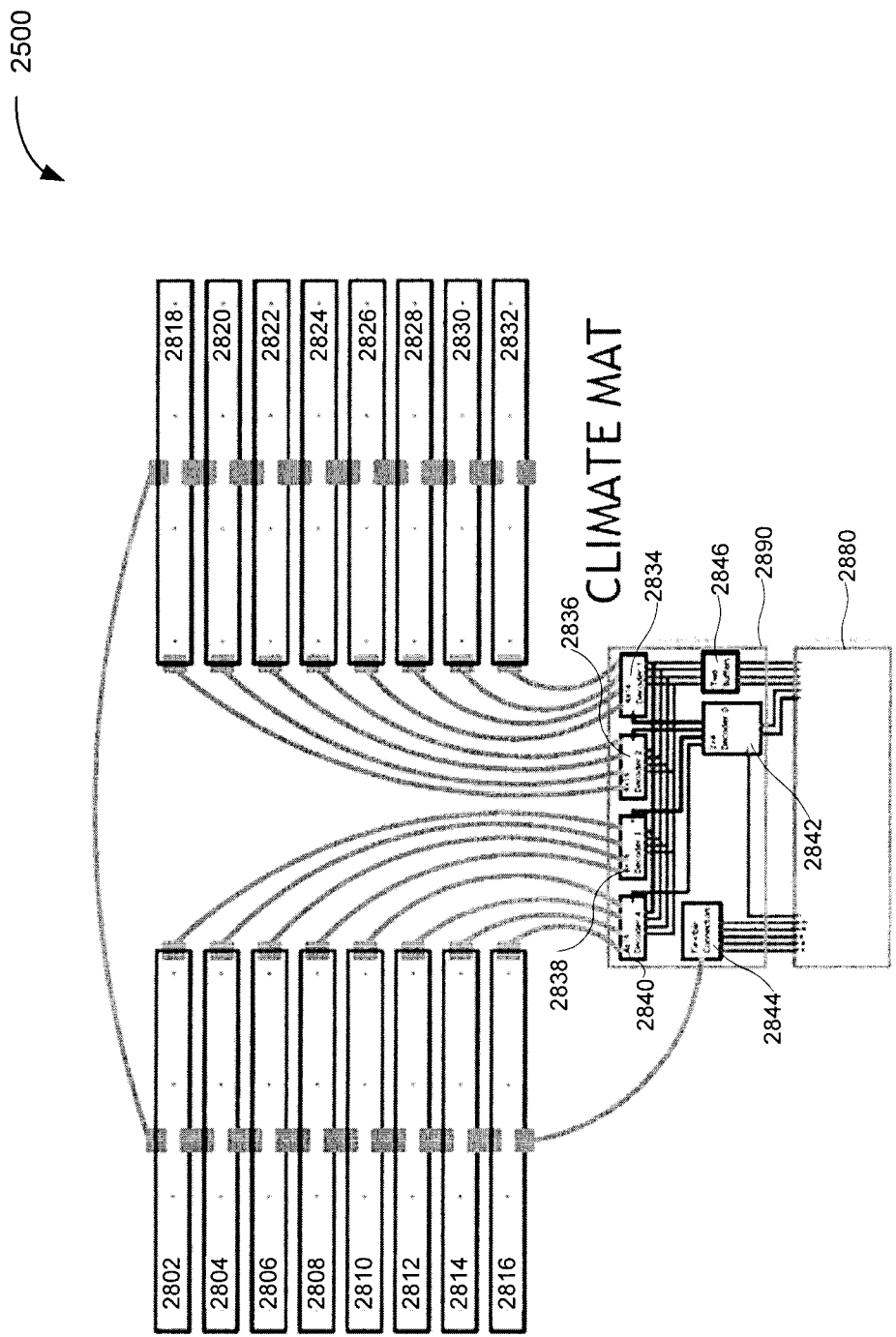
FIG. 25 is a plan view of an example bus arrangement for climate sensor FPCBs in a climate sensor layer, according to some embodiments.

Referring now to FIGS. 24 and 25, these figures may, respectively, provide plan views of example bus arrangements for pressure sensor FPCBs and climate mat FPCBs (e.g., pressure mat 2748 and climate FPCB 2742 in pressure sensor layer 2726 and climate sensing layer 2724), according to some embodiments.

Figure 22:
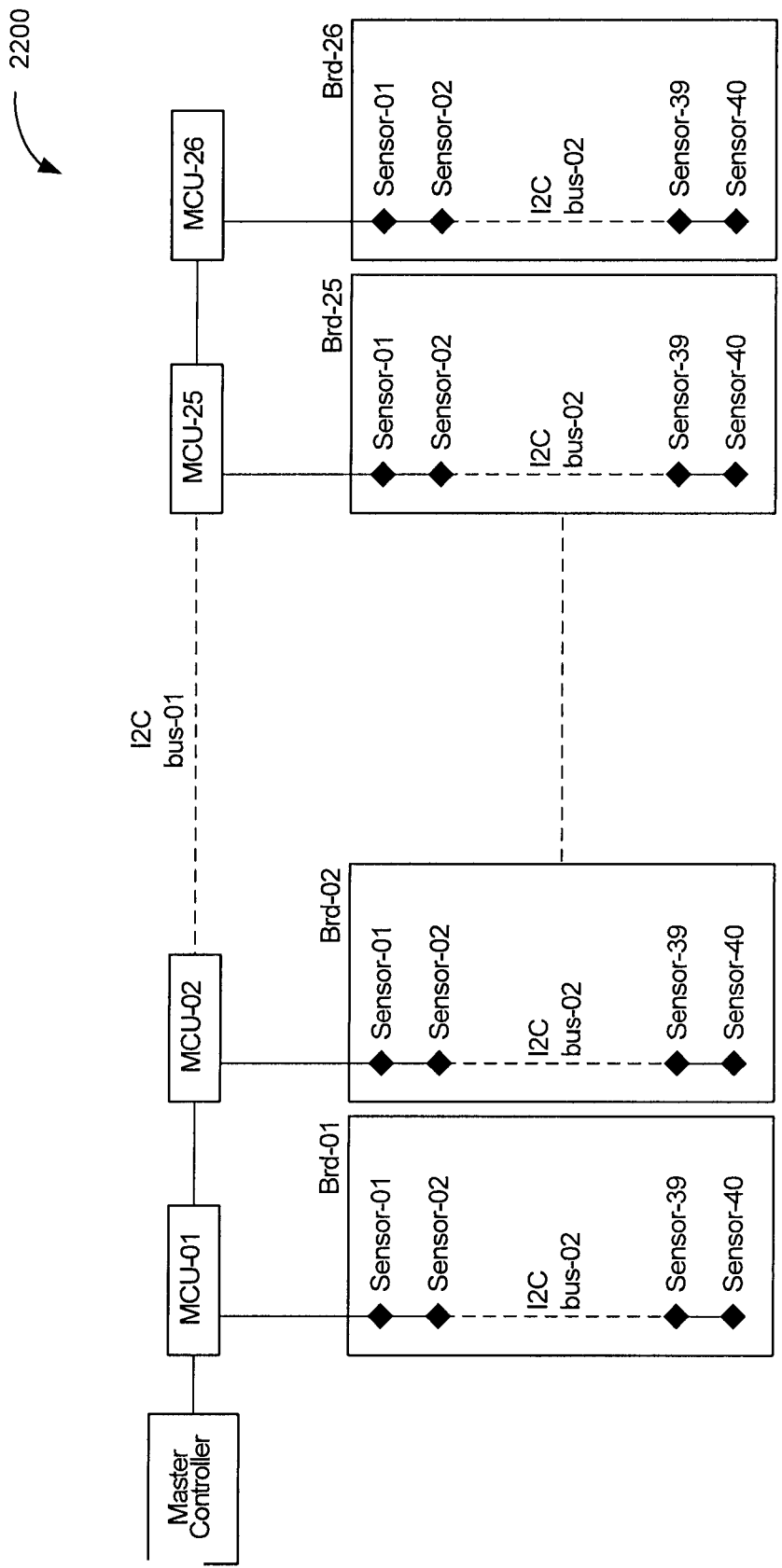
FIG. 22 is a block diagram showing an example method for providing a sensor network, according to some embodiments.

Making specific reference now to FIG. 25, in some embodiments the climate sensors (e.g., 2502-2532) may be connectable via two digital protocols: SPI and I2C. I2C protocol, an example of which is depicted in FIG. 22, is very common and may requires only 2 wires to achieve connection (clock line (SCL) and data line (SDA)), but may be too slow for effective incorporation into system 100 (i.e., 400 KHz). I2C may have further limitations in that it may support a maximum of 127 sensors. Moreover, the noise immunity threshold of I2C may be undesirably low because the bus may carry all addresses and data for all sensors.

In contrast, the Serial Peripheral Interface (SPI) protocol, on the other hand, may be faster than I2C (i.e., 10 MHz), may support an unlimited number of sensors because there is no addressing, and may be immune to noise because it has a special line for sent data, a special line for received data, and a special line for the selected device. However, SPI may require 4 wires (serial clock (SCK), Master Output Slave Input (MOSI), Master Input Slave Output (MISO), and chip select (CS)), so the hardware structure may be more complicated, especially since a unique CS signal is required for each sensor.

There may be two ways to generate a unique CS for each sensor (e.g., 2502-2532): a shift register; and a decoder/demultiplexer. Active-low decoders may be more suitable than shift registers because the logic is direct TTL without any need for clock synchronization, so the propagation delay may be less than 15 ns. Moreover, without decoders there may be a possibility of selecting two sensors simultaneously, which might be caused by simultaneous signals from two cascaded registers. While decoders may ensure only one active output for a given input and may ensure that all other outputs are inactive. A problem with using decoders may be that the number of inputs, which should be determinable according to the equation: $X=Log_2(Y)$; where X is the number of the inputs and Y is the number of the outputs. For example, with 512 sensors (outputs) a decoder with 9 inputs may be needed to decode to decode the sensors because $Log_2 (512)=9 \Leftrightarrow (2^9=512)$. This problem may be solved by using digital outputs of the microcontroller. Thus, after accounting for the number of sensors (e.g., 2502-2532) the microcontroller should have some free digital outputs; this may be one of the advantages of using Arduino® controllers.

Connecting to the Decoding Logic:

Addresses may be carried to the decoders (e.g., 2534-2542) by the digital outputs of microcontroller which will be shared with the decoders' (e.g., 2410-2418, 2534-2542) inputs. However, such a configuration may not be implementable by simple direct connections because due to a fan-out problem. The DC current per an I/O pin may be 40 mA and the DC current per a decoder (e.g., 2534-2542) input may be 20 mA. As a result, it may be the case that a single microcontroller pin may be connected to two corresponding decoders' (e.g., 2534-2542) inputs at a maximum. For example, if four are connected together, they will absorb 4×20 mA=80 mA, while the decoder (e.g., 2534-2542) can provide 40 mA only, this will cause malfunctioning.

In some embodiments, one or more line buffers 2546 may be used to solve this problem and may maintain the stability of addressing lines. Line buffers 2546 may perform the Boolean function Y=A in positive logic. The DC current for a buffer input may be only 1 mA, while the DC output of it is 40 mA. Therefore, 40 buffers line buffers 2546 could be connected to a single microcontroller pin and each of them could supply two decoder inputs. Some embodiments of the present disclosure implement two sets of 4 line buffers 2546, each of them may be connected to the microcontroller inputs and may feeding two decoders (e.g., 2534-2542). One or more pull-up resistors may be added to the line buffers' 2546 outputs since they are (Open Collector) OC outputs.

Reading Procedures:

In some embodiments, the microcontroller may check the readiness of the SPI bus and may return corresponding error messages in case of errors. If no errors occur, the reading loop may start with sensor No. 1 (e.g., 2502) and may end with the last sensor e.g., 2532) and may repeat the cycle again. The loop counter may be equivalent to the sensor number and may be converted to a binary number on the microcontroller outputs as an address.

In a non-limiting example embodiment, the address digits of each sensor may have the format of (xxxx,xxxx). The most significant bits (MSBs) may enable selecting one of the decoders (e.g., 2534-2542), and the least significant bits (LSBs) may enable selecting one of the sixteen sensors (e.g., 2502-2532) that are connected to a particular decoder. The selected sensor (e.g., 2502-2532) may be activated and, if so, will occupy the SPI bus shared by all sensors. During this occupation, the sensors (e.g., 2502-2532) may receive commands from the microcontroller via MOSI line and then may send the results to the microcontroller (e.g., 2756, 2580) via MISO line, this may be synchronized by SCK line. At this point, the microcontroller (e.g., 2756) may have completed the reading procedure and the loop counter may be incremented by 1 to select the next sensor (e.g., 2502-2532). The next sensor number may be translated to (xxxx,xxxx) format and may be sent again to the decoding logic (2766) that may de-activate the previous sensor (e.g., 2502-2532) and activate the next one. This may allow proper use of the SPI bus and reliable communication with the microcontroller (e.g., 2756, 2580).

In some embodiments, a polling/reading procedure may be implemented in addition to the loop procedure. According to an example embodiment of the polling reading procedure, when the master controller 2762 indicates that values from a certain sensor should be read without waiting for the entire whole loop to complete, master controller 2762 may send the number associated with the particular desired sensor to one or more microcontrollers. In response, microcontroller may convert the number associated with the sensor to binary and may, subsequently, execute the process for retrieving values from the sensor. The advantage of this procedure may be that may provide the system 100 with more flexibility and may further reduce time and power consumption in special cases where data from one or more particular sensors is required immediately or more frequently than the loop allows (e.g., where an operator indicates that a patient has a particular body area that is at high risk for complications if pressure injuries arise therein).

In some embodiments, more than one type of PCB may be used to implement the design methodology outlined herein. In accordance with the above design methodology, two types of PCB may be utilized: the digital interface (e.g., 2754, 2490, 2590) that contains the decoders 2766 and buffers 2766 may be implemented using a rigid PCB, while flexible PCBs may be used to implement the various sensors and accompanying electronic components. Climate FPCBs (e.g., 2742) may be constructed using Flexible PCBs as they may be designed to be mounted as part of the climate sensing layer 2724 which forms part of the sensor mat 2704 which, in turn, may be designed to form part of, or be coupled with, a mattress. The digital interface 2754 may be rigid and may be located in the same control box 2708 which contains the master controller 2762 and the microcontrollers. As a non-limiting example, this rigid board could be an Arduino® shield board. Such a construction may save space inside the control box as no wires may be required with the Arduino® shield board.

Figure 26:
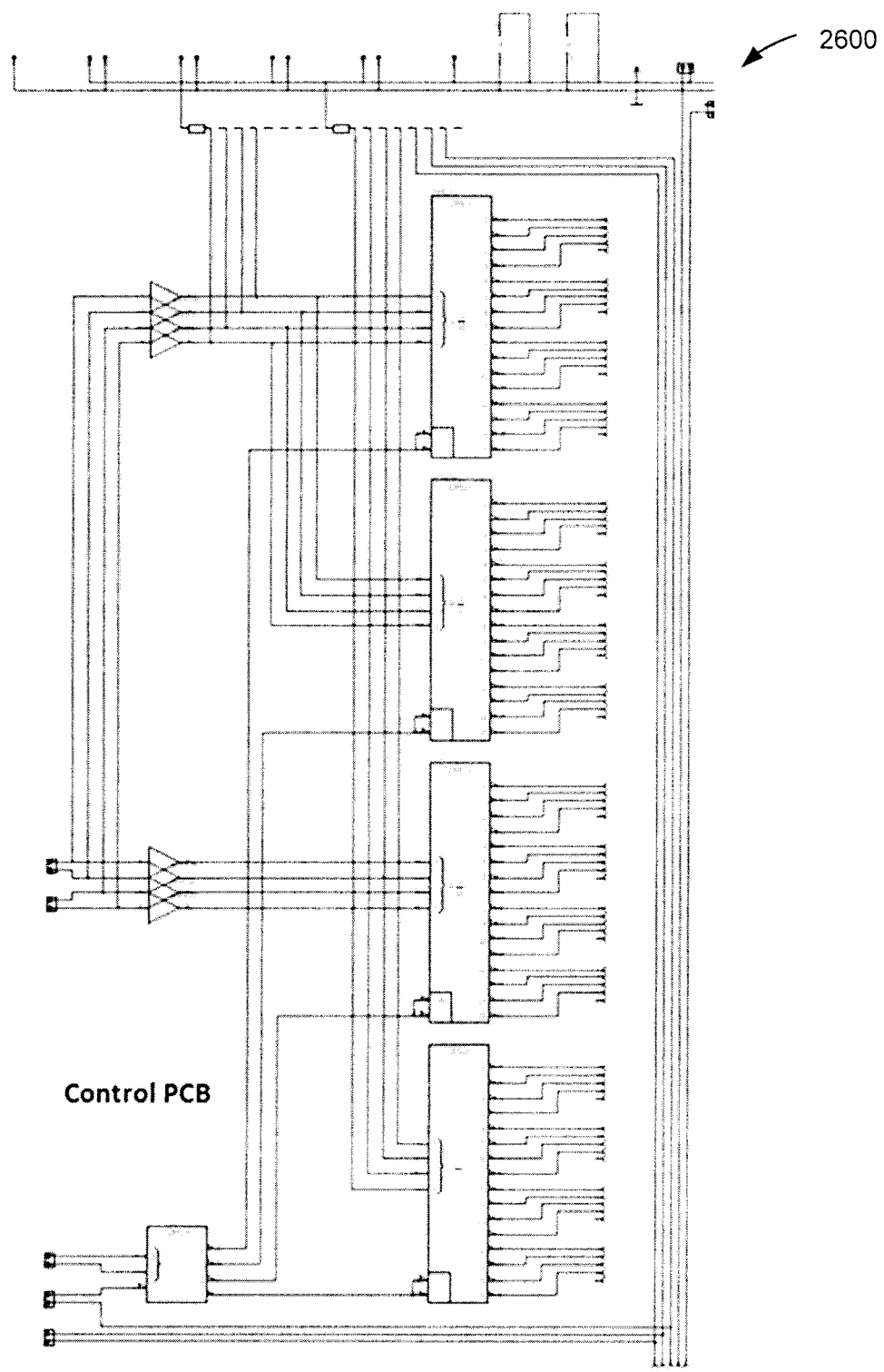
FIG. 26 is a schematic diagram of a control printed circuit board (PCB) for a climate sensing layer, according to some embodiments.

Referring now to FIG. 26, a non-limiting schematic diagram of a control printed circuit board (control PCB 2600) for a climate sensing layer may be provided, according to some embodiments. The example schematic diagram of control PCB 2600 may demonstrate tracing between multiple connectors through decoder and buffer stacking to connector to controller. Control PCB 2600 may comprise one or more layers rigid PCB that may contains required logic circuits (e.g., decoders, buffers pull up resistors, etc.), as well as terminals that may feed the control PCB 2600 with signals data signals and/or power (e.g., addressing lines, SPI lines, supply lines, etc.). Control PCB 2600 may also include Flat Flexible Cable (FFC) connectors that may carry transmitted CS signals to one or more included flexible PCBs, PCBs, and/or SPI+supply lines to flexible PCBs.

In some embodiments, control PCB 2600 may connect to one or more pressure PCBs, which may provide connection between one or more DIP connectors from one or more pressure sensors coupled to one or more air cells (e.g., air cell 2710). Pressure PCBs may further comprise connections to one or more pressure sensors (e.g., via FFCs).

Climate PCB: Demonstrates Tracing between Surface Mounted MEM sensors and connectors to Flat Flexible Cables.

Figure 27A:
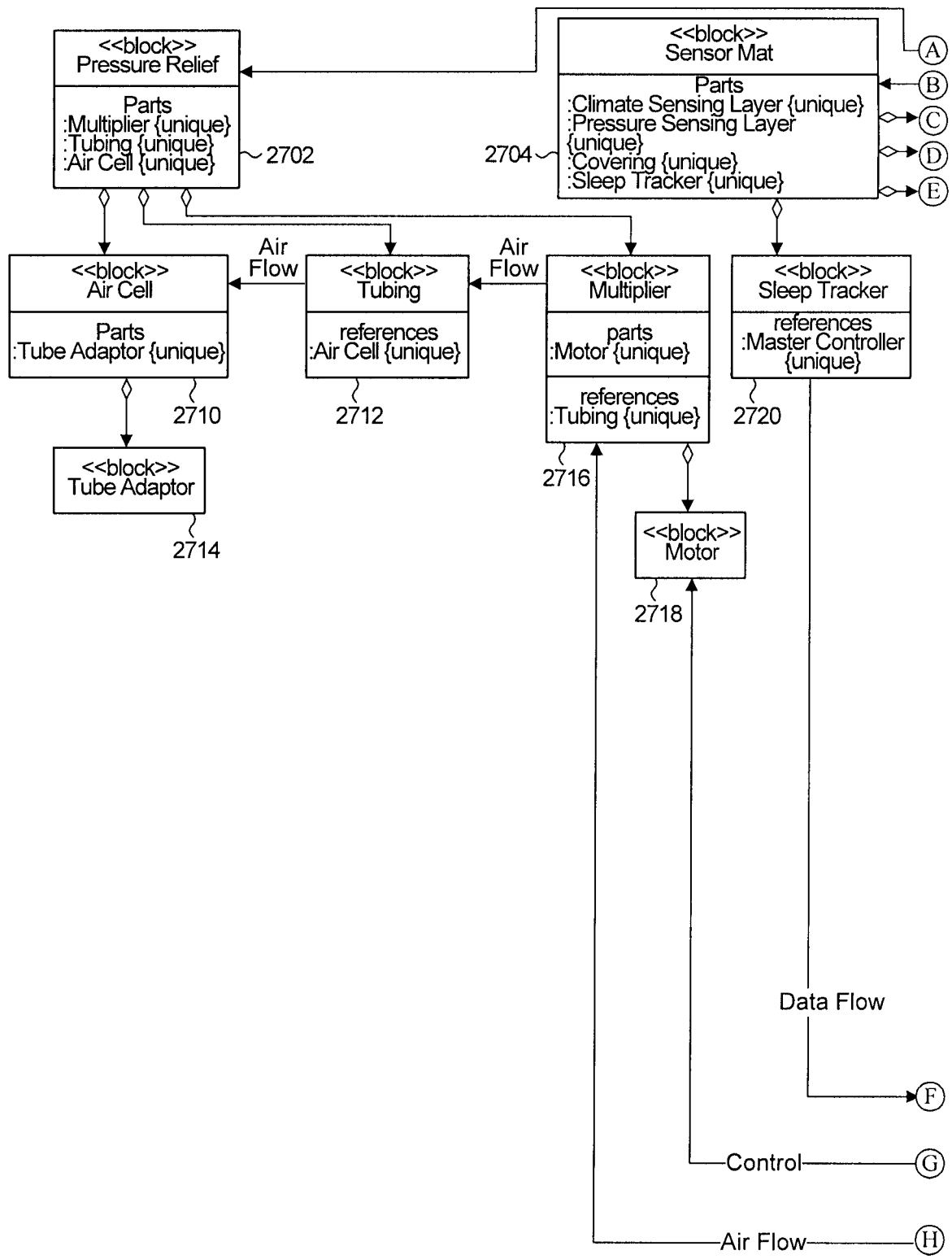
FIGS. 27A, 27B and 27C illustrate a block diagram depicting a pressure injury management system, according to some embodiments.
Figure 27B:
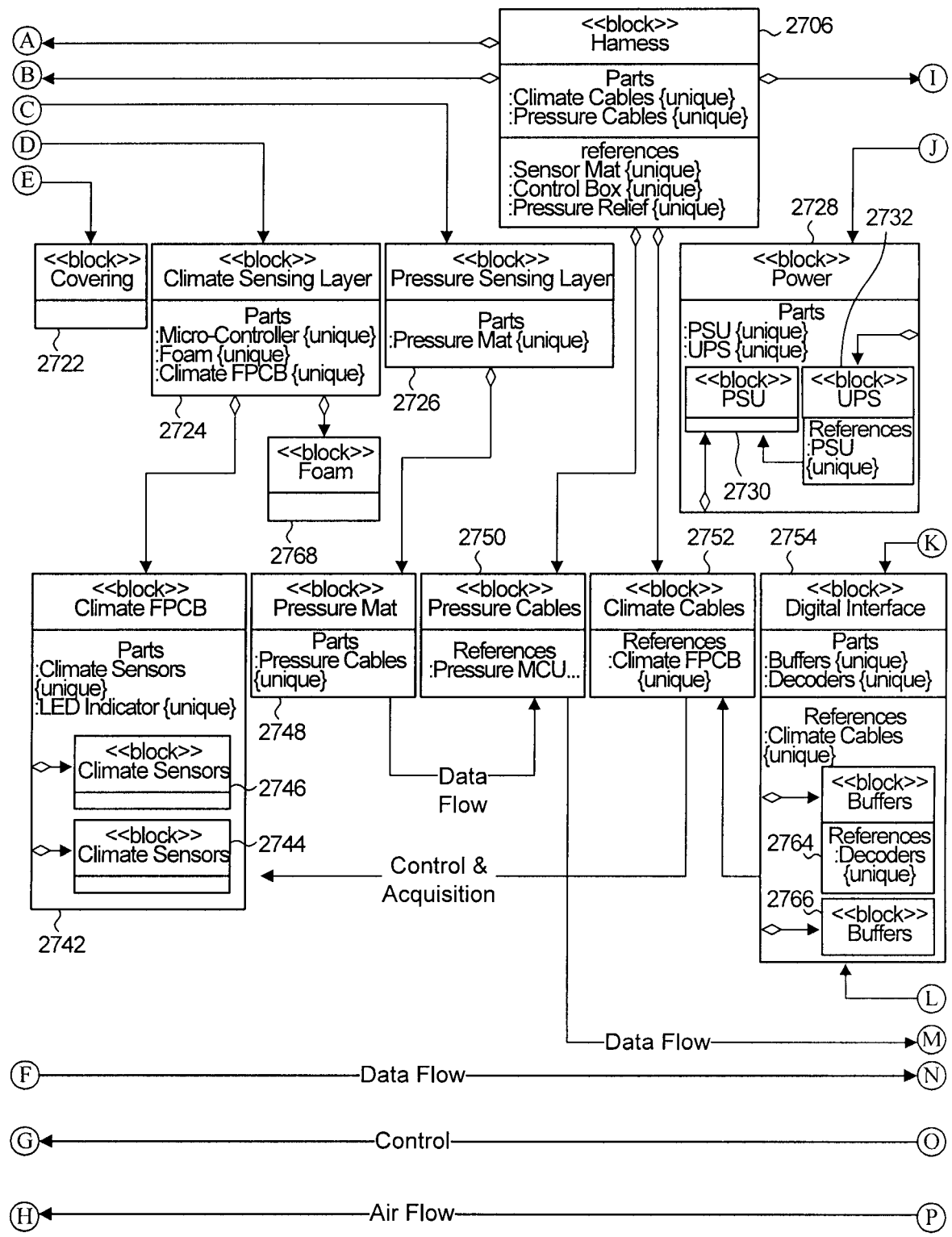
Figure 27C:
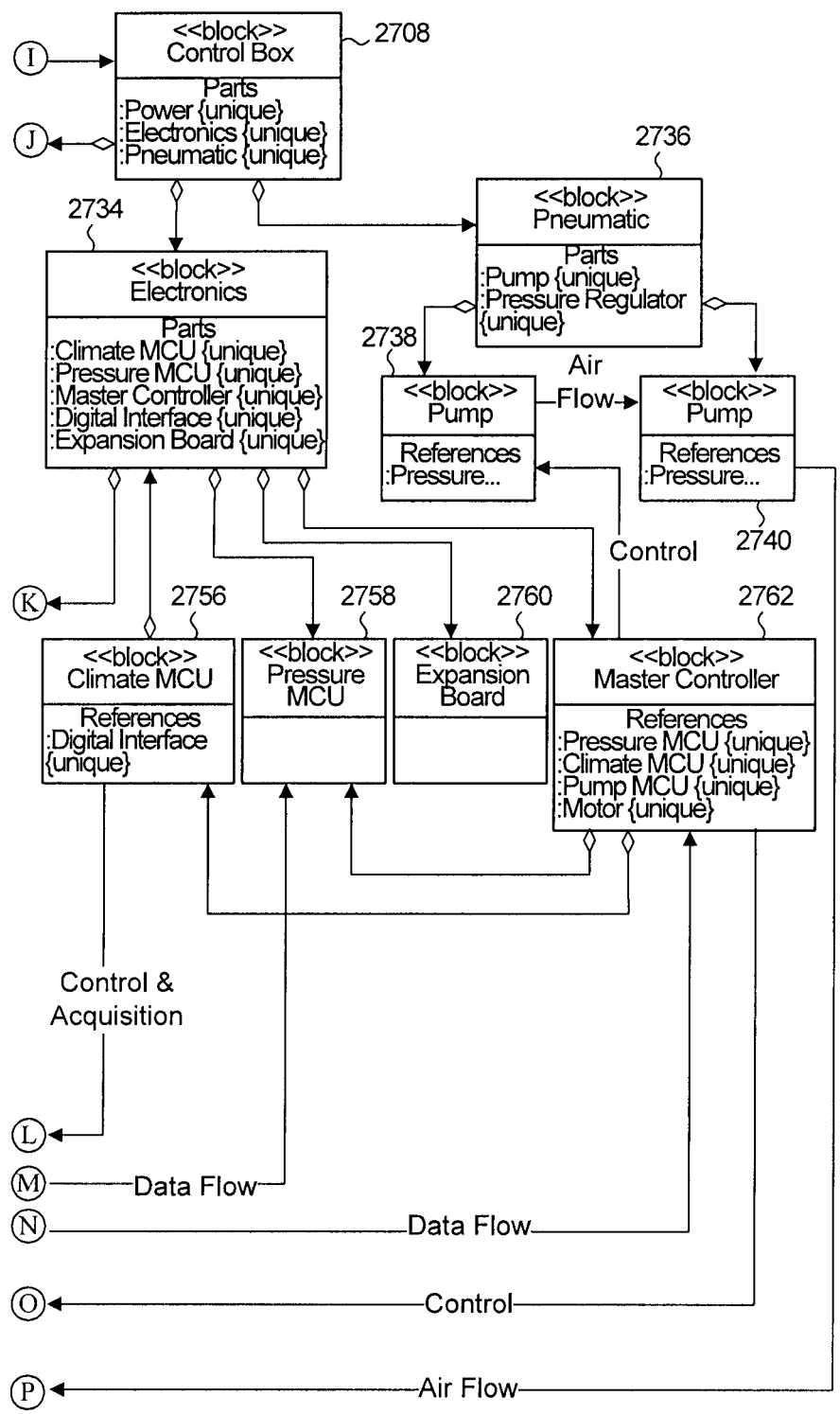

Referring now to FIGS. 27A, 27B and 27C, a non-limiting block diagram depicting components of a pressure injury management system may be provided, according to some embodiments.

In some embodiments, the harness 2706 may be a passive media that may function to link the control box 2708 and the pressure injury management system 100. The main function of harness 2706 may be to contain and protect all cables and tubes.

In some embodiments, climate cables 2752 may be one or more electronic cables functional to link electronic components of the climate sensing layer 2724 to the control box 2708. The climate cables 2752 may also connect the digital interface 2754 with climate flexible PCB (climate FPCB) 2742 and may also connect multiple climate flexible PCBs 2742 to one another in order transmit digital signals, power, etc. to and/or through them.

In some embodiments, pressure cables 2750 may refer to one or more cables (e.g., electronic cables) which may link the pressure sensing layer 2726 to the control box 2708.

In some embodiments, sensor mat 2704 may refer to a physical mat that a user (e.g., a hospital patient) may lie atop. Sensor mat 2704 may comprise climate sensing layer 2724, pressure sensing layer 2726, a covering 2722, and other components described herein, and may employs said components in order to collect data measuring various bio signals from patient (e.g., by reading moisture, temperature from skin and/or sensing pressure exerted by patient's body upon components within sensor mat 2704). Collected data may be read and processed in real time.

In some embodiments, sensor mat 2704 may comprise two individual layers, each with its own components. The first of these layers may be a climate sensing layer 2724 and the second may be a pressure sensing layer 2726. Sensor mat may further include one or more light emitting diode (LED) indicators which may form part of climate sensing layer 2724, or pressure sensing layer 2726, and may function to provide visual indications of various operating statuses of the components of the system 100. In some embodiments, the sensor mat may further include components functional to provide a sleep tracker 2720. Sleep tracker may leverage data collected via pressure sensing layer 2726, climate sensing layer 2724, and other sensors (e.g., microphones) in order to collect and analyze data in order to measure various characteristics of a user while asleep.

In some embodiments, pressure sensing layer 2726 may measure and monitor user's position, evaluate data to indicate patient comfort level, identify various points on user's body at risk of suffering pressure injuries(e.g., risk areas), identify if pressure is being, or has been, exerted upon risk areas, measure user's position for various wellness purposes among other applications (e.g., sleep monitoring, injury monitoring). Pressure sensing layer 2726 may comprise a modular system suited for multiple applications involving body pressure and bio signal measurement.

In some embodiments, pressure sensing layer 2726 may be suitable for use for product development in health & wellness industries for bedding or seating applications. Non-limiting examples may include: measuring and monitoring user position; evaluating patient comfort; identifying pressure on risk areas; measuring user's position for wellness purposes (e.g., sleep monitoring); and other applications.

In some embodiments, pressure sensing layer 2726 may allow for the detection of non-uniform pressures exerted upon a surface which may increase risk of skin ulcers forming upon the body of a user. Accurate monitoring of pressures exerted upon a surface by a user's body (as may be provided by pressure sensing layer 2726) may allow system 100 to generate alarms, notifications, reports, user redistribution (e.g., re-positioning of a body of a patient upon a hospital bed) schedules, or other suggested interactions with users which may reduce the risk of injury (including, but not limited to, pressure injuries and skin ulcers).

In some embodiments, climate sensing layer 2724 may measure and monitor various characteristics of the body of a user. These characteristics may include the temperature and the humidity of the user's body. In order to accomplish this, climate sensing layer 2724 may employ one or more climate sensors 2746, which may be connected to a microcontroller (e.g., a climate microcontroller (climate MCU) 2756), and may transmit and receive data from such microcontroller using a digital data transfer protocol.

In some embodiments, climate sensing layer 2724 may comprise a plurality of climate sensors 2746 which may be mounted directly upon one or more flexible PCBs (e.g., climate FPCB 2742). Flexible PCBs may be connected to one another via flat flexible cables (e.g., climate cables 2752) which may function to transmit data and power to and/or from climate sensing layer 2724 and components thereof.

In some embodiments, climate FPCB 2742 may comprise two layers flexible PCB located directly atop sensor mat 2704. This configuration may ensure that temperature sensors forming part of climate sensing layer 2724 remain close to the body of a user atop the system 100. In some embodiments it may be necessary for climate sensors 2746 in the climate sensing layer 2724 to remain sufficiently proximate to the body of a user in order to ensure accurate readings.

In some embodiments, climate FPCB 2742 may have climate sensors (which may be surface mounted design or "SMD" climate sensors) directly mounted to it in addition to any required SMD resistors, capacitors and/or LEDs. In some embodiments, climate FPCB 2742 may further comprise data connectors which may function to provide protocol input and output lines as well as data transfer lines functional to convey measurements recorded by climate sensors 2746. In some embodiments, climate FPCB 2742 may be single sided. Such a single sided design may gave climate FPCB 2742 more flexibility and reliability. The dimensions of climate FPCB may be homogeneous, so the board will handle more bending and pressure.

In some embodiments, climate FPCB 2742 may house one or more climate sensors 2746. In a non-limiting example, climate sensors 2746 may be 3.5V, 0.5 C accuracy, digital Serial Peripheral Interface (SPI)/inter-integrated circuit (I2C) SMD sensors. Climate sensors 2746 may be mounted directly on the climate flexible PCB.

In some embodiments, climate sensors 2746 may include combined digital humidity and temperature sensors based on proven sensing principles. In a non-limiting example, a climate sensor 2746 sensor module may be housed in an extremely compact metal-lid land grid array (LGA) package with a footprint of only 2.5×2.5 $mm^2$ and a height of 0.93 mm. In some embodiments, climate sensor 2746 may achieve high performance in all applications requiring humidity and temperature measurement. Multiple use cases of system 100 may require a high accuracy and a low TCO at the same time (e.g., home automation control, indoor navigation, health care as well as GPS refinement). The configuration of climate sensors 2746 may result in fast response times suitable for fast context awareness applications and high overall accuracy over a wide range of temperatures. Climate sensors 2746 may also be optimized for low noise and high resolution.

In some embodiments, climate sensing layer 2724 may include one or more SMD LED indicators 2744 which may function to indicate one or more critical positions after a user (e.g., a hospital patient) leaves the sensor mat 2704 of the system 100. LED indicators 2744 operators of system 100 (e.g., nurses) to determine the areas in the body that may be at high risk of developing injuries (e.g., pressure injuries, skin ulcers).

In some embodiments, a thin layer of foam may be included above climate sensors 2746 on climate sensing layer 2724 in order to prevent the body of a user (e.g., a hospital patient) from direct touching SMD components on the climate FPCB (e.g., climate sensors 2746, LED indicators 2744).

In some embodiments, a covering 2704 may be included atop sensor mat 2704. In some embodiments it may be critical to the proper function of the system 100 that a suitable covering 2704 is used which interfaces between the system 100 and external environment. It may be necessary that covering 2704 be permeable to water vapour and that covering 2704 is low profile in order to prevent distortion of pressure and temperature readings recorded by the components of the pressure sensing layer 2726 and climate sensing layer 2724. Another major constraint to choice of construction materials for the covering 2704 may be that such materials may need to be waterproof in order to prevent fluids from entering system 100. IN a non-limiting example, Polytetrafluoroethylene fabric membranes may be used to meet these requirements, and may allow for proper measurement of environmental signals from the climate sensing layer 2724 and pressure signals from the pressure sensing layer 2726 while protecting the system from damage due to contact between fluid and electronic components.

In some embodiments, sleep tracker 2720 may utilize low-profile sleep tracking sensors embedded into the sensor mat 2704, which may enable the system 100 to monitor users for possible anomalies in sleep habits—which anomalies may be indicative of possible complications or health risks. Leveraging sleep trackers 2720 may allow system to detect when a user is asleep, which may enable customized notifications to operators (e.g., nurses) and customized technical system actions (e.g., automatic redistribution). As a non-limiting example, sleep tracker 2720 may detect when a user is awake or asleep and schedule manual or automatic redistribution accordingly in order to reduce interference with users' during sleep (including deep sleep).

In some embodiments, control box 2708 may contains active components forming part of system 100. Active components may include, as a non-limiting example: controllers (e.g., climate MCU 2756, pressure MCU 2758, master controller 2762), supply units (e.g., power supply unit (PSU) 2730, pneumatics 2736 (e.g., pump), and interfaces (e.g., digital interface 2754).

In some embodiments, control box 2708 may be physically situated outside of the body the sensor mat 2704, and may house components that send and receive the electrical, pneumatic and electronic signals to and/or from the components within the sensor mat 2704. This configuration may increase ease for operators (e.g., nurses, family members providing home care, etc.) as the control box 2708 may only require plugging into electrical power (e.g., a wall outlet).

In some embodiments, power 2728 may comprise electrical components of the system 100 that feed and/or maintain supply voltage with the suitable power. Power 2728 may also comprise the main power supply cable that should be plugged to electrical power (e.g., a 110V outlet) in order to supply electrical power required by various components of the sensor mat 2704, control box 2708 and/or pressure relief system 2702.

In some embodiments, power supply unit (PSU) 2730 may provide suitable supply electrical supply to all system components: e.g., sensors, micro-controllers, logic circuits pump 2738, multiplier 2716, etc. An uninterruptable power supply (UPS) 2732 may operate in concert with PSU 2730 in order to maintain stability the stability of various characteristics of electrical supply entering the system 100.

In some embodiments, pneumatics 2736 may include mechanical components that form the pneumatic components of system 100. Components of pneumatics 2736 may include pressure pump 2738 and pressure regulator 2740.

In some embodiments, pressure pump 2738 may perform two main functions. First, pressure pump 2738 may compensate for probable air leaks from the air cells 2710 in the pressure relief 2702 in order to maintain constant or near-constant normal pressure in normal operating situations. Second, pressure pump 2738 may introduce and/or remove air from air cells 2710 in order to increase and/or reduce the pressure therein where the applicable air cells 2710 are located at positions proximate to certain points of body of a user (e.g., a hospital patient), if directed by the system 100. As a non-limiting example, pressure pump 2738 may increase air pressure in a set of air cells 2710 adjacent to a body part of a user deemed not to be at risk of pressure injury, pressure pump may 2738 also decrease air pressure in a set of air cells 2710 adjacent to a body part deemed to be at high risk of suffering a pressure injury.

In some embodiments, pressure regulator 2740 may be located connected at the output of the pressure pump 2738 in order to maintain regularity of airflow exiting pressure pump 2738 thereby making it suitable for the tubing 2712 and air cells 2710.

In some embodiments, the system 100 may include a pressure relief 2702. Pressure relief 2702 may be an important part of features of system 100 which may be designed to ensure user safety and comfort. In a non-limiting example, pressure relief 2702 may comprise the portion of the system 100 which contains the air cells 2710s, the multipliers 2710s, and tubing 2712. Further to this non-liming example, artificial intelligence algorithms may determine that the body situation of a user atop sensor mat 2704 should be changed and signals may be sent from master controller 2762 to the pressure pump 2738 and multiplier 2710 which may cause pressure pump 2738 and multiplier 2710 to operate in a fashion which may cause a change the air volume one or more designated air cells 2710s.

In some embodiments, a plurality of air cells 2710 may be provided. Air cells 2710 may form part of pressure relief 2702, and may, in an non-limiting example, take the form of a plurality of cubed Polyvinyl chloride (PVC) unit with at least one tube adaptor connected to at least one air cell 2710 via at least one tubing 2710 which may supply airflow. The air cell 2710 may be a is a basic unit of the construction of sensor mat 2704, and may function to redistribute pressure exerted between the various parts of user's body and sensor mat 2704 in response to various sensor data (e.g., pressure, temperature, wetness, etc.) captured and processed by system 100.

In some embodiments, multiplier 2716 may be an active, motor driven component which may function to distribute airflow from a single inlet to multiple outlets (said inlet and outlets forming part of multiplier 2716. For an example, a motor 2718 may align two disc portions of multiplier 2716 in a manner that creates a pathway through which air may travel from a pressure pump 2738 to through multiplier 2716, to one or more air cells 2710. In some embodiments, master controller 2762 may issue control commands which may cause multiplier 2716 to execute a specific degree turn, thus arranging the two disc portions of multiplier 2716 in a manner that aligns outlets on the multiplier 2716 with specific tubing 2712 connected to specific air cells 2710—this may cause pressure pump 2738 to fill the specific air cells 2710 with air. This specific design of multiplier 2716 may enable profile and/or cost reduction by enabling the control of air pressure in multiple air cells 2710 from a single motor 2718.

In some embodiments, motor 2718 may be one or more stepper motors controllable by master controller 2762. By rotation of a motor arm, motor 2718 may cause rotation of one or more multiplier 2716 components, which may cause airflow through multiplier 2716 outputs to travel through the specific tubing 2712 to one or more desired air cells 2710 as determined by the master controller 2762.

In some embodiments, tubing 2712 may comprise a plurality of tubes located at the bottom side of the air cells 2710. The function of tubing 2712 may be to carry distributed air that pressure pump 2738 may cause to be transferred through specifically selected outputs of multiplier 2716 as designated by master controller 2762, said distributed air ultimately arriving in one or more air cells 2710. Tubing 2712 may be connected to multiplier 2716 via one or more angel connectors, and to air cells 2710 by one or more tube adaptors to ensure air-tight connection and prevent air leakage.

In some embodiments, electronics 2734 may include the low voltage, logical, intelligent components of system 100 that may execute the process of reading, transmitting and analyzing the data collected by various sensors (e.g., climate sensors 2742, pressure sensors, etc.).

In some embodiments, master controller 2762 may include, for example, a credit-card sized single board computer Raspberry Pi®, PC or PLC. Master controller 2762 may receive, process, and manage imported data from the microcontrollers (e.g., climate MCU 2756, pressure MCU 2758), which data may include measurements of pressure climate values. Some embodiments may require a single master controller 2762 connected to climate MCU 2756, pressure MCU 2758.

In some embodiments, climate MCU 2756 may act as a slave controller or associate device between the master controller 2762 and climate sensors 2746. Climate MCU 2756 may be connected to master controller 2762 by a bus (e.g., a universal serial bus (USB) port) and may be connected to sensors by a digital protocol (SPI/I2C). Climate MCU 2756 may process and execute computer code to organize reading procedures from the various sensors and may send all data read from the various sensors to the master controller 2762.

In some embodiments, climate MCU 2756 may also provide supply voltage to the sensors (e.g., climate sensors 2746) by one or more 3.3V outputs and may further provide supply voltage to logic devices (e.g., digital interface 2754) by one or more 5V outputs. In some embodiments climate MCU 2756 may be an Arduino® controller, which may provide many features including, large memory, fast clock speed, C++ programmable architecture, and USB interface that may provide both serial connection and supply source. The ability to supply logic devices and sensors with different voltages, a variety of communication interfaces, and large variety and number of inputs and outputs may be beneficial in selecting a climate MCU 2756.

In some embodiments, pressure MCU 2758 may acts as a slave controller or associate device between the master controller 2762 and various components in pressure sensing layer 2726 (e.g., pressure mat 2748). Pressure MCU 2758 may be connected to master controller 2762 by a bus (e.g., a USB port) and may be connected to the sensors in the pressure sensing layer 2726 by a digital protocol (e.g., SPI/I2C).

In some embodiments, pressure MCU 2758 may execute computer code that may manage the reading procedures from the sensors (e.g., sensors within pressure mat 2748) and may cause resulting data to be transmitted to master controller 2762. Pressure MCU 2758 may also provide supply voltage to sensors (e.g., via one or more 3.3V outputs) and to logic devices (e.g., by a 5V output). Pressure MCU 2758 may be an Arduino® controller, which may provide many features including, large memory, fast clock speed, C++ programmable architecture, and USB interface that may provide both serial connection and supply source. The ability to supply logic devices and sensors with different voltages, a variety of communication interfaces, and large variety and number of inputs and outputs may be beneficial in selecting a pressure MCU 2758.

In some embodiments, expansion board 2760 may be an additional interfacing board that may allow master controller 2762 to manage add-on components attached to system 100. For example, master controller 2762 may record bio-signals detected by an add-on device and write the resulting data to a Database. Expansion board 2760 may ensure system 100 flexibility, scalability and may facilitate future upgrades.

In some embodiments, digital interface 2754 may comprise two layers of PCB that may contain logic circuits such as decoders, buffers, pull-up resistors and coupling capacitors, as well as terminals that may feed the digital interface 2754 with signals such as addressing lines, SPI lines, I2C lines and (power) supply lines. Digital interface 2754 may also contain connectors to buses that may enable transmission of supply and digital signals to flexible PCBs. Digital interface 2754 could, in a non-limiting example, take the form of a separate PCB or an Arduino® shield PCB.

In some embodiments, digital interface 2754 may include one or more decoders 2766. For example, a combination of 2×4 and 4×16 decoders/de-multiplexes may be included, said combination functional to generate the chip select (CS) signals for SPI sensors according to the given address designated by a particular microcontroller (e.g., climate MCU 2756 or pressure MCU 2758). In some embodiments a received "high" on an enable input may force at least one corresponding output into the high state.

In some embodiments, digital interface 2754 may perform a demultiplexing function by using input lines to select the output lines and using at least one enable as the data input while maintaining the other enable low. The methodology of using decoders/demultiplexers may be very effective with the SPI protocol because it may ensures that only one sensor is activated at a given time. This may prevent sensor-data collision and may avoid producing un-useful readings. Another important feature provided by digital interface 2754 may be high noise immunity and high speed performance of the decoders since they may be direct Transistor-transistor logic (TTL) devices with no clock signal, thus synchronization may not be required and delay may be only a few nanoseconds.

In some embodiments, one or more buffers 2764 may be included. For example, one or more line buffers may be included between the outputs of a microcontroller and the inputs of the related decoders in order to maintain the addressing signals. These buffers 2764 and drivers may feature high voltage open-collector outputs which may be suitable for interfacing between high-level circuits or for driving high current loads. Buffers 2764, may also be suitable for use as buffers for driving TTL inputs. These circuits may be highly compatible with most TTL families. Inputs of buffers 2764 may be diode clamped to minimize transmission-line effects, this may also simplify design. Power dissipation may be low, and average propagation delay time may also a few nanoseconds. Using buffers 2764 may improve functionality of system 100 by, enabling the sharing of all address lines of a given microcontroller with all buffers without causing the "fan-out problem" since their inputs consume low current while their outputs supply high current in order to feed larger number of TTL inputs.

Figure 28:
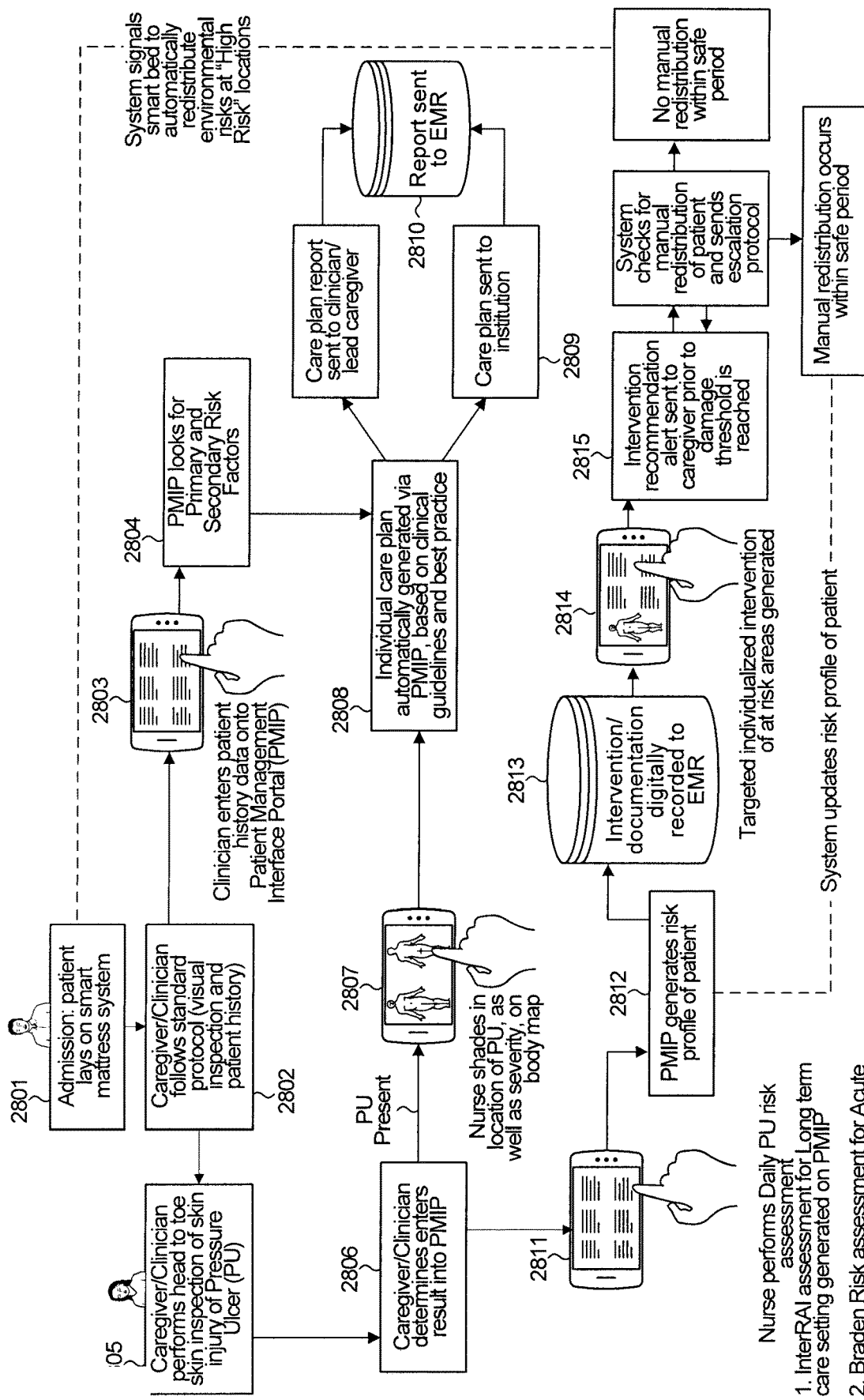
FIG. 28 is a flow-chart showing a pressure injury prevention process, according to some embodiments.

Referring now to FIG. 28, there is provided an example pressure injury prevention process, according to some embodiments. Pressure injury knowledge and prevention has increased substantially in recent decades, with multiple guidelines targeted their prevention, with treatments available. However, research suggests that translating available knowledge into bedside clinical decision-making is complicated by many factors, including difficulties implementing lengthy, time-consuming care guidelines; faulty communication; limited education; and poor standardization.

Some embodiments provided herein may enhance the abilities of nurses and clinicians to care for pressure injuries, while supporting best practice and guidelines, in patient care settings (e.g., acute, long term care, home care).

According to some embodiments, FIG. 28 may depict a process by which the systems, methods, and devices disclosed herein may help capture larger amounts of information into a more readily applicable treatment process. This process may present a multi-component PU prevention with a built in patient safety strategy which automatically updates based on real-time patient biosensor data and may allow for incorporation of decision making done by clinicians and caregivers.

According to some embodiments, this process may: 1) Identify individuals at risk for developing pressure injuries; 2) Identify localized zones of risk before tissue damage occurs; 3) Initiate early prevention programs, protocols, recommendations, and interventions, by involving key stakeholders in the prevention' strategy and intelligent machines; 4) Identify location, time and steps taken to identify where pressure injuries come from; 5) Provide in-depth visualization, in real-time, for ongoing monitoring; 6) Allow nursing homes, acute care, long term care, and other facilities to monitor acquired and admission acquired, as well as stage of pressure injuries; 7) Implement appropriate strategies/plans to a. attain/maintain intact skin, b. prevent complications, c. promptly identify and manage complications, d. involve patient and caregiver in self-management; and, 8) Implement cost-effective strategies/plans for prevention and treatment of pressure injuries.

According to some embodiments, at 2801 Program initiation may occur when user lays on device. At 2802 a caregiver follows standard pressure injury protocol, starting with first evaluating the individuals risk for developing a PU. At 2803, a clinician/caregiver answers a questionnaire generated by software elements of the system 100 (e.g., via a web portal), (device can be mobile device, tablet, desktop, etc.). Questionnaire may pertain to patient's clinical history. Questions may be targeted towards primary and secondary risk factors, such as surgery, and medications that may influence blood flow. At 2804, software elements of the system may feed questionnaire response data into patient an individualized care plan associated with the patient. At 2805. clinician/caregiver may perform visual inspection (head to toe) for skin injury or pressure ulcers, most particularly of all bony prominences. Visual skin inspection must take place on a daily basis. Special garments, shoes, heel and elbow protectors, orthotic devices, restraints, and protective wear should be removed for skin inspection.

At 2806 a Caregiver/clinician may select "Yes"/"No" whether a pressure injury is present or not. At 2807, if "Yes", full anatomical body map may be displayed and a user may select location of pressure injury or compromised skin. The longer the clinician/caregiver holds their the pointer in one spot, the higher the severity may be indicated to the map. This input may automatically populate a risk assessment scale (based on the figure at 2811. Notification of admitting physician that there is a pressure injury and associated may automatically be produced.

At 2808, individualized care plans may be generated via PMIP, based on up to date clinical guidelines and best practices. Care plans may include implementation guidelines based on current available resources of the institution. Also included may be a list of the most critical and high risk patients, including a list of interventions taken and not taken.

At 2809 only send salient points may be delivered in the form of a fact sheet to user (e.g., nursing home staff members, clinicians/lead caregiver, and institution). At 2810, up to date tracking and versioning may be saved.

At 2811, as part of the daily assessment a clinician/caregiver may perform a daily risk assessment. The system may populate automatically with questionnaire template based on one or more 'state of the art' risk assessment tools that have been clinically validated (e.g., Braden for Acute care and interRAI for LTC). This may be configured when system is installed in patient setting).

At 2812, system may perform daily holistic review of risk factors for pressure injury risk assessment. Using inputs, the system may generate a risk profile of patient, both locally and as a whole on a schedule basis (e.g., every 15 minutes).

At 2813, any intervention and non-intervention, as well as data inputs may be saved and populated into an individualized care plan, to maintain an up-to-date report, that may be sent out daily and weekly to various users.

At 2814, full body visualization of "safe, intervention required, damage critical" areas on the patient (e.g., using color coding) may be displayed.

At 2815, as at risk areas develop, risk notifications and alerts may be displayed or delivered to one or more devices.

At 2816, system may follow an escalation protocol and may increase notification escalation, in the form of messages, alerts at bedside system, and/or colour regions, etc., for high risk regions that develop or become further compromised. System may monitor automatically, whether manual redistribution has taken place.

At 2817, if no manual redistribution occurs within the allotted and acceptable range, the system may cause targeted interface pressure relief to be initiated in order to prevent tissue damage. System may record and update risk profile of patient at that localized zone, to both note that system altered pressure redistribution on its own.

At 2818, in an example scenario, a clinician/caregiver manually repositioned patient X. The system automatically recorded this action taking place, based on detected movement patterns of patient. The system updated risk profile accordingly.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the discussion herein, numerous references are made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described illustrated herein are intended to be exemplary only.

What is claimed is:

1. A system for monitoring sensor data of an entity undergoing prolonged contact with a surface, the system comprising:
   a pressure sensing layer comprising one or more sensors of a first type for detecting a first type of properties from the entity, the one or more sensors of the first type proximate to a contact between the entity and the surface, the one or more sensors of the first type including at least one sensor for measuring pressure;
   a climate sensing layer comprising one or more sensors of a second type for detecting a second type of properties from the entity, the one or more sensors of the second type proximate to the contact between the entity and the surface, the one or more sensors of the second type including at least one sensor for measuring one or more of temperature and humidity;
   a pressure relief system comprising at least one pressure redistributor for redistributing pressure exerted against the surface;
   a processor operably linked to the one or more sensors of the first type and the one or more sensors of the second type, the processor configured to:
   receive first sensor data from the one or more sensors of the first type;
   receive second sensor data from the one or more sensors of the second type;
   identify, by k-nearest neighbour (kNN) clustering, erroneous values from said sensors of the first and/or second type and replacing said erroneous values by inferring, by kNN clustering, replacement values for said erroneous values;
   combine received sensor data to produce a combined sensor data;
   generate a risk grid by segmenting the surface into a plurality of body areas, the risk grid based on a historical risk data set stored in a memory for each body area;
   detect at least one risk feature by processing the combined sensor data according to an AI model and the risk grid for at least one of said body areas;
   determine a pressure risk score based on the at least one risk feature;
   generate a pressure redistribution plan based on one or more of the pressure risk score and the at least one risk feature;
   transmit one or more of the pressure redistribution plan, the at least one risk feature, and the combined sensor data to a computer; and
   transmit the pressure redistribution plan to the pressure relief system for execution to redistribute the pressure exerted against the surface.

2. The system of claim 1, wherein upon receipt of the pressure instruction set from the processor, the pressure relief system automatically executes the pressure redistribution plan to redistribute pressure exerted against the surface.

3. The system of claim 1, wherein the processor transmits the pressure redistribution plan to the pressure relief system upon receiving, from a user, an acceptance command directing the system to execute the pressure redistribution plan.

4. The system of claim 1, wherein the one or more sensors of the first type is at least one Piezoresistive pressure sensor.

5. The system of claim 1, wherein at least one of the one or more sensors of the second type is a combined digital humidity and temperature sensor.

6. They system of claim 1, wherein the pressure relief system comprises:
   an air pump configured to receive instructions from the processor;
   a plurality of pressure-adjustable air cells connected to the air pump; and
   wherein, the air pump is configured to transfer air to or from, the plurality of pressure-adjustable air cells.

7. The system of claim 6, wherein the pressure relief system comprises:
   at least one valve multiplier configured to receive the instruction set from the processor, the at least one valve multiplier comprising:
   a plurality of outlets connectable to the plurality of pressure-adjustable air cells;

at least one inlet for receiving air from the pressure pump;

wherein the valve multiplier is configured to cause an air pressure of one or more selected air cells from among the plurality of pressure-adjustable air cells to be adjusted by the pump according to the received instruction set.

8. The system of claim 1, wherein the AI model applies a K Nearest Neighbor clustering pattern recognition method to increase resolution of at-the combined sensor data.

9. The system of claim 1, wherein the AI model applies a feature detection process in order to detect the at least one feature from the combined sensor data.

10. The system of claim 1, wherein the AI model applies a data filtration method in order to remove one or more insignificant data values from the combined sensor data.

11. The system of claim 1, wherein the AI model applies a susceptibility matrix process to produce the pressure risk score.

12. The system of claim 1, wherein the historical risk data set comprises one or more previously collected combined data sets.

13. The system of claim 1, wherein the sensor data related to the portions of the risk grid designated as the null area are truncated from the combined sensor data as an optimization step.

14. The system of claim 1, wherein the AI model performs a full-entity ensemble modeling process, the full-entity ensemble modeling process comprising:

apply a supervised machine learning pipeline process to build one or more ensemble models whereby the one or more ensemble models perform one or more voting rounds to select the most accurate AI process with specific regard to the combined sensor data.

15. A method for monitoring sensor data of an entity undergoing prolonged contact with a surface, the method comprising:

receiving first sensor data from one or more sensors of a first type arranged proximate to a contact between the entity and the surface, the one or more sensors of the first type including at least one sensor for measuring pressure;

receiving second sensor data from one or more sensors of a second type arranged proximate to the contact between the entity and the surface, the one or more sensors of the second type including at least one sensor for measuring one or more of temperature and humidity;

identifying, by k-nearest neighbour (kNN) clustering, erroneous values from said sensors of the first and/or second type and replacing said erroneous values by inferring, by kNN clustering, replacement values for said erroneous values;

combining received sensor data to produce a combined sensor data;

generating a risk grid by segmenting the surface into a plurality of body areas, the risk grid based on a historical risk data set stored in a memory for each body area;

detecting at least one risk feature by processing the combined sensor data according to an AI model and the risk grid for at least one of said body areas;

determining a pressure risk score based on the at least one risk feature;

generating a pressure redistribution plan based on one or more of the pressure risk score and the at least one risk feature;

transmitting one or more of the pressure redistribution plan, the at least one risk feature, and the combined sensor data to a computer; and receiving, at a pressure relief system comprising at least one pressure distributor for redistributing pressure exerted against the surface, the pressure redistribution plan as a set of computer-executable instructions.

16. The method of claim 15, comprising automatically executing the pressure redistribution plan to redistribute pressure exerted against the surface upon receipt of the pressure instruction set from the processor.

17. The method of claim 15, comprising transmitting the pressure redistribution plan to the pressure relief system upon receipt of an acceptance command from a user, the acceptance command containing instructions to execute the pressure redistribution plan.

18. The method of claim 15, comprising the AI model applying a K Nearest Neighbor clustering pattern recognition method to increase resolution of at the combined sensor data.

19. The method of claim 15, comprising the AI model applying a feature detection process in order to detect the at least one feature from the combined sensor data.

20. The method of claim 15, comprising the AI model applying a data filtration method in order to remove one or more insignificant data values from the combined sensor data.

21. The method of claim 15, comprising the AI model applying a susceptibility matrix process to produce the pressure risk score.

22. The method of claim 15, wherein the historical risk data set comprises one or more previously collected combined data sets.

23. The method of claim 15, wherein the sensor data related to the portions of the risk grid designated as the null area are truncated from the combined sensor data as an optimization step.

24. The method of claim 15, comprising:

redistributing, by the pressure relief system, pressure exerted against the surface according to the computer-executable instruction set.

25. A computer readable medium storing computer-executable instructions that, when executed by a computer, cause the computer to perform a method for monitoring sensor data of an entity undergoing prolonged contact with a surface, the method comprising:

receiving first sensor data from one or more sensors of a first type arranged proximate to a contact between the entity and the surface, the one or more sensors of the first type including at least one sensor for measuring pressure;

receiving second sensor data from one or more sensors of a second type arranged proximate to the contact between the entity and the surface, the one or more sensors of the second type including at least one sensor for measuring one or more of temperature and humidity;

identifying, by k-nearest neighbour (kNN) clustering, erroneous values from said sensors of the first and/or second type and replacing said erroneous values by inferring, by kNN clustering, replacement values for said erroneous values;

combining received sensor data to produce a combined sensor data;

generating a risk grid by segmenting the surface into a plurality of body areas, the risk grid based on a historical risk data set stored in a memory, for each body area;

detecting at least one risk feature by processing the combined sensor data according to an AI, model and the risk grid;

determining a pressure risk score based on the at least one risk feature;

generating a pressure redistribution plan based on one or more of the pressure risk score and the at least one risk feature;

transmitting one or more of the pressure redistribution plan, the at least one risk feature, and the combined sensor data to a computer; and receiving, at a pressure relief system comprising at least one pressure distributor for redistributing pressure exerted against the surface, the pressure redistribution plan as a set of computer-executable instructions.

26. The computer-readable medium of claim 25, wherein the method further comprises: redistributing, by the pressure relief system, pressure exerted against the surface according to the computer-executable instructions.

* * * * *